United States Patent
Weeden et al.

(10) Patent No.: US 12,128,109 B2
(45) Date of Patent: *Oct. 29, 2024

(54) MUSCLE TARGETING COMPLEXES AND FORMULATIONS FOR TREATING DYSTROPHINOPATHIES

(71) Applicant: Dyne Therapeutics, Inc., Waltham, MA (US)

(72) Inventors: Timothy Weeden, Waltham, MA (US); Scott Hilderbrand, Cambridge, MA (US); Sean Spring, Waltham, MA (US); Peiyi Shen, Waltham, MA (US); Cody A. Desjardins, Waltham, MA (US); Romesh R. Subramanian, Framingham, MA (US); Mohammed T. Qatanani, Waltham, MA (US); Brendan Quinn, Boston, MA (US); John Najim, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/455,351

(22) Filed: Aug. 24, 2023

(65) Prior Publication Data

US 2024/0016950 A1    Jan. 18, 2024

Related U.S. Application Data

(63) Continuation of application No. PCT/US2022/073540, filed on Jul. 8, 2022.
(Continued)

(51) Int. Cl.
*A61K 39/00* (2006.01)
*A61K 47/54* (2017.01)
(Continued)

(52) U.S. Cl.
CPC ........ *A61K 47/6807* (2017.08); *A61K 47/545* (2017.08); *A61K 47/548* (2017.08);
(Continued)

(58) Field of Classification Search
CPC .............. A61K 47/6807; A61K 47/545; A61K 47/548; A61K 47/65; A61K 47/6849
See application file for complete search history.

(56) References Cited

U.S. PATENT DOCUMENTS 2,631,173 A    3/1953   Hillyer et al.
6,214,345 B1   4/2001   Firestone et al.
(Continued)

FOREIGN PATENT DOCUMENTS

CN    102459597 A    11/2010
CN    103443125 A    12/2013
(Continued)

OTHER PUBLICATIONS

[No Author Listed] GenBank: AF095738.1. Mus musculus dystrophin gene, exons 22-25 and partial CDs. 2016. Retrieved from the internet Oct. 30, 2019: https://www.ncbi.nlm.nih.gov/nucleotide/AF095738.1?report=genbank&log$=nuclalign&blast_rank=3&RID=VKBMZ9WW014, 5 pages.
(Continued)

*Primary Examiner* — Sheela J. Huff
(74) *Attorney, Agent, or Firm* — Wolf, Greenfield & Sacks, P.C.

(57) ABSTRACT

Aspects of the disclosure relate to complexes and other aspects relate to formulations (e.g., aqueous, lyophilized forms) comprising such complexes (e.g., wherein each complex is of the exemplary formula shown below) comprising a phosphorodiamidate morpholino oligomer (e.g., useful for targeting DMD) covalently linked to an antibody (e.g., anti-TfR1 antibody). In some embodiments, the complexes are formulated with histidine (e.g., L-histidine) and sucrose at a specified pH (e.g., about 5.0 to 7.0). Also provided are uses of these formulations for treating a subject having a mutated DMD allele associated with Duchenne Muscular Dystrophy.

(Continued)

-continued

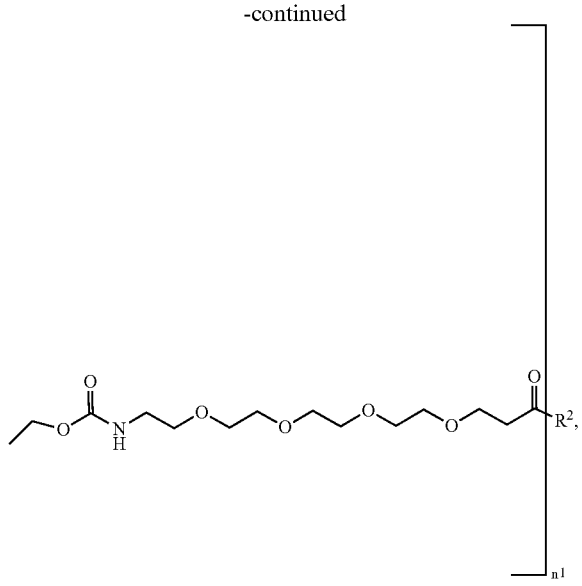

28 Claims, 4 Drawing Sheets

Specification includes a Sequence Listing.

Related U.S. Application Data

(60) Provisional application No. 63/220,426, filed on Jul. 9, 2021.

(51) Int. Cl.
  *A61K 47/65* (2017.01)
  *A61K 47/68* (2017.01)
  *A61P 21/00* (2006.01)

(52) U.S. Cl.
  CPC .......... *A61K 47/65* (2017.08); *A61K 47/6849* (2017.08); *A61P 21/00* (2018.01)

(56) References Cited

U.S. PATENT DOCUMENTS

| | | |
|---|---|---|
| 7,064,142 B2 | 6/2006 | Sato et al. |
| 7,265,131 B2 | 9/2007 | Johnson et al. |
| 7,534,879 B2 | 5/2009 | van Deutekom et al. |
| 7,575,886 B2 | 8/2009 | Venkataraman et al. |
| 7,902,160 B2 | 3/2011 | Matsuo et al. |
| 7,960,541 B2 | 6/2011 | Wilton et al. |
| 7,973,015 B2 | 7/2011 | van Ommen et al. |
| 8,084,601 B2 | 12/2011 | Graham et al. |
| 8,232,384 B2 | 7/2012 | Wilton et al. |
| 8,324,371 B2 | 12/2012 | Graham et al. |
| 8,361,979 B2 | 1/2013 | van Ommen al. |
| 8,455,636 B2 | 6/2013 | Fletcher et al. |
| 8,486,907 B2 | 7/2013 | Wilton et al. |
| 8,524,880 B2 | 9/2013 | Mcclorey et al. |
| 8,637,483 B2 | 1/2014 | Wilton et al. |
| 8,759,507 B2 | 6/2014 | van Deutekom et al. |
| 8,802,437 B2 | 8/2014 | Tremblay et al. |
| 8,859,629 B2 | 10/2014 | van Delft et al. |
| 8,865,883 B2 | 10/2014 | Kole et al. |
| 8,952,147 B2 | 2/2015 | Bouchard et al. |
| 9,018,368 B2 | 4/2015 | Wilton et al. |
| 9,024,007 B2 | 5/2015 | Wilton et al. |
| 9,078,911 B2 | 7/2015 | Lu et al. |
| 9,079,934 B2 | 7/2015 | Takeda et al. |
| 9,217,148 B2 | 12/2015 | Bestwick et al. |
| 9,222,940 B2 | 12/2015 | van Delft et al. |
| 9,228,187 B2 | 1/2016 | Meloni et al. |
| 9,243,245 B2 | 1/2016 | De Kimpe et al. |
| 9,260,371 B2 | 2/2016 | Bertozzi et al. |
| 9,416,361 B2 | 8/2016 | Iversen et al. |
| 9,422,555 B2 | 8/2016 | Wilton et al. |
| 9,447,415 B2 | 9/2016 | Wilton et al. |
| 9,504,758 B2 | 11/2016 | van Delft et al. |
| 9,506,058 B2 | 11/2016 | Kaye |
| 9,512,424 B2 | 12/2016 | Wantanabe et al. |
| 9,550,834 B2 | 1/2017 | Shirai et al. |
| 9,610,362 B2 | 4/2017 | Armstrong |
| 9,657,049 B2 | 5/2017 | Koizumi et al. |
| 9,657,050 B2 | 5/2017 | Koizumi et al. |
| 9,708,361 B2 | 7/2017 | Takeda et al. |
| 9,708,406 B2 | 7/2017 | Zhang et al. |
| 9,758,783 B2 | 9/2017 | Meloni et al. |
| 9,840,706 B2 | 12/2017 | Tetsuya et al. |
| 9,970,010 B2 | 5/2018 | Graham et al. |
| 9,988,629 B2 | 6/2018 | Takeda et al. |
| 9,994,851 B2 | 6/2018 | Wilton et al. |
| 10,100,304 B2 | 10/2018 | van Deutkom et al. |
| 10,131,682 B2 | 11/2018 | Zhao |
| 10,144,931 B2 | 12/2018 | Enya et al. |
| 10,190,116 B2 | 1/2019 | van Deutekom et al. |
| 10,238,753 B2 | 3/2019 | Armstrong |
| 10,239,807 B2 | 3/2019 | van Delft et al. |
| 10,266,502 B2 | 4/2019 | van Delft et al. |
| 10,287,586 B2 | 5/2019 | Wilson et al. |
| 10,337,003 B2 | 7/2019 | Kaye |
| 10,364,431 B2 | 7/2019 | Kaye |
| 10,385,092 B2 | 8/2019 | Watanabe et al. |
| 10,407,461 B2 | 9/2019 | Watanabe et al. |
| 10,434,111 B2 | 10/2019 | Bertozzi et al. |
| 10,450,568 B2 | 10/2019 | Butler et al. |
| 10,487,106 B2 | 11/2019 | Watanabe et al. |
| RE47,751 E | 12/2019 | Wilton et al. |
| RE47,769 E | 12/2019 | Wilton et al. |
| 10,533,171 B2 | 1/2020 | van Deutekom et al. |
| 10,533,174 B2 | 1/2020 | Iversen et al. |
| 10,550,188 B2 | 2/2020 | Geall et al. |
| 10,704,060 B2 | 7/2020 | Gersbach et al. |
| 10,752,898 B2 | 8/2020 | Pietri et al. |
| 10,781,451 B2 | 9/2020 | Wilton et al. |
| 10,876,114 B2 | 12/2020 | van Deutekom et al. |
| RE48,468 E | 3/2021 | De Kimpe et al. |
| 11,111,309 B2 | 9/2021 | Subramanian et al. |
| 11,168,141 B2 | 11/2021 | Subramanian et al. |
| 11,230,605 B2 | 1/2022 | Launay et al. |
| 11,248,056 B1 | 2/2022 | Subramanian et al. |
| 11,286,305 B2 | 3/2022 | Subramanian et al. |
| 11,369,689 B2 | 6/2022 | Subramanian et al. |
| 11,390,682 B2 | 7/2022 | Subramanian et al. |
| 11,497,815 B2 | 11/2022 | Subramanian et al. |
| 11,518,816 B2 | 12/2022 | Subramanian et al. |
| 11,633,496 B2 | 4/2023 | Subramanian et al. |
| 11,633,498 B2 | 4/2023 | Subramanian et al. |
| 11,638,761 B2 | 5/2023 | Subramanian et al. |
| 11,648,318 B2 | 5/2023 | Subramanian et al. |
| 11,672,872 B2 | 6/2023 | Subramanian et al. |
| 11,679,161 B2 | 6/2023 | Subramanian et al. |
| 11,759,525 B1 | 9/2023 | Subramanian et al. |
| 11,771,776 B2 * | 10/2023 | Subramanian ..... A61K 47/6807 424/181.1 |
| 11,787,869 B2 | 10/2023 | Subramanian et al. |
| 11,795,233 B2 | 10/2023 | Subramanian et al. |
| 11,795,234 B2 | 10/2023 | Subramanian et al. |
| 11,833,217 B2 | 12/2023 | Subramanian et al. |
| 11,839,660 B2 | 12/2023 | Subramanian et al. |
| 11,844,843 B2 | 12/2023 | Subramanian et al. |
| 11,911,484 B2 | 2/2024 | Subramanian et al. |
| 11,931,421 B2 | 3/2024 | Hilderbrand et al. |
| 11,969,475 B2 | 4/2024 | Subramanian et al. |
| 11,986,537 B2 | 5/2024 | Subramanian et al. |
| 2004/0063654 A1 | 4/2004 | Davis et al. |
| 2004/0191243 A1 | 9/2004 | Chen et al. |
| 2005/0084906 A1 | 4/2005 | Goetsch et al. |

(56) References Cited

U.S. PATENT DOCUMENTS

| | | |
|---|---|---|
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2007/0050146 A1 | 3/2007 | Bentwich et al. |
| 2008/0025913 A1 | 1/2008 | Bowdish et al. |
| 2008/0177045 A1 | 7/2008 | Lee et al. |
| 2009/0269755 A1 | 10/2009 | Aartsma-Rus et al. |
| 2010/0130591 A1 | 5/2010 | Sazani et al. |
| 2010/0168212 A1 | 7/2010 | Popplewell et al. |
| 2011/0256157 A1* | 10/2011 | Howard .............. C07D 487/04 540/496 |
| 2011/0263682 A1 | 10/2011 | De Kimpe et al. |
| 2012/0059042 A1 | 3/2012 | Platenburg et al. |
| 2012/0077860 A1 | 3/2012 | Garcia et al. |
| 2012/0122801 A1 | 5/2012 | Platenburg |
| 2012/0201809 A1 | 8/2012 | Bhat et al. |
| 2012/0270925 A1 | 10/2012 | Wilton et al. |
| 2013/0028891 A1 | 1/2013 | Penichet et al. |
| 2013/0041017 A1 | 2/2013 | Kaplan et al. |
| 2013/0066063 A1 | 3/2013 | Berry et al. |
| 2013/0072541 A1 | 3/2013 | Garcia et al. |
| 2013/0137763 A1 | 5/2013 | van Delft et al. |
| 2013/0177579 A1 | 7/2013 | Lin et al. |
| 2014/0105916 A1 | 4/2014 | Brasel et al. |
| 2014/0193436 A1 | 7/2014 | Prudent |
| 2014/0323552 A1 | 10/2014 | Burghes et al. |
| 2014/0363455 A1 | 12/2014 | Stull et al. |
| 2015/0064181 A1 | 3/2015 | Armstrong |
| 2015/0191725 A1 | 7/2015 | van Deutekom et al. |
| 2015/0196670 A1 | 7/2015 | Dickson et al. |
| 2015/0247141 A1 | 9/2015 | Uhlmann et al. |
| 2015/0258210 A1 | 9/2015 | van Delft et al. |
| 2015/0266954 A1 | 9/2015 | Davies et al. |
| 2016/0015828 A1 | 1/2016 | Torgov et al. |
| 2016/0053262 A1 | 2/2016 | Platenburg et al. |
| 2016/0107999 A1 | 4/2016 | Debets et al. |
| 2016/0175460 A1 | 6/2016 | Arathoon et al. |
| 2016/0235861 A1 | 8/2016 | van Delft et al. |
| 2016/0237157 A1 | 8/2016 | Dennis et al. |
| 2016/0250347 A1 | 9/2016 | van Delft et al. |
| 2016/0272973 A1 | 9/2016 | Shehadeh |
| 2016/0304864 A1 | 10/2016 | De Kimpe et al. |
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0072068 A1 | 3/2017 | Verkade et al. |
| 2017/0130256 A1 | 5/2017 | van Berkel et al. |
| 2017/0226554 A1 | 8/2017 | Wasiel et al. |
| 2017/0281795 A1 | 10/2017 | Geall et al. |
| 2017/0283799 A1 | 10/2017 | Kaye et al. |
| 2017/0348416 A1 | 12/2017 | Hasler et al. |
| 2018/0002433 A1 | 1/2018 | Zhang et al. |
| 2018/0028554 A1 | 2/2018 | De Visser et al. |
| 2018/0134797 A1 | 5/2018 | Zhang et al. |
| 2018/0142245 A1 | 5/2018 | Watanabe et al. |
| 2018/0171333 A1 | 6/2018 | Meloni et al. |
| 2018/0179538 A1 | 6/2018 | Takeda et al. |
| 2018/0265859 A1 | 9/2018 | Tremblay et al. |
| 2018/0369400 A1 | 12/2018 | Levin et al. |
| 2019/0000986 A1 | 1/2019 | Levin et al. |
| 2019/0008986 A1 | 1/2019 | Butler et al. |
| 2019/0038765 A1 | 2/2019 | van Berkel et al. |
| 2019/0092833 A1 | 3/2019 | Lin et al. |
| 2019/0092870 A1 | 3/2019 | Launay et al. |
| 2019/0112604 A1 | 4/2019 | De Kimpe et al. |
| 2019/0119383 A1 | 4/2019 | Bruenker et al. |
| 2019/0119679 A1 | 4/2019 | De Kimpe et al. |
| 2019/0127733 A1 | 5/2019 | Butler et al. |
| 2019/0153083 A1 | 5/2019 | Juste et al. |
| 2019/0177723 A1 | 6/2019 | Dickson et al. |
| 2019/0177725 A1 | 6/2019 | De Kimpe et al. |
| 2019/0209604 A1 | 7/2019 | Zhang et al. |
| 2019/0240346 A1 | 8/2019 | Sugo et al. |
| 2019/0249173 A1 | 8/2019 | Vargeese et al. |
| 2019/0270994 A1 | 9/2019 | Wilton et al. |
| 2019/0284556 A1 | 9/2019 | Sazani et al. |
| 2019/0298847 A1 | 10/2019 | Geall et al. |
| 2019/0323010 A1 | 10/2019 | Wilton et al. |
| 2019/0330626 A1 | 10/2019 | Rigo et al. |
| 2019/0336615 A1 | 11/2019 | Thompson et al. |
| 2019/0338311 A1 | 11/2019 | Amoasii et al. |
| 2019/0359982 A1 | 11/2019 | Kaye et al. |
| 2019/0364862 A1 | 12/2019 | Amoasii et al. |
| 2019/0390197 A1 | 12/2019 | Butler et al. |
| 2020/0040337 A1 | 2/2020 | Kaye et al. |
| 2020/0046742 A1 | 2/2020 | Bertozzi et al. |
| 2020/0046854 A1 | 2/2020 | Zhang et al. |
| 2020/0048174 A1 | 2/2020 | van Delft et al. |
| 2020/0123267 A1 | 4/2020 | Zhang et al. |
| 2020/0155702 A1 | 5/2020 | Bacica et al. |
| 2020/0239886 A1 | 7/2020 | De Kimpe et al. |
| 2020/0282074 A1 | 9/2020 | Levin et al. |
| 2020/0325237 A1 | 10/2020 | Darimont et al. |
| 2021/0038739 A1 | 2/2021 | Takahashi et al. |
| 2021/0130486 A1 | 5/2021 | Darimont et al. |
| 2021/0145852 A1 | 5/2021 | Passini et al. |
| 2021/0147576 A1 | 5/2021 | Laurent et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |
| 2023/0088865 A1 | 3/2023 | Subramanian et al. |
| 2023/0103793 A1 | 4/2023 | Subramanian et al. |
| 2023/0111147 A1 | 4/2023 | Subramanian et al. |
| 2023/0111212 A1 | 4/2023 | Subramanian et al. |
| 2023/0113823 A1 | 4/2023 | Subramanian et al. |
| 2023/0117883 A1 | 4/2023 | Subramanian et al. |
| 2023/0118799 A1 | 4/2023 | Subramanian et al. |
| 2023/0144436 A1 | 5/2023 | Subramanian et al. |
| 2023/0203180 A1 | 6/2023 | Subramanian et al. |
| 2023/0203181 A1 | 6/2023 | Subramanian et al. |
| 2023/0226212 A1 | 7/2023 | Subramanian et al. |
| 2023/0227569 A1 | 7/2023 | Subramanian et al. |
| 2023/0256112 A1 | 8/2023 | Subramanian et al. |
| 2023/0256113 A1 | 8/2023 | Subramanian et al. |
| 2023/0270873 A1 | 8/2023 | Subramanian et al. |
| 2023/0272065 A1 | 8/2023 | Subramanian et al. |
| 2023/0285582 A1 | 9/2023 | Subramanian et al. |
| 2023/0285586 A1 | 9/2023 | Subramanian et al. |
| 2023/0287108 A1 | 9/2023 | Subramanian et al. |
| 2023/0321264 A1 | 10/2023 | Subramanian et al. |
| 2023/0330247 A1 | 10/2023 | Hildebrand et al. |
| 2023/0330562 A1 | 10/2023 | Weeden et al. |
| 2023/0346966 A1 | 11/2023 | Subramanian et al. |
| 2023/0346967 A1 | 11/2023 | Subramanian et al. |
| 2024/0016952 A1 | 1/2024 | Subramanian et al. |
| 2024/0066139 A1 | 2/2024 | Subramanian et al. |
| 2024/0066140 A1 | 2/2024 | Subramanian et al. |
| 2024/0067743 A1 | 2/2024 | Subramanian et al. |

(56) References Cited

U.S. PATENT DOCUMENTS

| | | |
|---|---|---|
| 2024/0067744 A1 | 2/2024 | Subramanian et al. |
| 2024/0100177 A1 | 3/2024 | Hildebrand et al. |
| 2024/0110184 A1 | 4/2024 | Brown et al. |
| 2024/0117356 A1 | 4/2024 | Subramanian et al. |
| 2024/0148891 A1 | 5/2024 | Subramanian et al. |

FOREIGN PATENT DOCUMENTS

| | | |
|---|---|---|
| CN | 103732259 A | 4/2014 |
| CN | 108220418 | 6/2018 |
| CN | 109306375 A | 2/2019 |
| EP | 1479771 A2 | 11/2004 |
| EP | 1619249 A1 | 1/2006 |
| EP | 2203173 B1 | 7/2010 |
| EP | 2284264 A1 | 2/2011 |
| EP | 2426203 A2 | 3/2012 |
| EP | 2614827 A2 | 7/2013 |
| EP | 2801618 A1 | 11/2014 |
| EP | 2623609 B1 | 1/2017 |
| EP | 3238737 A1 | 11/2017 |
| EP | 2922818 B1 | 9/2018 |
| EP | 3473270 A1 | 4/2019 |
| EP | 3560958 A1 | 10/2019 |
| IL | 54795 A | 10/1980 |
| JP | 2002-253259 A | 9/2002 |
| JP | 2015-534996 A | 12/2015 |
| WO | WO 1989/007970 A1 | 9/1989 |
| WO | WO 1991/004753 A1 | 4/1991 |
| WO | WO 2006/000057 A1 | 1/2006 |
| WO | WO 2006/022688 A1 | 3/2006 |
| WO | WO 2007/135105 A1 | 11/2007 |
| WO | WO 2009/054725 A2 | 4/2009 |
| WO | WO 2009/144481 A2 | 12/2009 |
| WO | WO 2010/048586 A1 | 4/2010 |
| WO | WO 2010/050801 A1 | 5/2010 |
| WO | WO 2010/129861 A1 | 11/2010 |
| WO | WO 2011/057350 A1 | 5/2011 |
| WO | WO 2011/078797 A2 | 6/2011 |
| WO | WO 2011/136645 A1 | 11/2011 |
| WO | WO 2011/150408 A2 | 12/2011 |
| WO | WO 2011/154427 A1 | 12/2011 |
| WO | WO 2012/029986 A1 | 3/2012 |
| WO | WO 2012/075037 A1 | 6/2012 |
| WO | WO 2012/087962 A2 | 6/2012 |
| WO | WO 2013/026832 A1 | 2/2013 |
| WO | WO 2013/085550 A2 | 6/2013 |
| WO | WO 2013/100190 A1 | 7/2013 |
| WO | WO 2013/138662 A1 | 9/2013 |
| WO | WO 2013/162363 A1 | 10/2013 |
| WO | WO 2014/007620 A2 | 1/2014 |
| WO | WO 2014/065661 A1 | 5/2014 |
| WO | WO 2014/144978 A2 | 9/2014 |
| WO | WO 2014/153220 A2 | 9/2014 |
| WO | WO 2014/153240 A2 | 9/2014 |
| WO | WO 2015/042581 A1 | 3/2015 |
| WO | WO 2015/134365 A2 | 9/2015 |
| WO | WO 2015/179741 A1 | 11/2015 |
| WO | WO 2016/081643 A1 | 5/2016 |
| WO | WO 2016/081670 A2 | 5/2016 |
| WO | WO 2016/187425 A1 | 11/2016 |
| WO | WO 2016/205641 A2 | 12/2016 |
| WO | WO 2017/047707 A1 | 3/2017 |
| WO | WO 2017/100467 A2 | 6/2017 |
| WO | WO 2017/106643 A1 | 6/2017 |
| WO | WO 2017/143156 A1 | 8/2017 |
| WO | WO 2017/173408 A1 | 10/2017 |
| WO | WO 2017/192679 A1 | 11/2017 |
| WO | WO 2017/205191 A1 | 11/2017 |
| WO | WO 2017/205513 A1 | 11/2017 |
| WO | WO 2017/221883 A1 | 12/2017 |
| WO | WO 2018/007475 A1 | 1/2018 |
| WO | WO 2018/014042 A1 | 1/2018 |
| WO | WO 2018/017754 A1 | 1/2018 |
| WO | WO 2018/091544 A1 | 5/2018 |
| WO | WO 2018/098480 A1 | 5/2018 |
| WO | WO 2018/100010 A1 | 6/2018 |
| WO | WO 2018/107003 A1 | 6/2018 |
| WO | WO 2018/129296 A1 | 7/2018 |
| WO | WO 2018/129384 A1 | 7/2018 |
| WO | WO 2018/226861 A1 | 12/2018 |
| WO | WO 2019/014772 A1 | 1/2019 |
| WO | WO 2019/059973 A1 | 3/2019 |
| WO | WO 2019/060775 A1 | 3/2019 |
| WO | WO 2019/067975 A1 | 4/2019 |
| WO | WO 2019/071028 A1 | 4/2019 |
| WO | WO 2019/092507 A2 | 5/2019 |
| WO | WO 2019/113393 A1 | 6/2019 |
| WO | WO 2019/136180 A2 | 7/2019 |
| WO | WO 2019/136216 A1 | 7/2019 |
| WO | WO 2019/151539 A1 | 8/2019 |
| WO | WO 2019/152609 A1 | 8/2019 |
| WO | WO 2019/157224 A1 | 8/2019 |
| WO | WO 2019/200185 A1 | 10/2019 |
| WO | WO 2019/215175 A1 | 11/2019 |
| WO | WO 2019/215333 A1 | 11/2019 |
| WO | WO 2019/229658 A1 | 12/2019 |
| WO | WO 2019/241385 A2 | 12/2019 |
| WO | WO 2019/246480 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |
| WO | WO 2020/028857 A1 | 2/2020 |
| WO | WO 2020/028861 A1 | 2/2020 |
| WO | WO 2020/028864 A1 | 2/2020 |
| WO | WO 2020/084488 A1 | 4/2020 |
| WO | WO 2020/094670 A1 | 5/2020 |
| WO | WO 2020/132584 A1 | 6/2020 |
| WO | WO 2020/219820 A1 | 10/2020 |
| WO | WO 2020/247738 A1 | 12/2020 |
| WO | WO 2020/247782 A1 | 12/2020 |
| WO | WO 2020/247818 A1 | 12/2020 |
| WO | WO 2021/003573 A1 | 1/2021 |
| WO | WO 2021/068761 A1 | 4/2021 |
| WO | WO 2021/076856 A1 | 4/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |
| WO | WO 2022/026152 A1 | 2/2022 |
| WO | WO 2022/051665 A1 | 3/2022 |
| WO | WO 2022/056266 A2 | 3/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |
| WO | WO 2023/044398 A1 | 3/2023 |
| WO | WO 2023/077120 A1 | 5/2023 |

(56) References Cited

FOREIGN PATENT DOCUMENTS

| WO | WO 2023/086864 A1 | 5/2023 |
|---|---|---|
| WO | WO 2023/201318 A1 | 10/2023 |
| WO | WO 2023/201324 A1 | 10/2023 |
| WO | WO 2023/201332 A1 | 10/2023 |
| WO | WO 2024/011135 A1 | 1/2024 |
| WO | WO 2024/011150 A1 | 1/2024 |
| WO | WO 2024/097644 A1 | 5/2024 |

OTHER PUBLICATIONS

[No Author Listed] GenBank: CAE7739414. Unnamed protein product, partial [Symbiodinium pilosum]. Feb. 18, 2021. Retrieved from the internet Oct. 12, 2022: https://www.ncbi.nlm.nih.gov/protein/CAE7739414.1.1?report=genbank&log$=prottop&blast_rank=1&RID=MDW2CW3T013, 1 page.
[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.
[No Author Listed] GenBank: PKK91089. Hypothetical protein CVV64_04785 [*Candidatus wallbacteria* bacterium HGW-*wallbacteria*-1]. Oct. 13, 2017. Retrieved from the internet Oct. 12, 2022: https://www.ncbi.nlm.nih.gov/protein/PKK91089.1?report=genbank&log$=prottop&blast_rank=2&RID=MDW2CW3T013, 2 pages.
[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.
[No Author Listed] Wikipedia, Dystrophin, Mar. 9, 2018. Retrieved from the internet Nov. 5, 2019: https://en.wikipedia.org/w/index.php?title=Dystrophin&oldid=829543258, 10 pages.
[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.
[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.
[No Author Listed], Exondys (eteplirsen): EPAR—Refusal public assessment report and Annex: Scientific conclusions and grounds for refusal. European Medicines Agency. Sep. 20, 2018. 140 pages.
[No Author Listed], Building the world's leading muscle disease company. Dyne Company Overview. Jun. 2021. 42 pages.
[No Author Listed], Clinical trial summary NCT000159250 (Version 4, dated Oct. 11, 2007). 9 pages.
[No Author Listed], Highlights of prescribing information Exondys 51. FDA. <accessdata.fda.gov> Sep. 2016. Retrieved May 22, 2021. 11 pages.
[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.
[No Author Listed], Morpholino History, Production, and Properties. Gene Tools. Retrieved from https://gene-tools.com/history_production_and_properties. Accessed Jan. 9, 2023. 5 pages.
[No Author Listed], NCBI "NM_004006.2(DMD)". Published Oct. 30, 2020. Accessed from ncbi.nlm.nih.gov on May 21, 2021. 2 pages.
[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's TransferrinReceptor%2FCD71 Extracellular,molecular weight of 103.6 kDa (Year: 2021). 3 pages.
Aartsma-Rus et al., Antisense-induced multiexon skipping for Duchenne muscular dystrophy makes more sense. Am J Hum Genet. Jan. 2004;74(1):83-92. Epub Dec. 16, 2003.
Aartsma-Rus et al., Antisense-mediated exon skipping: a versatile tool with therapeutic and research applications. RNA. Oct. 2007;13(10):1609-24. doi: 10.1261/rna.653607. Epub Aug. 7, 2007.
Aartsma-Rus et al., Antisense-mediated modulation of splicing: therapeutic implications for Duchenne muscular dystrophy. RNA Biol. Jul.-Aug. 2010;7(4):453-61. doi: 10.4161/rna.7.4.12264. Epub Jul. 1, 2010.
Aartsma-Rus et al., Guidelines for antisense oligonucleotide design and insight into splice-modulating mechanisms. Mol Ther. Mar. 2009;17(3):548-53. doi: 10.1038/mt.2008.205. Epub Sep. 23, 2008.
Aartsma-Rus et al., Less is more: therapeutic exon skipping for Duchenne muscular dystrophy. Lancet Neurol. Oct. 2009;8(10):873-5. doi: 10.1016/S1474-4422(09)70229-7. Epub Aug. 25, 2009.
Aartsma-Rus et al., Progress in therapeutic antisense applications for neuromuscular disorders. Eur J Hum Genet. Feb. 2010;18(2):146-53. Epub Oct. 7, 2009.
Aartsma-Rus et al., Targeted exon skipping as a potential gene correction therapy for Duchenne muscular dystrophy. Neuromuscul Disord. Oct. 2002;12 Suppl 1:S71-7. doi: 10.1016/s0960-8966(02)00086-x.
Adams et al., Antisense oligonucleotide induced exon skipping and the dystrophin gene transcript: cocktails and chemistries. BMC Mol Biol. Jul. 2, 2007;8:57.
Agard et al., A Comparative Study of Bioorthogonal Reactions with Azides. ACS Chem. Biol. 2006;1(10):644-8. Epub Oct. 20, 2006.
Agard et al., A Strain-Promoted [3 + 2] Azide-Alkyne Cycloaddition for Covalent Modification of Biomolecules in Living Systems. J. Am. Chem. Soc. Nov. 2004;126(46):15046-7.
Alter et al., Systemic delivery of morpholino oligonucleotide restores dystrophin expression bodywide and improves dystrophic pathology. Nat Med. Feb. 2006;12(2):175-7. doi: 10.1038/nm1345. Epub Jan. 29, 2006.
Anciaux et al., Transition-metal-catalyzed reactions of diazo compounds. 1. Cyclopropanation of double bonds. The Journal of Organic Chemistry. Feb. 1980;45(4):695-702.
Antony-Mayer et al., Bicyclo[6.1.0]nonynes. Chemische Berichte. Nov. 1988;121(11):2013-8.
Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.
Arechavala-Gomeza et al., Comparative analysis of antisense oligonucleotide sequences for targeted skipping of exon 51 during dystrophin pre-mRNA splicing in human muscle. Hum Gene Ther. Sep. 2007;18(9):798-810. doi: 10.1089/hum.2006.061.
Arnett et al., Therapy for neuromuscular disorders. Curr Opin Genet Dev. Jun. 2009;19(3):290-7. doi: 10.1016/j.gde.2009.03.005. Epub May 4, 2009.
Ast et al., Estergruppenhaltige Polyalkenylene durch Olefin-Metathese. Die Makromolekulare Chemie. May 1976;177(5):1349-55.
Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.
Baskin et al., Copper-free click chemistry for dynamic in vivo imaging. PNAS. Oct. 2007;104(43):16793-7.
Beskrovnaya, FORCE™ platform delivers exon skipping PMO, leads to durable increases in dystrophin protein in mdx mice and is well tolerated NHPs. Presented at Muscle Study Group Annual Scientific Meeting. Oct. 1, 2021. 29 pages.
Bien-Ly et al., Transferrin receptor (TfR) trafficking determines brain uptake of TfR antibody affinity variants. J Exp Med. Feb. 10, 2014;211(2):233-44. Epub Jan. 27, 2014.
Black, 9.13.4.1.1.3.2 Variation 2: C-Alkylation (and Arylation) by Carbenes and Free Radicals. Science of Synthesis. 2001;9:514.
Bushby et al., MSG/ENMC for DMD Trial Study Group. 145th ENMC International Workshop: planning for an International Trial of Steroid Dosage Regimes in DMD (FOR DMD), Oct. 22-24, 2006, Naarden, The Netherlands. Neuromuscul Disord. May 2007;17(5):423-8. doi: 10.1016/j.nmd.2007.01.006. Epub Apr. 11, 2007.
Bushby et al., Report on the 124th ENMC International Workshop. Treatment of Duchenne muscular dystrophy; defining the gold

(56) References Cited

OTHER PUBLICATIONS standards of management in the use of corticosteroids. Apr. 2-4, 2004, Naarden, The Netherlands. Neuromuscul Disord. Sep. 2004;14(8-9):526-34.

Bushby et al., The multidisciplinary management of Duchenne muscular dystrophy. Curr Paed. 2005; 15: 292-300.

Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.

Campbell et al., Deflazacort for the treatment of Duchenne Dystrophy: a systematic review. BMC Neurol. Sep. 8, 2003;3:7. doi: 10.1186/1471-2377-3-7. Epub Sep. 8, 2003.

Candelaria et al., Antibodies Targeting the Transferrin Receptor 1 (TfR1) as Direct Anti-cancer Agents. Front Immunol. Mar. 17, 2021;12:607692.

Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.

Cenik et al., Argonaute proteins. Curr Biol. Jun. 21, 2011;21(12):R446-9.

Chothia et al., Canonical structures for the hypervariable regions of immunoglobulins. J Mol Biol. Aug. 20, 1987;196(4):901-17. doi: 10.1016/0022-2836(87)90412-8.

Cirak et al., Exon skipping and dystrophin restoration in patients with Duchenne muscular dystrophy after systemic phosphorodiamidate morpholino oligomer treatment: an open-label, phase 2, dose-escalation study. Lancet. Aug. 13, 2011;378(9791):595-605. doi: 10.1016/S0140-6736(11)60756-3. Epub Jul. 23, 2011.

Clark et al., Increased brain uptake of targeted nanoparticles by adding an acid-cleavable linkage between transferrin and the nanoparticle core. PNAS. Oct. 2015;112(40):12486-91.

Codelli et al., Second-Generation Difluorinated Cyclooctynes for Copper-Free Click Chemistry. J. Am. Chem. Soc. 2008;130(34):11486-11493. Epub Aug. 5, 2008.

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

Danis et al., Potential therapeutic application of antisense oligonucleotides in the treatment of ocular diseases. Expert Opin Pharmacother. Feb. 2001;2(2):277-91.

Darimont et al., A novel antibody-oligonucleotide conjugate (AOC) platform enables efficient regulation of muscle targets in mice. Abstract. 8-05. J. Cach Sarcopen Musc. 2017; 8: 1065-66.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Desjardins et al., Building a FORCETM platform-based DMD franchise for the treatment of individuals with mutations amenable to exon skipping. Neuromusc Dis. Oct. 2022; 32: S101-2. Abstract.

Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.

Desjardins et al., ForceTM platform achieves robust exon skipping, restores dystrophin at the sarcolemma and halts progression of fibrosis in the severe D2-mdx model of DMD. Abstract. Mar. 2023. 1 page.

Desjardins et al., ForceTM platform achieves robust exon skipping, restores dystrophin at the sarcolemma and halts progression of fibrosis in the severe D2-mdx model of DMD. Poster. Presented at the Muscular Dystrophy Association Clinical and Scientific Conference. Mar. 19-22, 2023. 1 page.

Dommerholt et al., Readily accessible bicyclononynes for bioorthogonal labeling and three-dimensional imaging of living cells. Angew Chem Int Ed. Dec. 3, 2010;49(49):9422-5.

Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.

Echigoya et al., Effects of systemic multiexon skipping with peptide-conjugated morpholinos in the heart of a dog model of Duchenne muscular dystrophy. Proc Natl Acad Sci U S A. Apr. 18, 2017;114(16):4213-4218. doi: 10.1073/pnas.1613203114. Epub Apr. 3, 2017.

Echigoya et al., Exons 45-55 Skipping Using Mutation-Tailored Cocktails of Antisense Morpholinos in the DMD Gene. Mol Ther. Nov. 6, 2019;27(11):2005-2017. doi: 10.1016/j.ymthe.2019.07.012. Epub Jul. 26, 2019.

Echigoya et al., Quantitative Antisense Screening and Optimization for Exon 51 Skipping in Duchenne Muscular Dystrophy. Mol Ther. Nov. 1, 2017;25(11):2561-2572. doi: 10.1016/j.ymthe.2017.07.014. Epub Jul. 28, 2017.

Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.

Elangkovan et al., Gene Therapy for Duchenne Muscular Dystrophy. J Neuromuscul Dis. 2021;8(s2):S303-S316.

Fletcher et al., Morpholino oligomer-mediated exon skipping averts the onset of dystrophic pathology in the mdx mouse. Mol Ther. Sep. 2007;15(9):1587-92. doi: 10.1038/sj.mt.6300245. Epub Jun. 19, 2007.

Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.

Freed et al., Pharmacology Review(s) for Application No. 206488Orig1s000. Center for Drug Evaluation and Research (CDER). Published May 25, 2016. Accessed from accessdata.fda.gov on May 21, 2021. 97 pages.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Gebski et al., Morpholino antisense oligonucleotide induced dystrophin exon 23 skipping in mdx mouse muscle. Hum Mol Genet. Aug. 1, 2003;12(15):1801-11.

Girones et al. Comparison of the kinetics of cycling of the transferrin receptor in the presence or absence of bound diferric transferrin. Biochem J. Nov. 15, 1989;264(1):35-46.

Goemans et al., Systemic administration of PRO051 in Duchenne's muscular dystrophy. N Engl J Med. Apr. 21, 2011;364(16):1513-22. doi: 10.1056/NEJMoa1011367. Epub Mar. 23, 2011. Erratum in: N Engl J Med. Oct. 6, 2011;365(14):1361.

Gong et al., Simple Method to Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Griggs et al., Prednisone in Duchenne dystrophy. A randomized, controlled trial defining the time course and dose response. Clinical Investigation of Duchenne Dystrophy Group. Arch Neurol. Apr. 1991;48(4):383-8. doi: 10.1001/archneur.1991.00530160047012.

(56) References Cited

OTHER PUBLICATIONS

Guirguis et al., Disease-drug interaction: Reduced response to propranolol despite increased concentration in the rat with inflammation. J Pharm Sci. May 2003;92(5):1077-84. Abstract.

Haack et al., Toxic rise of clozapine plasma concentrations in relation to inflammation. Eur Neuropsychopharmacol. Oct. 2003;13(5):381-5.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.

Henry et al., Chemically modified oligonucleotides exhibit decreased immune stimulation in mice. J Pharmacol Exp Ther. Feb. 2000;292(2):468-79.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.

Jirka et al., Cyclic Peptides to Improve Delivery and Exon Skipping of Antisense Oligonucleotides in a Mouse Model for Duchenne Muscular Dystrophy. Mol Ther. Jan. 3, 2018;26(1):132-147. doi: 10.1016/j.ymthe.2017.10.004. Epub Oct. 12, 2017.

Juliano, The delivery of therapeutic oligonucleotides. Nucleic Acids Res. Aug. 19, 2016;44(14):6518-48. doi: 10.1093/nar/gkw236. Epub Apr. 15, 2016.

Khan, Corticosteroid therapy in Duchenne muscular dystrophy. J Neurol Sci. Dec. 1, 1993;120(1):8-14.

Kinali et al., Local restoration of dystrophin expression with the morpholino oligomer AVI-4658 in Duchenne muscular dystrophy: a single-blind, placebo-controlled, dose-escalation, proof-of-concept study. Lancet Neurol. Oct. 2009;8(10):918-28. doi: 10.1016/S1474-4422(09)70211-X. Epub Aug. 25, 2009. Erratum in: Lancet Neurol. Dec. 2009;8(12):1083.

Kline et al., Methods to Make Homogenous Antibody Drug Conjugates. Pharm Res. Nov. 2015;32(11):3480-93. Epub Dec. 16, 2014.

Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Lawrence et al., Crystal structure of the ectodomain of human transferrin receptor. Science. Oct. 22, 1999;286(5440):779-82. doi: 10.1126/science.286.5440.779.

Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Levin, Targeting Therapeutic Oligonucleotides. N Engl J Med. Jan. 5, 2017;376(1):86-88. doi: 10.1056/NEJMcibr1613559.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Lu et al., Functional amounts of dystrophin produced by skipping the mutated exon in the mdx dystrophic mouse. Nat Med. Aug. 2003;9(8):1009-14. Epub Jul. 6, 2003.

Lu et al., Systemic delivery of antisense oligoribonucleotide restores dystrophin expression in body-wide skeletal muscles. Proc Natl Acad Sci U S A. Jan. 4, 2005;102(1):198-203. doi: 10.1073/pnas.0406700102. Epub Dec. 17, 2004.

Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.

Mann et al., Antisense-induced exon skipping and synthesis of dystrophin in the mdx mouse. Proc Natl Acad Sci U S A. Jan. 2, 2001;98(1):42-7.

Manzur et al., Update on the management of Duchenne muscular dystrophy. Arch Dis Child. Nov. 2008;93(11):986-90. doi: 10.1136/adc.2007.118141. Epub Jul. 30, 2008.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mojsov et al., A Quantitative Evaluation of Methods for Coupling Asparagine. The Journal of Organic Chemistry. Feb. 1980;45(4):555-60.

Naylor et al., DELIVER, a randomized, double-blind, placebo controlled, multiple ascending dose study of DYNE-251 in boys with DMD amenable to Exon 51 skipping. Poster. Presented at the Muscular Dystrophy Association Clinical and Scientific Conference. Mar. 19-22, 2023. 1 page.

Naylor et al., DELIVER, a randomized, double-blind, placebo controlled, multiple ascending dose study of DYNE-251 in boys with DMD amenable to Exon 51 skipping. Abstract. Mar. 2023. 1 page.

Nguyen et al., Antisense oligonucleotides for the treatment of cardiomyopathy in Duchenne muscular dystrophy. Am J Transl Res. Mar. 15, 2019;11(3):1202-1218.

Novak et al., Myoblasts and macrophages are required for therapeutic morpholino antisense oligonucleotide delivery to dystrophic muscle. Nat Commun. Oct. 16, 2017;8(1):941. doi: 10.1038/s41467-017-00924-7. Erratum in: Nat Commun. Jan. 15, 2018;9(1):208. Erratum in: Nat Commun. Mar. 23, 2018;9(1):1256.

Nowak et al., Duchenne muscular dystrophy and dystrophin: pathogenesis and opportunities for treatment. EMBO Rep. Sep. 2004;5(9):872-6.

Padlan et al., A possible procedure for reducing the immunogenicity of antibody variable domains while preserving their ligand-binding properties. Molecular Immunology. Apr.-May 1991;28(4-5):489-98.

Panowski et al., Site-specific antibody drug conjugates for cancer therapy. MAbs. Jan.-Feb. 2014;6(1):34-45.

Picariello et al., Dyne-101 achieves durable knockdown of toxic human nuclear DMPK RNA and correction of splicing in the hTfR1/DMSXL mouse model of DM1. Presented at the Muscular Dystrophy Association Clinical and Scientific Conference. Mar. 13-16, 2022. 1 page.

Pradeepkumar, Chemically modified oligonucleotides: synthesis, physicochemical and biochemical properties of their duplexes with DNA and RNA. Comprehensive Summaries of Uppsala Dissertations from the Faculty of Science and Technology. 2004; 973: 56 pages.

Pradhan et al., Prednisolone in Duchenne muscular dystrophy with imminent loss of ambulation. J Neurol. Oct. 2006;253(10):1309-16. doi: 10.1007/s00415-006-0212-1. Epub Jun. 19, 2006.

(56) References Cited

OTHER PUBLICATIONS

Qian et al., Targeted drug delivery via the transferrin receptor-mediated endocytosis pathway. Pharmacol Rev. Dec. 2002;54(4):561-87. doi: 10.1124/pr.54.4.561.

Rando et al., Rescue of dystrophin expression in mdx mouse muscle by RNA/DNA oligonucleotides. Proc Natl Acad Sci U S A. May 9, 2000;97(10):5363-8. doi: 10.1073/pnas.97.10.5363.

Roberts et al., Advances in oligonucleotide drug delivery. Nat Rev Drug Discov. Oct. 2020;19(10):673-694. doi: 10.1038/s41573-020-0075-7. Epub Aug. 11, 2020.

Roberts et al., The Halogenation of Ethylenes. J. Am. Chem. Soc. May 1937;59(5):947-8.

Sahenk et al., The muscular dystrophies: distinct pathogenic mechanisms invite novel therapeutic approaches. Curr Rheumatol Rep. Jun. 2011;13(3):199-207.

Saito et al., Antisense PMO found in dystrophic dog model was effective in cells from exon 7-deleted DMD patient. PLoS One. Aug. 18, 2010;5(8):e12239.

Sazani et al., Safety pharmacology and genotoxicity evaluation of AVI-4658. Int J Toxicol. Mar.-Apr. 2010;29(2):143-56. doi: 10.1177/1091581809359206. Epub Jan. 28, 2010.

Schnyder et al., Targeting of skeletal muscle in vitro using biotinylated immunoliposomes. Biochem J. Jan. 1, 2004;377(Pt 1):61-7. doi: 10.1042/BJ20031034.

Setten et al., The current state and future directions of RNAi-based therapeutics. Nat Rev Drug Discov. Jun. 2019;18(6):421-446. doi: 10.1038/s41573-019-0017-4.

Shen et al., Chemistry, mechanism and clinical status of antisense oligonucleotides and duplex RNAs. Nucleic Acids Res. Feb. 28, 2018;46(4):1584-1600.

Shimizu-Motohashi et al., Exon skipping for Duchenne muscular dystrophy: a systematic review and meta-analysis. Orphanet J Rare Dis. Jun. 15, 2018;13(1):93.

Singh et al., Catalytic Enantioselective Cyclopropanation of Olefins Using Carbenoid Chemistry. Synthesis. Feb. 1997;137-49.

Sklar et al., Methylprednisolone increases dystrophin levels by inhibiting myotube death during myogenesis of normal human muscle in vitro. J Neurol Sci. Jan. 1991;101(1):73-81. doi: 10.1016/0022-510x(91)90019-4.

Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.

Subramanian et al., Abstract 1074. Targeted delivery of oligonucleotide therapeutics to muscle demonstrates potential to treat duchenne muscular dystrophy. Abstract. Mol Ther. 28(4S1): 465. (2020) 1 page.

Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.

Summerton et al..Morpholino antisense oligomers: design, preparation, and properties. Antisense Nucleic Acid Drug Dev. Jun. 1997;7(3):187-95.

Swayze et al., The medicinal chemistry of oligonucleotides. In: Antisense Drug Technology, Second Edition. 2007. Crooke, Ed. Chapter 6: 143-182.

Trollet et al., Gene therapy for muscular dystrophy: current progress and future prospects. Expert Opin Biol Ther. Jul. 2009;9(7):849-66.

Tron et al., Click chemistry reactions in medicinal chemistry: applications of the 1,3-dipolar cycloaddition between azides and alkynes. Med Res Rev. Mar. 2008;28(2):278-308.

Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.

Van Den Bergen et al., Forty-Five Years of Duchenne Muscular Dystrophy in the Netherlands. J Neuromuscul Dis. 2014;1(1):99-109.

Van Deutekom et al., Local dystrophin restoration with antisense oligonucleotide PRO051. N Engl J Med. Dec. 27, 2007;357(26):2677-86. doi: 10.1056/NEJMoa073108.

Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.

Wagner et al., Transferrin-polycation conjugates as carriers for DNA uptake into cells. Proc Natl Acad Sci U S A. May 1990;87(9):3410-4. doi: 10.1073/pnas.87.9.3410.

Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.

Walles et al., ADME and Safety Aspects of Non-cleavable Linkers in Drug Discovery and Development. Curr Top Med Chem. 2017;17(32):3463-3475. doi: 10.2174/1568026618666180118153502.

Wilton et al., Antisense oligonucleotide-induced exon skipping across the human dystrophin gene transcript. Mol Ther. Jul. 2007;15(7):1288-96. doi: 10.1038/sj.mt.6300095. Epub Feb. 6, 2007.

Wilton et al., Antisense oligonucleotides, exon skipping and the dystrophin gene transcript. Acta Myol. Dec. 2005;24(3):222-9.

Wilton et al., Exon skipping and Duchenne muscular dystrophy: hope, hype and how feasible? Neurol India. Jul.-Sep. 2008;56(3):254-62. doi: 10.4103/0028-3886.43443.

Wolf et al., ACHIEVE trial, a randomized, placebo-controlled, multiple ascending dose study of Dyne-101 in individuals with myotonic dystrophy Type 1 (DM1). Abstract. Mar. 2023 1 page.

Wolf et al., ACHIEVE trial, a randomized, placebo-controlled, multiple ascending dose study of Dyne-101 in individuals with myotonic dystrophy Type 1 (DM1). Presented at the Muscular Dystrophy Association Clinical and Scientific Conference. Poster. Mar. 19-22, 2023. 1 page.

Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.

Yao et al., Targeted delivery of ASOs demonstrates potential to treat duchenne muscular dystrophy. Presented at American Society of Gene and Cell Therapy Conference (virtual). May 2020. 1 page.

Ye et al., Generation and functional characterization of the anti-transferrin receptor single-chain antibody-GAL4 (TfRscFv-GAL4) fusion protein. BMC Biotechnol. Nov. 28, 2012;12:91.

Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.

Zanotti et al., Abstract 17. Repeat dosing with DYNE-101 is Well Tolerated and Leads to a Sustained Reduction of DMPK RNA expression in key muscles for DM1 pathology in hTfR1/DMSXL mice and NHPs. Abstract. Mol Ther. Apr. 2022; 30(4S1): 9.

Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.

Zanotti et al., Abstract 82. The ForceTM platform delivers oligonucleotides to the brain in a DM1 mouse model and in NHPs. Mol Ther. Apr. 2023; 31(4S1): 44.

Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.

Zanotti et al., DYNE-101 achieves durable knockdown of toxic human nuclear DMPK RNA and correction of splicing in the hTfR1/DMSXL mouse model of DM1. Abstract. Mar. 2022. 1 page.

Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.

Zanotti, Repeat dosing with DYNE-101 is Well Tolerated and Leads to a Sustained Reduction of DMPKA RNA expression in key muscles for DM1 pathology in hTfR1/DMSXL mice and NHPs. Presented at American Society of Gene & Cell Therapy Conference. May 16, 2022. 15 pages.

Zanotti, The ForceTM platform delivers oligonucleotides to the brain in a DM1 mouse model and in NHPs. Presented at American Society of Gene & Cell Therapy Conference. May 17, 2023. 16 pages.

(56) References Cited

OTHER PUBLICATIONS

Altshuler et al., Generation of recombinant antibodies and means for increasing their affinity. Biochemistry (Mosc). Dec. 2010;75(13):1584-605.
Brown et al., Tolerance of single, but not multiple, amino acid replacements in antibody VH CDR2: a means of minimizing B cell wastage from somatic hypermutation? J Immunol. May 1, 1996;156(9):3285-91.
Chen et al., In-depth structural characterization of Kadcyla® (ado-trastuzumab emtansine) and its biosimilar candidate. MAbs. Oct. 2016;8(7):1210-1223. doi: 10.1080/19420862.2016.1204502. Epub Jul. 5, 2016.
Coico et al., Immunology: A short course. 2008 (originally published 2003): 61-2. 8 pages (including English translation).
Gray et al., Combinatorial peptide libraries: mining for cell-binding peptides. Chem Rev. Jan. 22, 2014;114(2):1020-81.
Murray et al., Human Biochemistry. "Mir." Moscow. 1993; 1:34. 5 pages (including English translation).
Samoylova et al., Elucidation of muscle-binding peptides by phage display screening. Muscle Nerve. Apr. 1999;22(4):460-6.
Schneider et al., Structural features of the cell surface receptor for transferrin that is recognized by the monoclonal antibody OKT9. J Biol Chem. Jul. 25, 1982;257(14):8516-22.
U.S. Appl. No. 18/490,905, filed Oct. 20, 2023, Subramanian et al.
U.S. Appl. No. 18/495,086, filed Oct. 26, 2023, Subramanian et al.
U.S. Appl. No. 18/349,631, filed Jul. 10, 2023, Subramanian et al.
U.S. Appl. No. 18/303,506, filed Apr. 19, 2023, Hilderbrand et al.
Egli et al., Re-Engineering RNA Molecules into Therapeutic Agents. Acc Chem Res. Apr. 16, 2019;52(4):1036-1047. doi: 10.1021/acs.accounts.8b00650. Epub Mar. 26, 2019.
U.S. Appl. No. 18/416,981, filed Jan. 19, 2024, Subramanian et al.
U.S. Appl. No. 18/468,580, filed Sep. 15, 2023, Subramanian et al.
U.S. Appl. No. 18/467,851, filed Sep. 15, 2023, Subramanian et al.
U.S. Appl. No. 18/592,695, filed Mar. 1, 2024, Subramanian et al.
U.S. Appl. No. 18/592,729, filed Mar. 1, 2024, Subramanian et al.
U.S. Appl. No. 17/205,139, filed Mar. 18, 2021, Subramanian et al.
U.S. Appl. No. 18/492,894, filed Oct. 24, 2023, Subramanian et al.
U.S. Appl. No. 18/692,415, filed Mar. 15, 2024, Desjardins et al.
U.S. Appl. No. 17/616,870, filed Dec. 6, 2021, Weeden et al.
U.S. Appl. No. 17/791,670, filed Jul. 8, 2022, Subramanian et al.
U.S. Appl. No. 17/769,467, filed Apr. 15, 2022, Subramanian et al.
U.S. Appl. No. 17/796,418, filed Jul. 29, 2022, Subramanian et al.
U.S. Appl. No. 17/796,416, filed Jul. 29, 2022, Subramanian et al.
U.S. Appl. No. 17/791,681, filed Jul. 8, 2022, Subramanian et al.
U.S. Appl. No. 17/791,697, filed Jul. 8, 2022, Subramanian et al.
U.S. Appl. No. 17/791,701, filed Jul. 8, 2022, Subramanian et al.
U.S. Appl. No. 17/791,667, filed Jul. 8, 2022, Subramanian et al.
U.S. Appl. No. 17/794,768, filed Jul. 22, 2022, Subramanian et al.
U.S. Appl. No. 18/017,167, filed Jan. 20, 2023, Subramanian et al.
U.S. Appl. No. 18/017,170, filed Jan. 20, 2023, Subramanian et al.
U.S. Appl. No. 18/017,173, filed Jan. 20, 2023, Subramanian et al.
U.S. Appl. No. 18/017,179, filed Jan. 20, 2023, Subramanian et al.
U.S. Appl. No. 18/017,180, filed Jan. 20, 2023, Subramanian et al.
U.S. Appl. No. 18/017,182, filed Jan. 20, 2023, Subramanian et al.
U.S. Appl. No. 18/024,486, filed Mar. 2, 2023, Weeden et al.
U.S. Appl. No. 18/265,065, filed Jun. 2, 2023, Hilderbrand et al.
U.S. Appl. No. 18/270,324, filed Jun. 29, 2023, Subramanian et al.
U.S. Appl. No. 18/270,284, filed Jun. 29, 2023, Brown et al.
U.S. Appl. No. 18/572,321, filed Dec. 20, 2023, Subramanian et al.
U.S. Appl. No. 18/572,260, filed Dec. 20, 2023, Subramanian et al.
U.S. Appl. No. 18/577,468, filed Jan. 8, 2024, Zanotti et al.
U.S. Appl. No. 18/577,452, filed Jan. 8, 2024, Desjardins et al.
U.S. Appl. No. 18/577,382, filed Jan. 8, 2024, Subramanian et al.
U.S. Appl. No. 18/577,348, filed Jan. 8, 2024, Weeden et al.
U.S. Appl. No. 18/577,378, filed Jan. 8, 2024, Desjardins et al.
U.S. Appl. No. 18/577,462, filed Jan. 8, 2024, Desjardins et al.
U.S. Appl. No. 18/577,374, filed Jan. 8, 2024, Desjardins et al.
U.S. Appl. No. 18/577,472, filed Jan. 8, 2024, Desjardins et al.
U.S. Appl. No. 18/609,032, filed Mar. 19, 2024, Subramanian et al.
U.S. Appl. No. 18/706,057, filed Apr. 30, 2024, Subramanian et al.
U.S. Appl. No. 18/651,734, filed May 1, 2024, Subramanian et al.
U.S. Appl. No. 18/656,654, filed May 7, 2024, Subramanian et al.
U.S. Appl. No. 18/656,672, filed May 7, 2024, Subramanian et al.
U.S. Appl. No. 18/708,815, filed May 9, 2024, Hsia et al.
U.S. Appl. No. 18/436,078, filed Feb. 8, 2024, Hilderbrand et al.
U.S. Appl. No. 18/349,084, filed Jul. 7, 2023, McNeill et al.
U.S. Appl. No. 17/811,332, filed Jul. 8, 2022, Subramanian et al.

* cited by examiner

| Injection Name | % HMWS 1 | % Dimer | % Total HMWS | % Peak 1 | % Peak 2 | % Peak 3 | % LMWS | % Free Oligo |
|---|---|---|---|---|---|---|---|---|
| 10 mg/mL Glass Standard | n.a. | 7.8 | 7.8 | 26 | 40 | 23.8 | 1.2 | 1.1 |
| 25 mg/mL Glass | n.a. | 7.8 | 7.9 | 25.9 | 40.1 | 23.8 | 1.2 | 1.1 |
| 25 mg/mL EVA | n.a. | 7.8 | 7.9 | 26 | 40.1 | 23.8 | 1.2 | 1.1 |
| 25 mg/mL HDPE | n.a. | 7.8 | 7.8 | 26.1 | 39.9 | 23.9 | 1.2 | 1.1 |
| 25 mg/mL PC | n.a. | 7.8 | 7.9 | 26.1 | 39.9 | 23.8 | 1.2 | 1.1 |

FIG. 4

MUSCLE TARGETING COMPLEXES AND FORMULATIONS FOR TREATING DYSTROPHINOPATHIES

RELATED APPLICATIONS

This application is a continuation of International Patent Application No. PCT/US2022/073540, filed Jul. 8, 2022, entitled "MUSCLE TARGETING COMPLEXES AND FORMULATIONS FOR TREATING DYSTROPHINOPATHIES", which claims the benefit under 35 U.S.C § 119(e) of the filing date of U.S. Provisional Application No. 63/220,426, entitled "MUSCLE TARGETING COMPLEXES AND FORMULATIONS FOR TREATING DYSTROPHINOPATHIES", filed Jul. 9, 2021, the contents of which are incorporated herein by reference in their entirety.

FIELD OF THE INVENTION

The present application relates to targeting complexes for delivering oligonucleotide molecular payloads to cells, formulations comprising such complexes, and uses thereof, particularly uses relating to treatment of disease.

REFERENCE TO AN ELECTRONIC SEQUENCE LISTING

The contents of the electronic sequence listing (D082470061US01-SEQ-CBD.xml; Size: 55,585 bytes; and Date of Creation: Aug. 10, 2023) is herein incorporated by reference in its entirety.

BACKGROUND OF INVENTION

Dystrophinopathies are a group of distinct neuromuscular diseases that result from mutations in DMD gene. Dystrophinopathies include Duchenne muscular dystrophy, Becker muscular dystrophy, and X-linked dilated cardiomyopathy. The DMD, which encodes dystrophin, is a large gene, containing 79 exons and approximately 2.6 million total base pairs. Numerous mutations in DMD, including exonic frameshift, deletion, substitution, and duplicative mutations, are able to diminish the expression of functional dystrophin, leading to dystrophinopathies.

SUMMARY OF INVENTION

According to some aspects, the present disclosure provides complexes and formulations comprising such complexes. In some embodiments, complexes provided herein are formulated with histidine (e.g., L-histidine) and sucrose. In some embodiments, complexes provided herein are formulated as aqueous or lyophilized (e.g., lyophilized powder) forms. In some embodiments, complexes provided herein are formulated as frozen forms. In some embodiments, complexes provided herein comprise a phosphorodiamidate morpholino oligomer (PMO) covalently linked to an antibody. In some embodiments, complexes provided herein comprise a muscle-targeting complex comprising a PMO covalently linked to an anti-transferrin receptor 1 (TfR1) antibody. In some embodiments, the anti-TfR1 antibody has undergone pyroglutamate formation resulting from a post-translational modification. In some embodiments, a complex comprises a muscle-targeting complex comprising a PMO covalently linked to the anti-transferrin receptor 1 (TfR1) antibody, e.g., having a sequence as set forth in Table 2. In some embodiments, the PMO targets a DMD allele (e.g., a mutated DMD allele). Also provided are methods of using the complexes and formulations described herein for treating a subject having a mutated DMD allele associated with Duchenne Muscular Dystrophy (e.g., wherein the mutated DMD allele comprises a mutation amenable to exon skipping) and/or methods of promoting the expression or activity of a dystrophin protein (e.g., a truncated dystrophin protein) in a cell (e.g., a muscle cell).

Some aspects of the present disclosure provide formulations comprising complexes that comprise a phosphorodiamidate morpholino oligomer (PMO) covalently linked to an anti-transferrin receptor 1 (TfR1) antibody, wherein the antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16, and wherein the complexes are formulated with histidine and sucrose.

Some aspects of the present disclosure provide formulations comprising complexes comprising a structure of formula: $[R^1]_{n1}-R^2$, wherein each $R^1$ independently comprises a group of the formula (Ia):

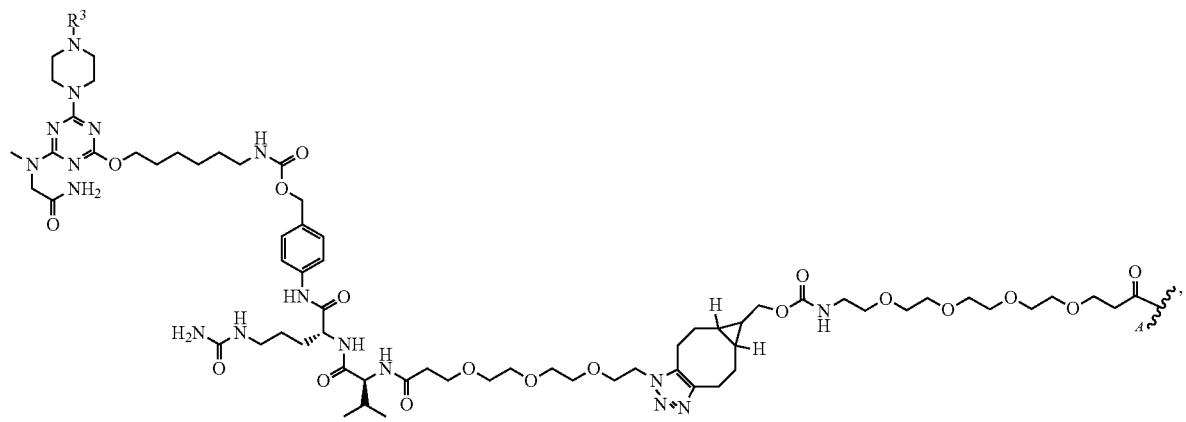

(Ia)

wherein:

R² comprises an antibody, and

R³ comprises a phosphorodiamidate morpholino oligomer (PMO);

wherein R¹ is covalently linked to R² at attachment point A; and wherein n1 is an integer of one or greater representing the number of instances of R¹, wherein each instance of R¹ is covalently linked to a different amino acid residue of the antibody;

wherein the complexes are formulated with histidine and sucrose.

In some embodiments, each different amino acid residue is a lysine.

In some embodiments, the antibody is an anti-TfR1 antibody.

In some embodiments, the average value of n1 of complexes in the formulation is in the range of 1 to 5.

In some embodiments, the antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16.

In some embodiments, the formulation is in a lyophilized form, an aqueous solution, or a frozen solid form.

In some embodiments, the formulation is in an aqueous solution and the histidine is present in the aqueous solution at a concentration in the range of 10 mM to 50 mM.

In some embodiments, the formulation is in an aqueous solution and the sucrose is present in the aqueous solution at a concentration in the range of 5% to 15% weight per volume (w/v %).

In some embodiments, the formulation is in an aqueous solution and the aqueous solution has a pH in the range of 5.0 to 7.0.

In some embodiments, the formulation is in an aqueous solution and the histidine is present in the aqueous solution at a concentration of 25 mM and/or the sucrose is present in the aqueous solution at a concentration of 10 w/v % and/or the aqueous solution is at a pH of 6.0.

In some embodiments, the antibody is a Fab fragment, a full-length IgG, a Fab' fragment, a F(ab')₂ fragment, an scFv, or an Fv.

In some embodiments, the antibody is a Fab fragment.

In some embodiments, the antibody comprises a heavy chain variable region (VH) comprising an amino acid sequence at least 85% identical to SEQ ID NO: 17; and/or wherein the antibody comprises a light chain variable region (VL) comprising an amino acid sequence at least 85% identical to SEQ ID NO: 18.

In some embodiments, the antibody comprises a VH comprising the amino acid sequence of SEQ ID NO: 17 and a VL comprising the amino acid sequence of SEQ ID NO: 18.

In some embodiments, the antibody comprises a heavy chain comprising an amino acid sequence at least 85% identical to SEQ ID NO: 19; and/or wherein the antibody comprises a light chain comprising an amino acid sequence at least 85% identical to SEQ ID NO: 20.

In some embodiments, the antibody comprises a heavy chain comprising the amino acid sequence of SEQ ID NO: 19 and a light chain comprising the amino acid sequence of SEQ ID NO: 20.

In some embodiments, the PMO comprises a nucleobase sequence that is 15-35 nucleotides in length.

In some embodiments, the PMO comprises a nucleotide sequence having a region of complementarity of at least 8 consecutive nucleotides in length to SEQ ID NO: 23, to SEQ ID NO: 24, or to SEQ ID NO: 22.

In some embodiments, the PMO comprises at least 8 consecutive nucleotides of a nucleotide sequence as set forth in SEQ ID NO: 21.

In some embodiments, the PMO comprises the nucleotide sequence of SEQ ID NO: 21.

In some embodiments, each R¹ comprises a group of the formula (Ib):

(Ib)

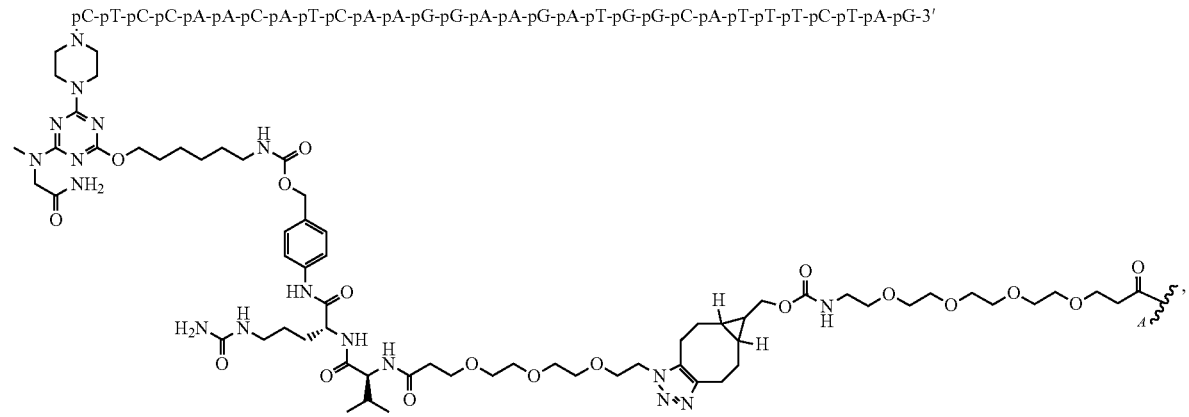

in which -pN indicates a base position of a phosphorodiamidate morpholino oligomer (PMO), wherein -p reflects a phosphorodiamidate linkage, wherein N corresponds to a nucleobase of adenine (A), cytosine (C), guanine (G), or thymine (T), such that the PMO has a nucleobase sequence of CTCCAACATCAAGGAAGATGGCATTTCTAG (SEQ ID NO: 21), and wherein $R^1$ is covalently linked to $R^2$ at attachment point A.

In some embodiments, each $R^1$ comprises a group of the formula (Ic):

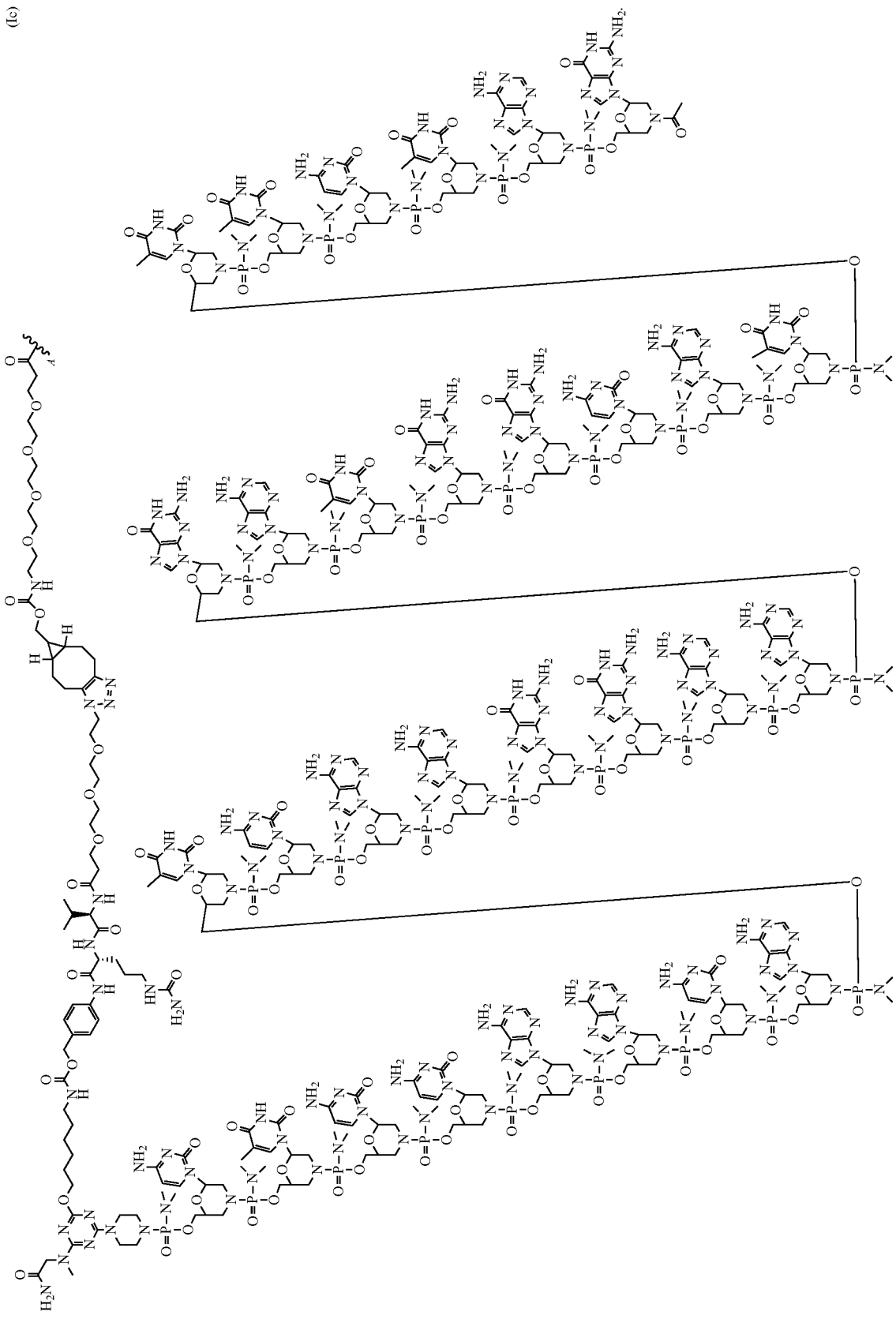

In some embodiments, the complexes are present in the formulation at a concentration in the range of 10 mg/mL to 50 mg/mL.

Further provided herein are methods of promoting expression or activity of a dystrophin protein in a subject, the method comprising administering to the subject the formulation described herein.

In some embodiments, the dystrophin protein is a truncated dystrophin protein.

Further provided herein are methods of treating a subject having a mutated DMD allele associated with Duchenne Muscular Dystrophy, the method comprising administering to the subject the formulation described herein.

In some embodiments, the mutated DMD allele comprises a mutation amenable to exon 51 skipping.

In some embodiments, the mutated DMD allele comprises a frameshift mutation in exon 51.

Other aspects of the present disclosure provide complexes comprising a structure of formula (I): $[R^1]_{n1}$—$R^2$, wherein each $R^1$ comprises a group of the formula (Ia):

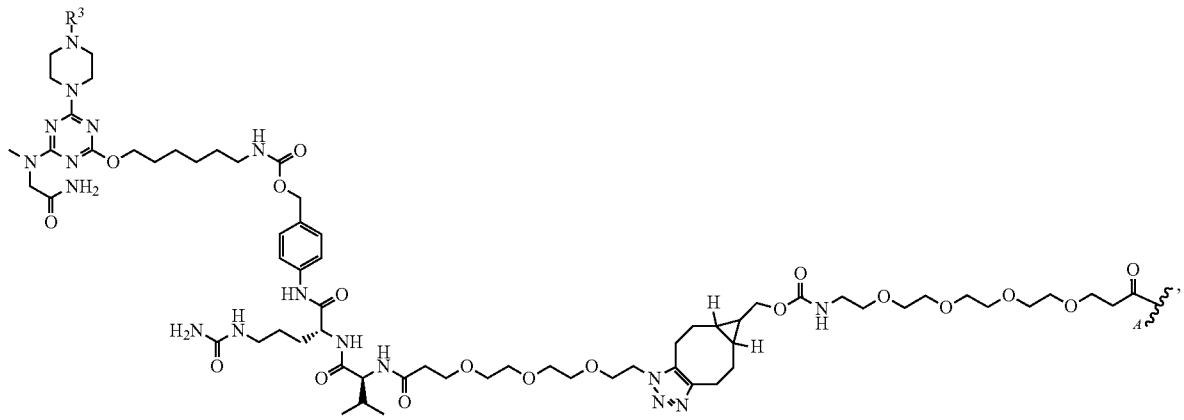

(Ia)

wherein $R^3$ comprises a phosphorodiamidate morpholino oligomer (PMO) comprising the base sequence of CTCCAACATCAAGGAAGATGGCATTTCTAG (SEQ ID NO: 21);

wherein $R^2$ comprises a Fab, and wherein the Fab comprises a CDR-H1, a CDR-H2, a CDR-H3, a CDR-L1, a CDR-L2, and a CDR-L3 selected from Table 2, wherein $R^1$ is covalently linked to $R^2$ at attachment point A; and wherein n1 is independently an integer of one or greater representing the number of instances of $R^1$ in each complex, wherein each instance of $R^1$ is covalently linked to a different amino acid residue of the Fab.

In some embodiments, the Fab comprises a VH comprising the amino acid sequence of SEQ ID NO: 17 and a VL comprising the amino acid sequence of SEQ ID NO: 18, In some embodiments, the Fab comprises a heavy chain comprising the amino acid sequence of SEQ ID NO: 19 and a light chain comprising the amino acid sequence of SEQ ID NO: 20.

In some embodiments, each different amino acid residue is a lysine.

Other aspects of the present disclosure provide complexes comprising a structure of formula (I): $[R^1]_{n1}$—$R^2$, wherein each $R^1$ comprises a group of the formula (Ib):

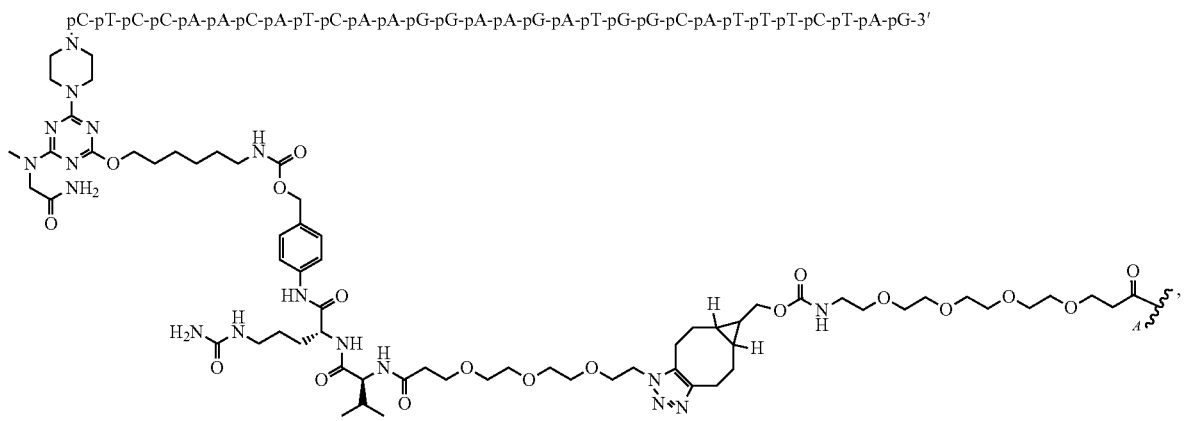

(Ib)

wherein $R^2$ comprises a Fab, and wherein the Fab comprises a CDR-H1, a CDR-H2, a CDR-H3, a CDR-L1, a CDR-L2, and a CDR-L3 selected from Table 2, wherein -pN indicates a base position of a phosphorodiamidate morpholino oligomer (PMO), wherein -p reflects a phosphorodiamidate linkage, and wherein N corresponds to a nucleobase of adenine (A), cytosine (C), guanine (G), or thymine (T), such that the oligonucleotide PMO has a nucleobase sequence of CTC-CAACATCAAGGAAGATGGCATTTCTAG (SEQ ID NO: 21);
wherein $R^1$ is covalently linked to $R^2$ at attachment point A; and wherein n1 is an integer of one or greater representing the number of instances of $R^1$, wherein each instance of $R^1$ is covalently linked to a different amino acid residue of the Fab.

In some embodiments, the Fab comprises a VH comprising the amino acid sequence of SEQ ID NO: 17 and a VL comprising the amino acid sequence of SEQ ID NO: 18, In some embodiments, the Fab comprises a heavy chain comprising the amino acid sequence of SEQ ID NO: 19 and a light chain comprising the amino acid sequence of SEQ ID NO: 20, In some embodiments, each different amino acid residue is a lysine.

Other aspects of the present disclosure provide complexes comprising a structure of formula (I): $[R^1]_1$n-$R^2$, wherein each $R^1$ comprises a group of the formula (Ic):

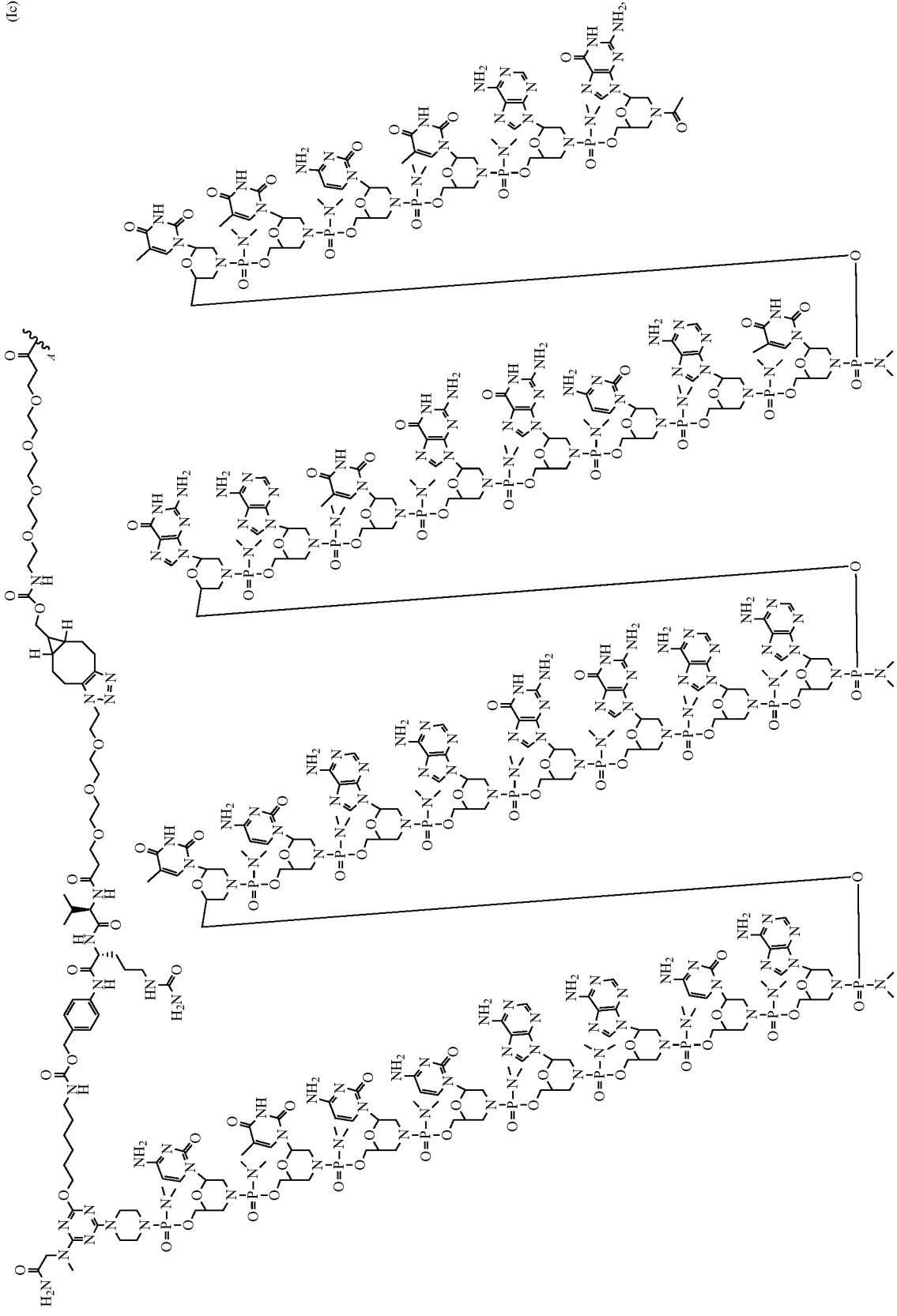
(1c)

wherein R² comprises a Fab comprising a CDR-H1, a CDR-H2, a CDR-H3, a CDR-L1, a CDR-L2, and a CDR-L3 selected from Table 2;

wherein R¹ is covalently linked to R² at attachment point A; wherein n1 is an integer of one or greater representing the number of N instances of R, wherein each instance of R¹ is covalently linked to a different amino acid residue of the Fab.

In some embodiments, R² comprises a Fab comprising a VH comprising the amino acid sequence of SEQ ID NO: 17 and a VL comprising the amino acid sequence of SEQ ID NO: 18.

In some embodiments, R² comprises a Fab comprising a heavy chain comprising the amino acid sequence of SEQ ID NO: 19 and a light chain comprising the amino acid sequence of SEQ ID NO: 20.

In some embodiments, each different amino acid residue is a lysine.

Other aspects of the present disclosure provide complexes comprising a structure of formula (Id):

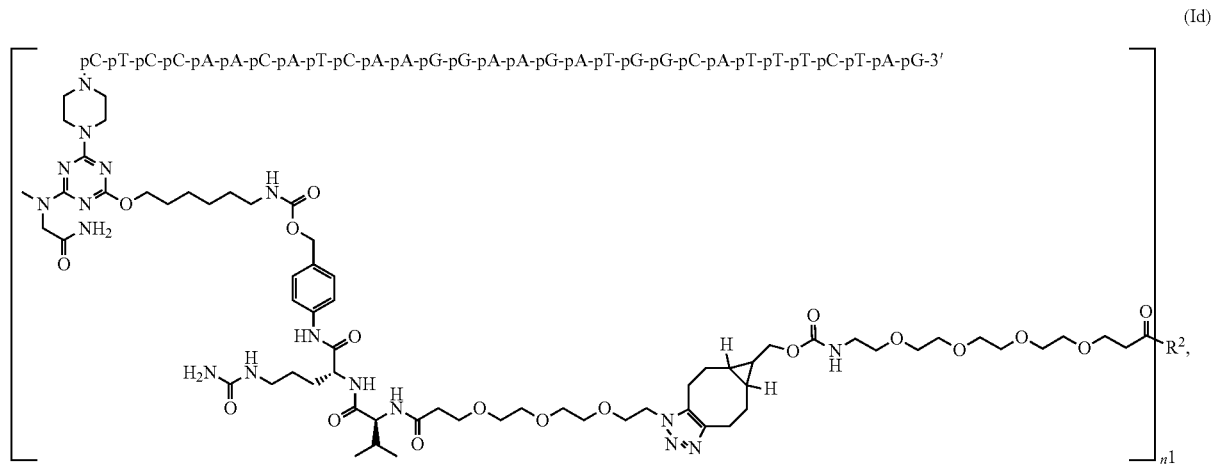

(Id)

wherein R² comprises a Fab comprising a CDR-H1, a CDR-H2, a CDR-H3, a CDR-L1, a CDR-L2, and a CDR-L3 selected from Table 2;

wherein -pN indicates a base position of a phosphorodiamidate morpholino oligomer (PMO); wherein -p reflects a phosphorodiamidate linkage, and wherein N corresponds to a nucleobase of adenine (A), cytosine (C), guanine (G), or thymine (T), such that the PMO comprises a base sequence of CTCCAACATCAAGGAAGATGGCATTTCTAG (SEQ ID NO: 21);

wherein R¹ is covalently linked to R² at attachment point A; wherein n1 is an integer of one or greater representing the number of instances of R¹, wherein each instance of R¹ is covalently linked to a different amino acid residue of the Fab.

In some embodiments, R² comprises a Fab comprising a VH comprising the amino acid sequence of SEQ ID NO: 17 and a VL comprising the amino acid sequence of SEQ ID NO: 18.

In some embodiments, R² comprises a Fab comprising a heavy chain comprising the amino acid sequence of SEQ ID NO: 19 and a light chain comprising the amino acid sequence of SEQ ID NO: 20.

In some embodiments, each different amino acid residue is a lysine.

BRIEF DESCRIPTION OF THE DRAWINGS

FIG. 4 shows the SEC-HPLC results of Formulation 1 comprising the anti-TfR1 Fab having the VH/VL sequences shown in Table 2 covalently linked (through lysine conjugation) via a linker comprising a valine-citrulline sequence to a DMD exon 51-skipping ASO ("anti-TfR1 Fab-ASO conjugate"). There were no material changes in the composition of the peaks across all of the sample formulations. HMWS 1 refers to high molecular weight standard 1 and LMWS 1 refers to low molecular weight standard 1.

DETAILED DESCRIPTION OF INVENTION

Figure 1:
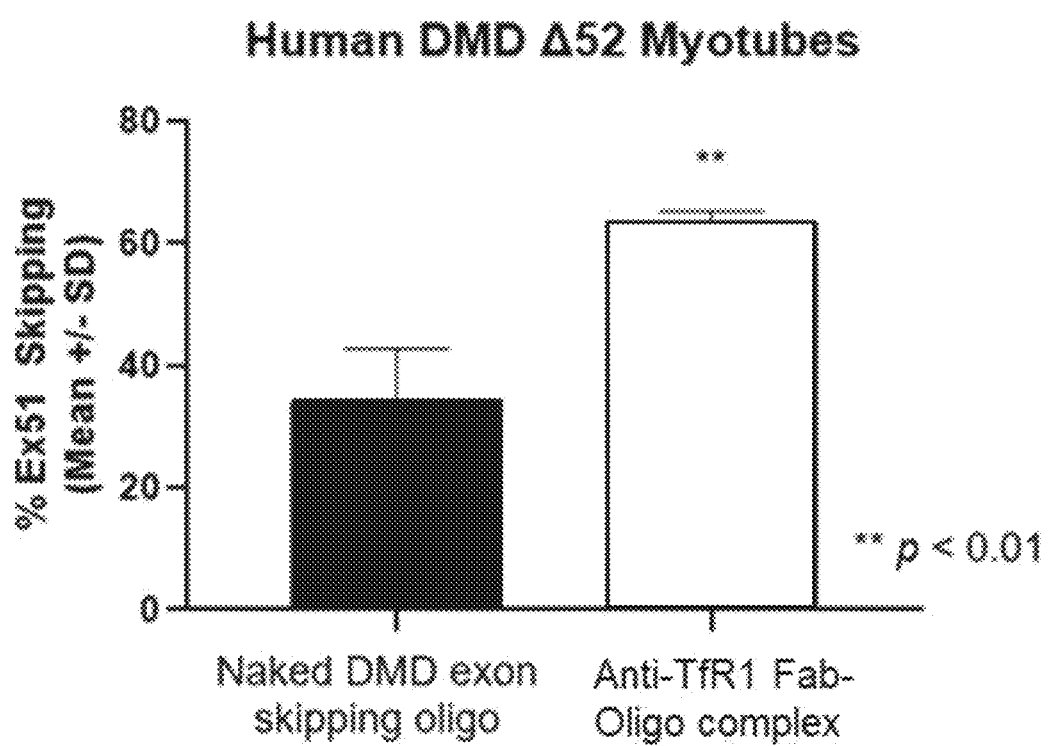
FIG. 1 shows data illustrating that a composition comprising conjugates comprising an anti-TfR1 Fab having the VH/VL sequences shown in Table 2, in which the Fab is covalently linked (through lysine conjugation) via a linker comprising a valine-citrulline sequence to a DMD exon-skipping oligonucleotide resulted in enhanced exon skipping compared to the naked DMD exon skipping oligo in Duchenne Muscular Dystrophy patient myotubes at a matched equimolar dose of oligonucleotide.

According to some aspects, the present disclosure provides complexes and formulations comprising such complexes. In some embodiments, the complexes are formulated with histidine (e.g., L-histidine) and sucrose. In some embodiments, the complexes are formulated as aqueous or lyophilized (e.g., lyophilized powder) forms. In some embodiments, a complex comprises a phosphorodiamidate morpholino oligomer (PMO) covalently linked to an antibody. In some embodiments, a complex comprises a muscle-targeting complex comprising a PMO covalently linked to an anti-transferrin receptor 1 (TfR1) antibody. In some embodiments, a complex comprises a muscle-targeting complex comprising a PMO covalently linked to the anti-transferrin receptor 1 (TfR1) antibody shown in Table 2. Also provided are methods of using the complexes and formulations described herein for treating a subject having a mutated DMD allele associated with Duchenne Muscular Dystrophy (e.g., wherein the mutated DMD allele comprises a mutation amenable to exon skipping) and/or methods of promoting the expression or activity of a dystrophin protein (e.g., a truncated dystrophin protein) in a cell.

Further aspects of the disclosure, including a description of defined terms, are provided below.

Definitions

Administering: As used herein, the terms "administering" or "administration" means to provide a complex to a subject in a manner that is physiologically and/or (e.g., and) pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a Fab' fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or (e.g., and) a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (a), delta (A), epsilon (ε), gamma (γ) or mu (μ) heavy chain. In a particular embodiment, an antibody described herein comprises a human gamma 1 CH1, CH2, and/or (e.g., and) CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or (e.g., and) methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or (e.g., and) phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. A typical antibody molecule comprises a heavy chain variable region (VH) and a light chain variable region (VL), which are usually involved in antigen binding. The VH and VL regions can be further subdivided into regions of hypervariability, also known as "complementarity determining regions" ("CDR"), interspersed with regions that are more conserved, which are known as "framework regions" ("FR"). Each VH and VL is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the IMGT definition, the Chothia definition, the AbM definition, and/or (e.g., and) the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; IMGT®, the international ImMunoGeneTics information System® imgt.org, Lefranc, M.-P. et al., Nucleic Acids Res., 27:209-212 (1999); Ruiz, M. et al., Nucleic Acids Res., 28:219-221 (2000); Lefranc, M.-P., Nucleic Acids Res., 29:207-209 (2001); Lefranc, M.-P., Nucleic Acids Res., 31:307-310 (2003); Lefranc, M.-P. et al., In Silico Biol., 5, 0006 (2004) [Epub], 5:45-60 (2005); Lefranc, M.-P. et al., Nucleic Acids Res., 33:D593-597 (2005); Lefranc, M.-P. et al., Nucleic Acids Res., 37:D1006-1012 (2009); Lefranc, M.-P. et al., Nucleic Acids Res., 43:D413-422 (2015); Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also bioinf.org.uk/abs. As used herein, a CDR may refer to the CDR defined by any method known in the art. Two antibodies having the same CDR means that the two antibodies have the same amino acid sequence of that CDR as determined by the same method, for example, the IMGT definition.

There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems. Examples of CDR definition systems are provided in Table 1.

TABLE 1

| CDR Definitions | | | |
|---|---|---|---|
| | IMGT[1] | Kabat[2] | Chothia[3] |
| CDR-H1 | 27-38 | 31-35 | 26-32 |
| CDR-H2 | 56-65 | 50-65 | 53-55 |
| CDR-H3 | 105-116/117 | 95-102 | 96-101 |
| CDR-L1 | 27-38 | 24-34 | 26-32 |

TABLE 1-continued

| CDR Definitions | | | |
|---|---|---|---|
| | IMGT[1] | Kabat[2] | Chothia[3] |
| CDR-L2 | 56-65 | 50-56 | 50-52 |
| CDR-L3 | 105-116/117 | 89-97 | 91-96 |

[1]IMGT ®, the international ImMunoGeneTics information system ®, imgt.org, Lefranc, M.-P. et al., Nucleic Acids Res., 27: 209-212 (1999)
[2]Kabat et al. (1991) Sequences of Proteins of Immunological Interest, Fifth Edition, U.S. Department of Health and Human Services, NIH Publication No. 91-3242
[3]Chothia et al., J. Mol. Biol. 196: 901-917 (1987))

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

DMD: As used herein, the term "DMD" refers to a gene that encodes dystrophin protein, a key component of the dystrophin-glycoprotein complex, which bridges the inner cytoskeleton and the extracellular matrix in muscle cells, particularly muscle fibers. Deletions, duplications, and point mutations in DMD may cause dystrophinopathies, such as Duchenne muscular dystrophy, Becker muscular dystrophy, or cardiomyopathy. Alternative promoter usage and alternative splicing result in numerous distinct transcript variants and protein isoforms for this gene. In some embodiments, a DMD gene may be a human (Gene ID: 1756), non-human primate (e.g., Gene ID: 465559), or rodent gene (e.g., Gene ID: 13405; Gene ID: 24907). In addition, multiple human transcript variants (e.g., as annotated under GenBank RefSeq Accession Numbers: NM_000109.3, NM_004006.2 (SEQ ID NO: 24), NM_004009.3, NM_004010.3 and NM_004011.3) have been characterized that encode different protein isoforms.

DMD allele: As used herein, the term "DMD allele" refers to any one of alternative forms (e.g., wild-type or mutant forms) of a DMD gene. In some embodiments, a DMD allele may encode for dystrophin that retains its normal and typical functions. In some embodiments, a DMD allele may comprise one or more mutations that results in muscular dystrophy. Common mutations that lead to Duchenne muscular dystrophy involve frameshift, deletion, substitution, and duplicative mutations of one or more of 79 exons present in a DMD allele, e.g., exon 8, exon 23, exon 41, exon 44, exon 50, exon 51, exon 52, exon 53, or exon 55. Further examples of DMD mutations are disclosed, for example, in Flanigan K M, et al., *Mutational spectrum of DMD mutations in dystrophinopathy patients: application of modern diagnostic techniques to a large cohort*. Hum Mutat. 2009 December; 30 (12):1657-66, the contents of which are incorporated herein by reference in its entirety.

Dystrophinopathy: As used herein, the term "dystrophinopathy" refers to a muscle disease that results from one or more mutated DMD alleles. Dystrophinopathies include a spectrum of conditions (ranging from mild to severe) that includes Duchenne muscular dystrophy, Becker muscular dystrophy, and DMD-associated dilated cardiomyopathy (DCM). In some embodiments, at one end of the spectrum, dystrophinopathy is phenotypically associated with an asymptomatic increase in serum concentration of creatine phosphokinase (CK) and/or (e.g., and) muscle cramps with myoglobinuria. In some embodiments, at the other end of the spectrum, dystrophinopathy is phenotypically associated with progressive muscle diseases that are generally classified as Duchenne or Becker muscular dystrophy when skeletal muscle is primarily affected and as DMD-associated dilated cardiomyopathy (DCM) when the heart is primarily affected. Symptoms of Duchenne muscular dystrophy include muscle loss or degeneration, diminished muscle function, pseudohypertrophy of the tongue and calf muscles, higher risk of neurological abnormalities, and a shortened lifespan. Duchenne muscular dystrophy is associated with Online Mendelian Inheritance in Man (OMIM) Entry #310200. Becker muscular dystrophy is associated with OMIM Entry #300376. Dilated cardiomyopathy is associated with OMIM Entry X #302045.

Exonic splicing enhancer (ESE): As used herein, the term "exonic splicing enhancer" or "ESE" refers to a nucleic acid sequence motif within an exon of a gene, pre-mRNA, or mRNA that directs or enhances splicing of pre-mRNA into mRNA, e.g., as described in Blencowe et al., Trends Biochem Sci 25, 106-10. (2000), incorporated herein by reference. ESEs are splicing features. ESEs may direct or enhance splicing, for example, to remove one or more introns and/or one or more exons from a gene transcript. ESE motifs are typically 6-8 nucleobases in length. SR proteins (e.g., proteins encoded by the gene SRSF1, SRSF2, SRSF3, SRSF4, SRSF5, SRSF6, SRSF7, SRSF8, SRSF9, SRSF10, SRSF11, SRSF12, TRA2A or TRA2B) bind to ESEs through their RNA recognition motif region to facilitate splicing. ESE motifs can be identified through a number of methods, including those described in Cartegni et al., Nucleic Acids Research, 2003, Vol. 31, No. 13, 3568-3571, incorporated herein by reference.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or (e.g., and) VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Morpholinos: As used herein, the term "morpholino", also referred to as a "phosphorodiamidate morpholino oligomer", refers to a molecular structure that contains nucleobases attached to a backbone of methylenemorpholine rings linked through a phosphorodiamidate group. In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidate morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleosides (e.g., 2'-O-methyl sugar modifications, purine or pyrimidine modifications). In some embodiments, an oligonucleotide may comprise one or more modified internucleoside linkage. In some embodiments, an oligonucleotide may comprise one or more phosphorothioate linkages, which may be in the Rp or Sp stereochemical conformation.

Region of complementarity: As used herein, the term "region of complementarity" refers to a nucleotide sequence, e.g., of an oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having a disease resulting from a mutated DMD gene sequence, e.g., a mutation in an exon of a DMD gene sequence. In some embodiments, a subject has a dystrophinopathy, e.g., Duchenne muscular dystrophy.

Transferrin receptor: As used herein, the term, "transferrin receptor" (also known as TFRC, CD71, p90, TFR, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

Ranges: All ranges provided in the present disclosure are inclusive of the end points.

Complexes

Provided herein are complexes that comprise a targeting agent, e.g., an antibody, covalently linked to an oligonucleotide. In some embodiments, a complex comprises a muscle-targeting antibody covalently linked to one or more oligonucleotides. In some embodiments, the oligonucleotide is a PMO. In some embodiments, the oligonucleotide is an oligonucleotide that targets a mutated DMD allele to promote exon skipping.

Complexes described herein generally comprise a linker that covalently links an antibody (e.g., any one of the anti-TfR1 antibodies) described herein to an oligonucleotide (e.g., a PMO). A linker comprises at least one covalent bond.

In some embodiments, complexes provided herein (e.g., in compositions or formulations described herein) comprise a structure of formula (I): $[R^1]_{n1}$—$R^2$, in which each $R^1$ independently comprises a compound comprising an oligonucleotide (e.g., a PMO) and $R^2$ comprises an antibody (e.g., anti-TfR1 antibody), and in which n1 is an integer (e.g., of one or greater) representing the number of instances of $R^1$ in the complex. In some embodiments, in each complex n1 is independently an integer (e.g., of zero or greater) representing the number of instances of $R^1$ in each complex. In some embodiments, each $R^1$ independently comprises a group comprising an oligonucleotide. In some embodiments, each $R^1$ independently comprises a group that comprises additional elements in addition to an oligonucleotide. In some embodiments, $R^2$ comprises an antibody (e.g., anti-TfR1 antibody) comprising a heavy chain comprising a heavy chain variable region (VH) and a heavy chain constant region, and a light chain comprising a light chain variable region (VL) and a light chain constant region. In some embodiments, each $R^1$ of a complex is independently covalently linked to a different amino acid residue (e.g., lysine or cysteine) of $R^2$. In some embodiments, $R^2$ comprises an anti-TfR1 Fab.

In some embodiments, in each complex, n1 is independently an integer of zero or greater. In some embodiments, in each complex, n1 is independently an integer of one or greater. In some embodiments, n1 is an integer of one or greater. In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a F(ab')$_2$ fragment, an scFv, or an Fv. In some embodiments, the antibody is a Fab fragment.

In some embodiments, the value of n1 of each or any complex (e.g., any complex in any of the compositions or formulations disclosed herein) is an integer from one up to the number of amino acid residues in the antibody to which conjugation is desired or targeted (e.g., the number of lysine residues). In some embodiments, the value of n1 is selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 is selected from 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 is in the range of 1-27, 1-26, 1-10, 1-5, or 1-3. In some embodiments, in each complex, the value of n1 is independently selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, in each complex, the value of n1 is independently selected from 1, 2, 3, 4, 5, 6, 7, 8, 9, 10, 11, 12, 13, 14, 15, 16, 17, 18, 19, 20, 21, 22, 23, 24, 25 and 26. In some embodiments, in each complex, the value of n1 is independently in the range of 1-27, 1-26, 1-10, 1-5, or 1-3. In some embodiments, the average value of n1 of complexes of the composition is in the range of 1 to 5 (e.g., 1-5, 1-4, 1-3, 3-5, or 1-2). In some embodiments, compositions described herein comprise complexes that comprise a structure of formula (I): $[R^1]_{n1}$—$R^2$, wherein n1 is 0. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2). In some embodiments, in each complex type n1 is independently an integer of one or greater representing the number of instances of $R^1$ in each complex of the complex type, and in which the different complex types of the composition are characterized by having different n1 values (e.g., n1 values in the range of 1-27, 1-26, 1-25, 1-20, 1-15, 1-10, 1-5, or 1-3).

In some embodiments, compositions are provided (e.g., formulations comprising histidine and/or sucrose, as described herein) that comprise a plurality of different complexes. In some embodiments, the plurality of different complexes comprise a common targeting agent (e.g. an antibody) and a common oligonucleotide (e.g., PMO). In such embodiments, different complex types are characterized by having different numbers of oligonucleotides covalently linked to an antibody. For example, in some embodiments, compositions are provided that comprise a plurality of complex types in which each complex type comprises a structure of formula (I): $[R^1]_{n1}$—$R^2$, in which each $R^1$ independently comprises a compound comprising an oligonucleotide (e.g., a PMO) and $R^2$ comprises an antibody (e.g., anti-TfR1 antibody), and in which in each complex type n1 is independently is an integer of one or greater representing the number of instances of $R^1$ in each complex of the complex type, and in which the different complex types of the composition are characterized by having different n1 values (e.g., n1 values in the range of 1-27, 1-26). In some embodiments, each different complex types of the composition have different n1 values in the range of 1-27, 1-26, 1-25, 1-20, 1-15, 1-10, 1-5, or 1-3. In some embodiments, in complexes of a composition n1 is independently an integer. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2). In some embodiments, compositions described herein comprise complexes in which n1 is 0.

In some embodiments, compositions are provided herein (e.g., formulations comprising histidine and/or sucrose as described herein) that comprise unconjugated antibody (e.g., in trace amounts) and antibody conjugated to one or more oligonucleotides. As used herein, an "unconjugated antibody" refers to an antibody that is not conjugated to an oligonucleotide. In some embodiments, unconjugated antibody may be referred to as a compound comprising a structure of formula (I): $[R^1]_{n1}$—$R^2$, for which n1 is zero. Accordingly, in some embodiments, compositions are provided (e.g., formulations as described herein) that comprise compounds (e.g., complexes) comprising a structure of formula (I): $[R^1]_{n1}$—$R^2$, for which each $R^1$ independently comprises a group comprising an oligonucleotide, $R^2$ comprises an antibody and n1 is an integer of zero or greater that reflects the number of instances of $R^1$ in the complex. In some embodiments, n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a composition, for which n1 is zero, compared with all compounds of that structure in the composition for which n1 is one or greater, is less than 10%, less than 5%, less than 1% less than 0.5%, less than 0.1%, less than 0.05%, or less than 0.01%. As such, in some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, each instance of $R^1$ in a complex is conjugated to a different amino acid residue of the antibody. In some embodiments, each instance of $R^1$ in a complex is covalently linked to a different amino acid residue of the antibody. In some embodiments, an amino acid to which $R^1$ is covalently linked comprises an F-amino group (e.g., lysine, arginine). In some embodiments, each different amino acid comprises an F-amino group (e.g., lysine, arginine). However, in some embodiments, an amino acid to which $R^1$ is covalently linked is a cysteine. In some embodiments, each different amino acid to which $R^1$ is covalently linked is a cysteine. In some embodiments, $R^1$ is directly covalently linked to an amino acid residue of the antibody. However, in some embodiments, $R^1$ is indirectly covalently linked to an amino acid of the antibody, e.g., covalently linked to a glycosylation site on the amino acid.

In some embodiments, $R^1$ is not covalently linked to an amino acid residue residing in a CDR region of the antibody.

In some embodiments, complexes provided herein (e.g., in compositions or formulations described herein) comprise a structure of formula (I): $[R^1]_{n1}$—$R^2$, in which each instance of $R^1$ independently comprises a group of the formula (Ia):

(Ia)
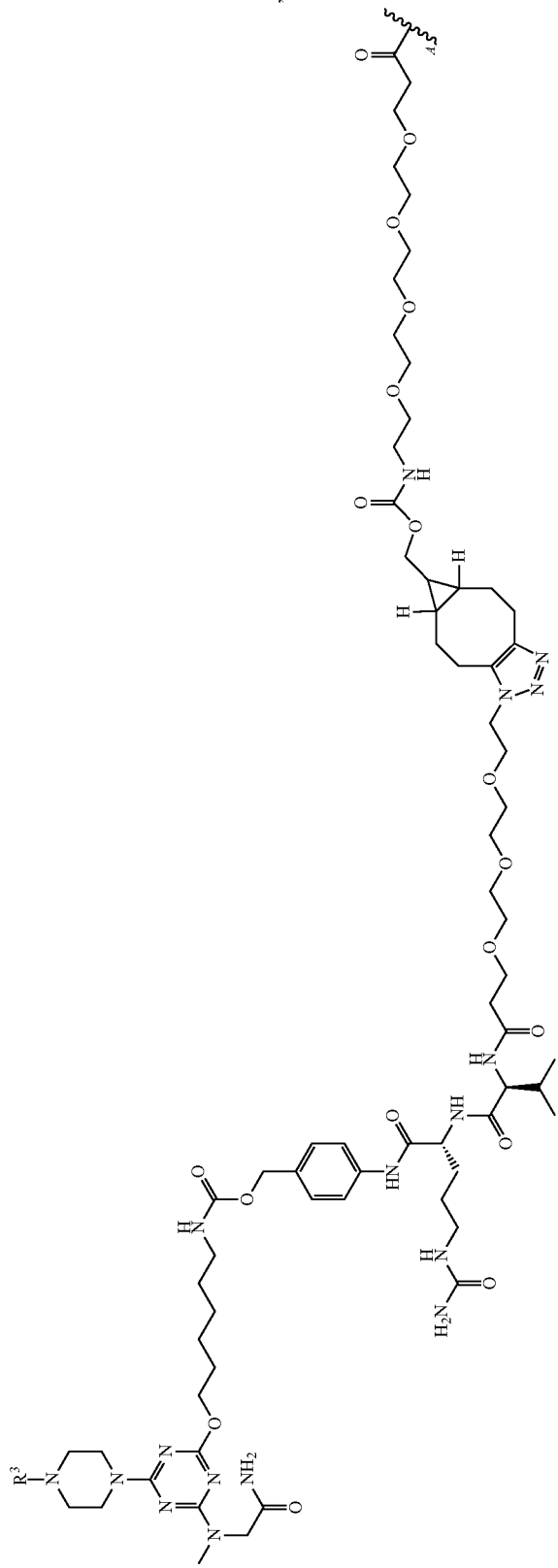

in which R³ comprises an oligonucleotide, e.g., a phosphorodiamidate morpholino oligomer (PMO); and R¹ is covalently linked (e.g., indirectly or directly linked, e.g., directly linked) to R² at attachment point A. In some embodiments, in each complex n1 is independently an integer (e.g., of one or greater) representing the number of instances of R¹ in each complex. In some embodiments, R² comprises an antibody comprising a sequence as set forth in Table 2. For example, in some embodiments, R² comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, R² comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, R² comprises an antibody comprising a VH comprising the amino acid sequence of SEQ ID NO: 17 and/or comprising a VL comprising the amino acid sequence of SEQ ID NO: 18. In some embodiments, R² comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, R² comprises an antibody comprising a heavy chain comprising the amino acid sequence of SEQ ID NO: 19 and/or comprising a light chain comprising the amino acid sequence of SEQ ID NO: 20. In some embodiments, R² comprises an antibody that is a Fab fragment, a full-length IgG, a Fab' fragment, a F(ab')₂ fragment, an scFv, or an Fv. In some embodiments, R² comprises an antibody that is a Fab fragment. In some embodiments, R³ comprises an oligonucleotide, e.g., a phosphorodiamidate morpholino oligomer (PMO) comprising the base sequence of CTCCAACATCAAGGAAGATGGCATTTCTAG (SEQ ID NO: 21). In some embodiments, R² comprises a Fab and each R¹ is covalently linked at attachment point A to a different amino acid residue of the Fab, optionally wherein each different amino acid residue is a lysine. In some embodiments, in each complex n1 is independently an integer (e.g., an integer in the range of 1-27, 1-26, 1-10, 1-5, or 1-3).

In some embodiments, complexes provided herein (e.g., in compositions or formulations described herein) comprise a structure of formula (I): $[R^1]_{n1}$—$R^2$, in which each $R^1$ comprises a group of the formula (Ib):

(Ib)
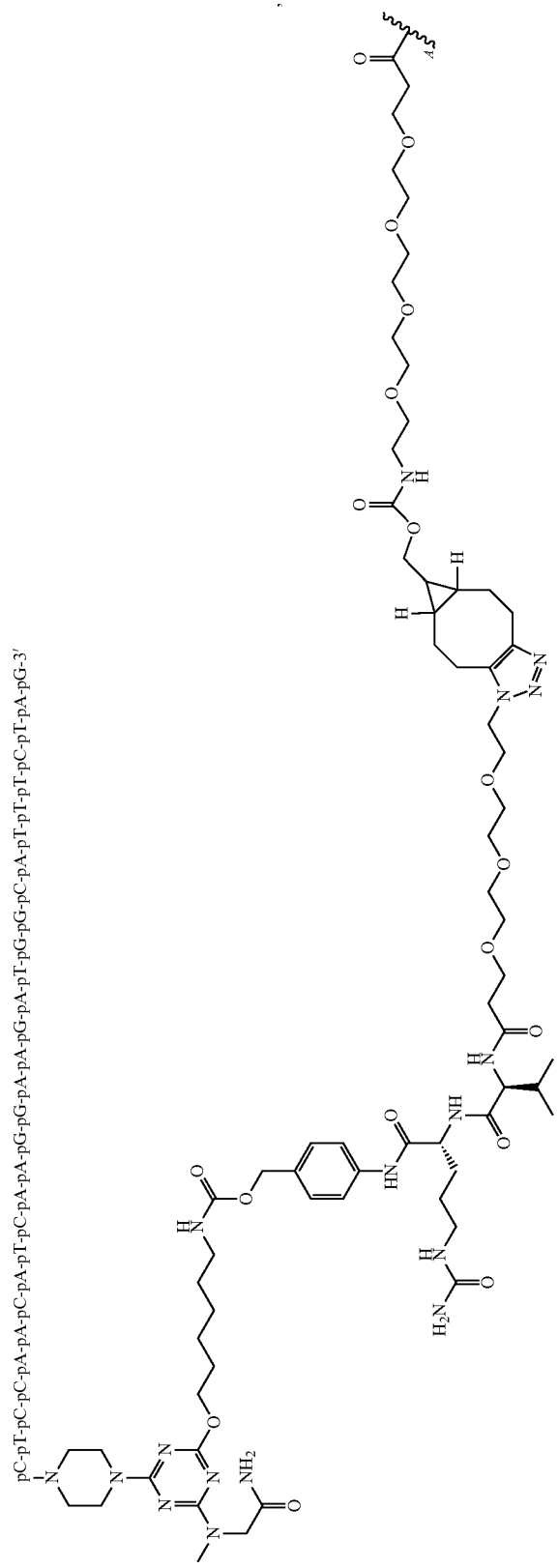

in which -pN indicates a base position of a phosphorodiamidate morpholino oligomer (PMO); $R^1$ is covalently linked (e.g., indirectly or directly linked, e.g., directly linked) to $R^2$ at attachment point A, wherein -p reflects a phosphorodiamidate linkage, and wherein N corresponds to a nucleobase of adenine (A), cytosine (C), guanine (G), or thymine (T), such that the PMO comprises a base sequence of CTCCAACATCAAGGAAGATGGCATTTCTAG (SEQ ID NO: 21). In some embodiments, in each complex n1 is independently an integer (e.g., of one or greater) representing the number of instances of $R^1$ in each complex, and each $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18.

In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a F(ab')$_2$ fragment, an scFv, or an Fv. In some embodiments, $R^2$ comprises an antibody that is a Fab fragment. In some embodiments, in each complex n1 is independently an integer (e.g., an integer in the range of 1-27, 1-26, 1-10, 1-5, or 1-3). In some embodiments, $R^2$ comprises a Fab and each $R^1$ is covalently linked at attachment point A to a different amino acid residue of the Fab, optionally wherein each different amino acid residue is a lysine.

In some embodiments, complexes provided herein (e.g., in compositions or formulations described herein) comprise a structure of formula (I): $[R^1]_{n1}$—$R^2$, in which each $R^1$ comprises a group of the formula (Ic):

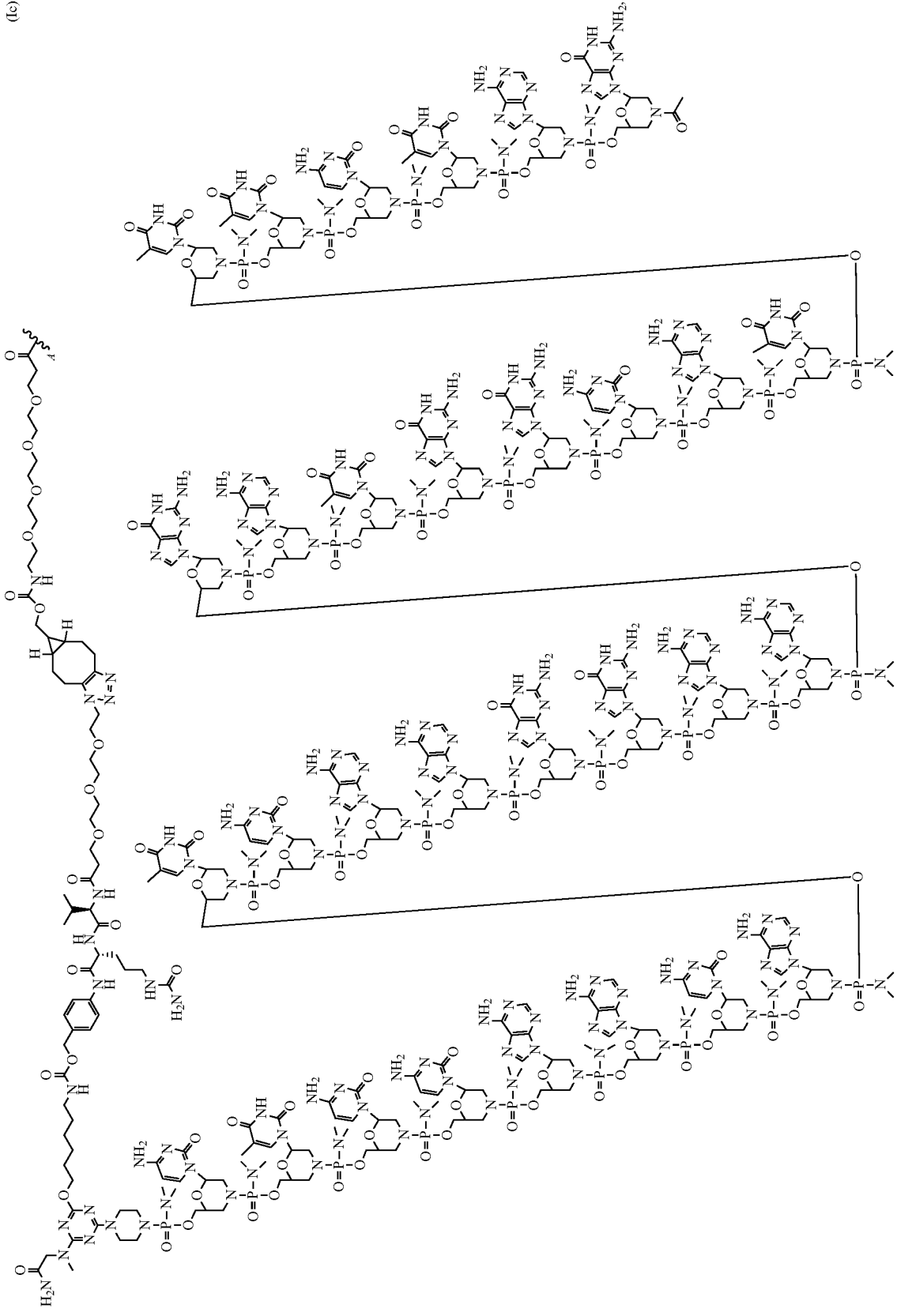

wherein $R^1$ is covalently linked (e.g., indirectly or directly linked, e.g., directly linked) to $R^2$ at attachment point A. In some embodiments, in each complex n1 is independently an integer (e.g., of one or greater) representing the number of instances of $R^1$ in each complex, wherein each $R^1$ is covalently linked to at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a F(ab')$_2$ fragment, an scFv, or an Fv. In some embodiments, $R^2$ comprises an antibody that is a Fab fragment. In some embodiments, in each complex n1 is independently an integer (e.g., an integer in the range of 1-27, 1-26, 1-10, 1-5, or 1-3). In some embodiments, $R^2$ comprises a Fab and each $R^1$ is covalently linked at attachment point A to a different amino acid residue of the Fab, optionally wherein each different amino acid residue is a lysine.

In some embodiments, complexes provided herein (e.g., in compositions or formulations described herein) comprise a structure of the formula (Id):

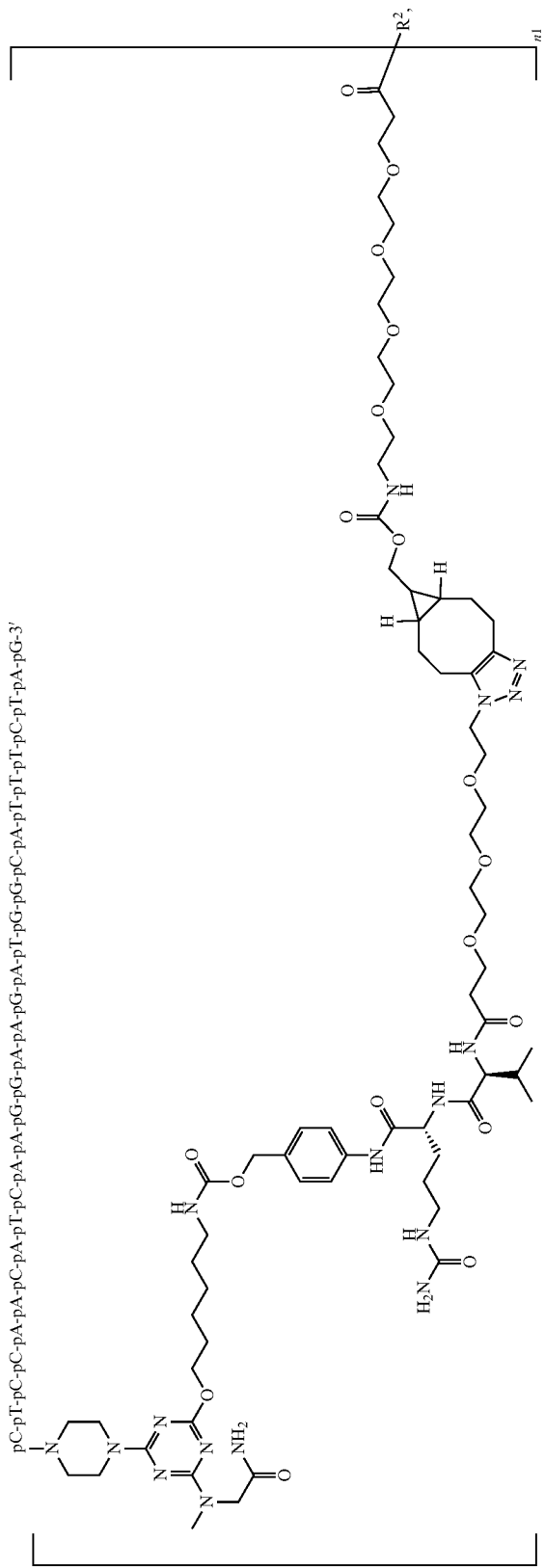

in which -pN indicates a base position of a phosphorodiamidate morpholino oligomer (PMO); wherein -p reflects a phosphorodiamidate linkage, and wherein N corresponds to a nucleobase of adenine (A), cytosine (C), guanine (G), or thymine (T), such that the PMO comprises a base sequence of CTCCAACATCAAGGAAGATGGCATTTCTAG (SEQ ID NO: 21); wherein $R^2$ comprises an antibody comprising a sequence as set forth in Table 2; wherein in each complex n1 is independently an integer (e.g., of one or greater) comprising the amino acid sequence of SEQ ID NO: 20. In some embodiments, in each complex n1 is independently an integer (e.g., an integer in the range of 1-27, 1-26, 1-10, 1-5, or 1-3). In some embodiments, $R^2$ comprises an antibody (e.g., a Fab) that is covalently linked via different amino acid residue of the antibody (e.g., Fab), optionally wherein each different amino acid residue is a lysine.

In some embodiments, complexes described herein comprise a structure of:

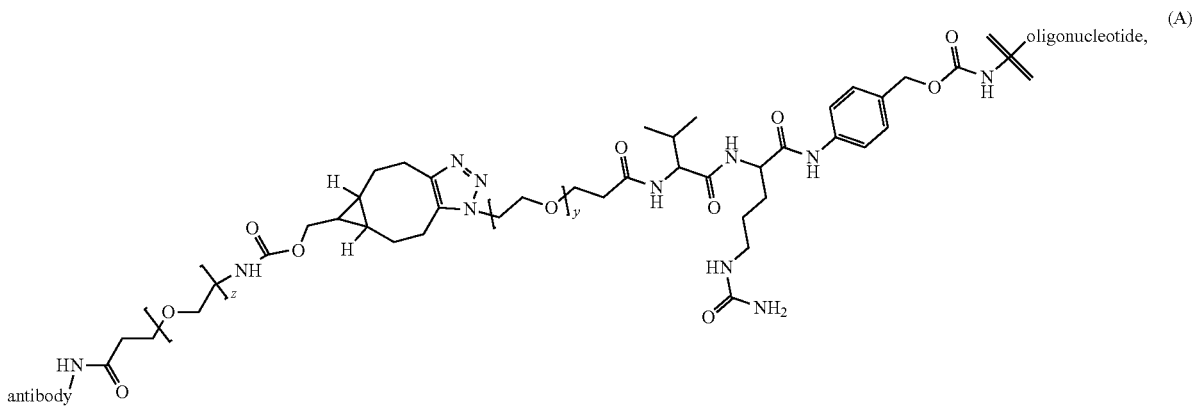

(A)

representing the number of instances of the group enclosed by square brackets, wherein each instance of the group enclosed by square brackets is covalently linked to a different amino acid residue of the antibody (e.g., a Fab), optionally wherein each different amino acid residue is a lysine. In some embodiments, $R^2$ comprises an antibody (e.g., a Fab) comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody (e.g., a Fab) comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody (e.g., a Fab) comprising a VH comprising the amino acid sequence of SEQ ID NO: 17 and/or comprising a VL comprising the amino acid sequence of SEQ ID NO: 18. In some embodiments, $R^2$ comprises an antibody (e.g., a Fab) comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody (e.g., a Fab) comprising a heavy chain comprising the amino acid sequence of SEQ ID NO: 19 and/or comprising a light chain wherein y is 0-15 (e.g., 3) and z is 0-15 (e.g., 4). In some embodiments, the antibody is an anti-TfR1 antibody (e.g., the anti-TfR1 antibody provided in Table 2). In some embodiments, the oligonucleotide is a PMO and comprises the nucleotide sequence of SEQ ID NO: 21. In some embodiments, the amide shown adjacent to the anti-TfR1 antibody in the structure (A) results from a reaction with an amine of the anti-TfR1 antibody, such as a lysine epsilon amine. In some embodiments, a complex described herein comprises an anti-TfR1 Fab covalently linked via a lysine of the Fab to the 5' end of a PMO. In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a F(ab')₂ fragment, an scFv, or an Fv.

Antibodies

In some embodiments, complexes provided herein comprise an antibody that binds human transferrin receptor 1 (TfR1). An example human transferrin receptor 1 amino acid sequence, corresponding to NCBI sequence NP_003225.2 (transferrin receptor protein 1 isoform 1, *Homo sapiens*) is as follows:

(SEQ ID NO: 35)
MMDQARSAFSNLFGGEPLSYTRFSLARQVDGDNSHVEMKLAVDEEENADN

NTKANVTKPKRCSGSICYGTIAVIVFFLIGFMIGYLGYCKGVEPKTECER

LAGTESPVREEPGEDFPAARRLYWDDLKRKLSEKLDSTDFTGTIKLLNEN

SYVPREAGSQKDENLALYVENQFREFKLSKVWRDQHFVKIQVKDSAQNSV

IIVDKNGRLVYLVENPGGYVAYSKAATVTGKLVHANFGTKKDFEDLYTPV

NGSIVIVRAGKITFAEKVANAESLNAIGVLIYMDQTKFPIVNAELSFFGH

AHLGTGDPYTPGFPSFNHTQFPPSRSSGLPNIPVQTISRAAAEKLFGNME

GDCPSDWKTDSTCRMVTSESKNVKLTVSNVLKEIKILNIFGVIKGFVEPD

HYVVVGAQRDAWGPGAAKSGVGTALLLKLAQMFSDMVLKDGFQPSRSIIF

ASWSAGDFGSVGATEWLEGYLSSLHLKAFTYINLDKAVLGTSNFKVSASP

LLYTLIEKTMQNVKHPVTGQFLYQDSNWASKVEKLTLDNAAFPFLAYSGI

PAVSFCFCEDTDYPYLGTTMDTYKELIERIPELNKVARAAAEVAGQFVIK

LTHDVELNLDYERYNSQLLSFVRDLNQYRADIKEMGLSLOWLYSARGDFF

RATSRLTTDFGNAEKTDRFVMKKLNDRVMRVEYHFLSPYVSPKESPFRHV

FWGSGSHTLPALLENLKLRKQNNGAFNETLFRNQLALATWTIQGAANALS

GDVWDIDNEF.

Table 2 provides examples of sequences of an anti-TfR1 antibody useful in the complexes provided herein.

TABLE 2

Examples of anti-TfR1 antibody sequences

| antibody | IMGT | Kabat | Chothia |
|---|---|---|---|
| CDR-H1 | GYSITSGYY (SEQ ID NO: 1) | SGYYWN (SEQ ID NO: 7) | GYSITSGY (SEQ ID NO: 12) |
| CDR-H2 | ITFDGAN (SEQ ID NO: 2) | YITFDGANNYNPSLKN (SEQ ID NO: 8) | FDG (SEQ ID NO: 13) |
| CDR-H3 | TRSSYDYDVLDY (SEQ ID NO: 3) | SSYDYDVLDY (SEQ ID NO: 9) | SYDYDVLD (SEQ ID NO: 14) |
| CDR-L1 | QDISNF (SEQ ID NO: 4) | RASQDISNFLN (SEQ ID NO: 10) | SQDISNF (SEQ ID NO: 15) |

TABLE 2-continued

Examples of anti-TfR1 antibody sequences

| antibody | IMGT | Kabat | Chothia |
|---|---|---|---|
| CDR-L2 | YTS (SEQ ID NO: 5) | YTSRLHS (SEQ ID NO: 11) | YTS (SEQ ID NO: 5) |
| CDR-L3 | QQGHTLPYT (SEQ ID NO: 6) | QQGHTLPYT (SEQ ID NO: 6) | GHTLPY (SEQ ID NO: 16) |
| VH | QVQLQESGPGLVKPSQTLSLTCTVTGYSITSGYYWNWIRQPPGKGLEWIGYITFDGANNYNPSLKNRVSISRDTSKNQFSLKLSSVTAEDTATYYCTRSSYDYDVLDYWGQGTTVTVSS (SEQ ID NO: 17) | | |
| VL | DIQMTQSPSSLSASVGDRVTITCRASQDISNFLNWYQQKPGQPVKLLIYYTSRLHSGVPSRFSGSGSGTDFTLTISSLQPEDFATYYCQQGHTLPYTFGQGTKLEIK (SEQ ID NO: 18) | | |
| Fab HC | QVQLQESGPGLVKPSQTLSLTCTVTGYSITSGYYWNWIRQPPGKGLEWIGYITFDGANNYNPSLKNRVSISRDTSKNQFSLKLSSVTAEDTATYYCTRSSYDYDVLDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 19) | | |
| Fab LC | DIQMTQSPSSLSASVGDRVTITCRASQDISNFLNWYQQKPGQPVKLLIYYTSRLHSGVPSRFSGSGSGTDFTLTISSLQPEDFATYYCQQGHTLPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 20) | | |

In some embodiments, the anti-TfR1 antibody of the present disclosure comprises a heavy chain complementarity determining region 1 (1CDR-H1) of SEQ ID NO: 1 (according to the IMGT definition system), a heavy chain complementarity determining region 2 (CDR-H2) of SEQ ID NO: 2 (according to the IMGT definition system), a heavy chain complementarity determining region 3 (CDR-H3) of SEQ ID NO: 3 (according to the IMGT definition system), a light chain complementarity determining region 1 (CDR-L1) of SEQ ID NO: 4 (according to the IMGT definition system), a light chain complementarity determining region 2 (CDR-L2) of SEQ ID NO: 5 (according to the IMGT definition system), and a light chain complementarity determining region 3 (CDR-L3) of SEQ ID NO: 6 (according to the IMGT definition system).

In some embodiments, the anti-TfR1 antibody of the present disclosure comprises a heavy chain complementarity determining region 1 (CDR-H1) of SEQ ID NO: 7 (according to the Kabat definition system), a heavy chain complementarity determining region 2 (CDR-H2) of SEQ ID NO: 8 (according to the Kabat definition system), a heavy chain complementarity determining region 3 (CDR-H3) of SEQ ID NO: 9 (according to the Kabat definition system), a light chain complementarity determining region 1 (CDR-L1) of SEQ ID NO: 10 (according to the Kabat definition system), a light chain complementarity determining region 2 (CDR-L2) of SEQ ID NO: 11 (according to the Kabat definition system), and a light chain complementarity determining region 3 (CDR-L3) of SEQ ID NO: 6 (according to the Kabat definition system).

In some embodiments, the anti-TfR1 antibody of the present disclosure comprises a heavy chain complementarity determining region 1 (CDR-H1) of SEQ ID NO: 12 (according to the Chothia definition system), a heavy chain complementarity determining region 2 (CDR-H2) of SEQ ID NO: 13 (according to the Chothia definition system), a heavy chain complementarity determining region 3 (CDR-H3) of SEQ ID NO: 14 (according to the Chothia definition system), a light chain complementarity determining region 1 (CDR-L1) of SEQ ID NO: 15 (according to the Chothia definition system), a light chain complementarity determining region 2 (CDR-L2) of SEQ ID NO: 5 (according to the Chothia definition system), and a light chain complementarity determining region 3 (CDR-L3) of SEQ ID NO: 16 (according to the Chothia definition system).

In some embodiments, the anti-TfR1 antibody of the present disclosure comprises a heavy chain variable region (VH) containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VH comprising the amino acid sequence of SEQ ID NO: 17. Alternatively or in addition (e.g., in addition), the anti-TfR1 antibody of the present disclosure comprises a light chain variable region (VL) containing no more than 25 amino acid variations (e.g., no more than 25, 24, 23, 22, 21, 20, 19, 18, 17, 16, 15, 14, 13, 12, 11, 10, 9, 8, 7, 6, 5, 4, 3, 2, or 1 amino acid variation) in the framework regions as compared with the VL comprising the amino acid sequence of SEQ ID NO: 18.

In some embodiments, the anti-TfR1 antibody of the present disclosure comprises a VH comprising an amino acid sequence that is at least 75% (e.g., 75%, 80%, 85%, 90%, 95%, 98%, or 99%) identical in the framework regions to the VH comprising the amino acid sequence of SEQ ID NO: 17. Alternatively or in addition (e.g., in addition), in some embodiments, the anti-TfR1 antibody of the present disclosure comprises a VL comprising an amino acid sequence that is at least 75% (e.g., 75%, 80%, 85%, 90%, 95%, 98%, or 99%) identical in the framework regions to the VL comprising the amino acid sequence of SEQ ID NO: 18.

In some embodiments, the anti-TfR1 antibody of the present disclosure comprises a VH comprising the amino acid sequence of SEQ ID NO: 17. Alternatively or in addition (e.g., in addition), in some embodiments, the anti-TfR1 antibody of the present disclosure comprises a VL comprising the amino acid sequence of SEQ ID NO: 18.

In some embodiments, the anti-TfR1 antibody of the present disclosure comprises a heavy chain comprising an amino acid sequence least 75% (e.g., 75%, 80%, 85%, 90%, 95%, 98%, or 99%) identical to the amino acid sequence of SEQ ID NO: 19. In some embodiments, the anti-TfR1 antibody of the present disclosure is a Fab that comprises a heavy chain comprising an amino acid sequence least 75% (e.g., 75%, 80%, 85%, 90%, 95%, 98%, or 99%) identical to the amino acid sequence of SEQ ID NO: 19. Alternatively or in addition (e.g., in addition), the anti-TfR1 antibody of the present disclosure comprises a light chain comprising an amino acid sequence least 75% (e.g., 75%, 80%, 85%, 90%, 95%, 98%, or 99%) identical to the amino acid sequence of SEQ ID NO: 20. Alternatively or in addition (e.g., in addition), the anti-TfR1 antibody of the present disclosure is a Fab that comprises a light chain comprising an amino acid sequence least 75% (e.g., 75%, 80%, 85%, 90%, 95%, 98%, or 99%) identical to the amino acid sequence of SEQ ID NO: 20.

In some embodiments, the anti-TfR1 antibody of the present disclosure comprises a heavy chain comprising the amino acid sequence of SEQ ID NO: 19. In some embodiments, the anti-TfR1 antibody of the present disclosure is a Fab that comprises a heavy chain comprising the amino acid sequence of SEQ ID NO: 19. Alternatively or in addition (e.g., in addition), the anti-TfR1 antibody of the present disclosure comprises a light chain comprising the amino acid sequence of SEQ ID NO: 20. Alternatively or in addition (e.g., in addition), the anti-TfR1 antibody of the present disclosure is a Fab that comprises a light chain comprising the amino acid sequence of SEQ ID NO: 20.

In some embodiments, the anti-TfR1 antibody provided herein may have one or more post-translational modifications. In some embodiments, N-terminal cyclization, also called pyroglutamate formation (pyro-Glu), may occur in the antibody at N-terminal Glutamate (Glu) and/or Glutamine (Gln) residues during production. As such, it should be appreciated that an antibody specified as having a sequence comprising an N-terminal glutamate or glutamine residue encompasses antibodies that have undergone pyroglutamate formation resulting from a post-translational modification. In some embodiments, pyroglutamate formation occurs in a heavy chain sequence. In some embodiments, pyroglutamate formation occurs in a light chain sequence.

Oligonucleotides

In some embodiments, an oligonucleotide of the complexes described herein is a single stranded oligonucleotide. In some embodiments, the oligonucleotide is useful for targeting DMD (e.g., for exon skipping). In some embodiments, an oligonucleotide that is useful for targeting DMD (e.g., for exon skipping) targets a DMD allele (e.g., a mutated DMD allele). In some embodiments, an oligonucleotide useful for targeting DMD (e.g., for exon skipping) targets a region of a DMD RNA (e.g., the Dp427m transcript of SEQ ID NO: 24). In some embodiments, an oligonucleotide useful for targeting DMD (e.g., for exon skipping) comprises a region of complementarity to a DMD RNA (e.g., the Dp427m transcript of SEQ ID NO: 23). In some embodiments, an oligonucleotide useful for targeting DMD (e.g., for exon skipping) comprises a region of complementarity to an exon (e.g., exons 8, 23, 43, 44, 45, 46, 50, 51, 52, 53, or 55) or an intron of a DMD RNA. In some embodiments, an oligonucleotide useful for targeting DMD (e.g., for exon skipping) targets a splicing donor site, a splicing acceptor site, a branch point, or an exonic splicing enhancer (ESE) of a DMD RNA (e.g., a DMD pre-mRNA encoded by Homo sapiens DMD gene (e.g., NCBI Accession No. NG_012232.1). In some embodiments, an oligonucleotide useful for targeting DMD (e.g., for exon skipping) targets an exonic splicing enhancer (ESE) sequence in DMD (e.g., an ESE sequence of exon 23, 44, 45, 46, 50, 51, 52, 53, or 55).

Examples of DMD RNA sequences and exon sequences that may be targeted by an oligonucleotide of a complex are provided below.

Homo sapiens dystrophin (DMD), transcript variant Dp427m, mRNA (NCBI Reference Sequence: NM_004006.2)(SEQ ID NO: 23).

Homo sapiens dystrophin (DMD), transcript variant Dp427m, exon 51 (nucleotide positions 7554-7786 of NCBI Reference Sequence: NM_004006.2) (SEQ ID NO: 24)

-continued
```
CTCCTACTCAGACTGTTACTCTGGTGACACAACCTGTGGTTACTAAGGAAACTGCCAT

CTCCAAACTAGAAATGCCATCTTCCTTGATGTTGGAGGTACCTGCTCTGGCAGATTTC

AACCGGGCTTGGACAGAACTTACCGACTGGCTTTCTCTGCTTGATCAAGTTATAAAT

CACAGAGGGTGATGGTGGGTGACCTTGAGGATATCAACGAGATGATCATCAAGCAGA

AG
```

Homo sapiens dystrophin (DMD), transcript variant Dp427m, exon 8
(nucleotide positions 894-1075 of NCBI Reference Sequence: NM_004006.2)
(SEQ ID NO: 25)
```
ATGTTGATACCACCTATCCAGATAAGAAGTCCATCTTAATGTACATCACATCACTCTT

CCAAGTTTTGCCTCAACAAGTGAGCATTGAAGCCATCCAGGAAGTGGAAATGTTGCC

AAGGCCACCTAAAGTGACTAAAGAAGAACATTTTCAGTTACATCATCAAATGCACTA

TTCTCAACAG
```

Homo sapiens dystrophin (DMD), transcript variant Dp427m, exon 23
(nucleotide positions 3194-3406 of NCBI Reference Sequence: NM_004006.2)
(SEQ ID NO: 26)
```
GCTTTACAAAGTTCTCTGCAAGAGCAACAAAGTGGCCTATACTATCTCAGCACCACTG

TGAAAGAGATGTCGAAGAAAGCGCCCTCTGAAATTAGCCGGAAATATCAATCAGAAT

TTGAAGAAATTGAGGGACGCTGGAAGAAGCTCTCCTCCCAGCTGGTTGAGCATTGTC

AAAAGCTAGAGGAGCAAATGAATAAACTCCGAAAAATTCAG
```

Homo sapiens dystrophin (DMD), transcript variant Dp427m, exon 43
(nucleotide positions 6362-6534 of NCBI Reference Sequence: NM_004006.2)
(SEQ ID NO: 27)
```
AATATAAAAGATAGTCTACAACAAAGCTCAGGTCGGATTGACATTATTCATAGCAAG

AAGACAGCAGCATTGCAAAGTGCAACGCCTGTGGAAAGGGTGAAGCTACAGGAAGC

TCTCTCCCAGCTTGATTTCCAATGGGAAAAAGTTAACAAAATGTACAAGGACCGACA

AGG
```

Homo sapiens dystrophin (DMD), transcript variant Dp427m, exon 44
(nucleotide positions 6535-6682 of NCBI Reference Sequence: NM_004006.2)
(SEQ ID NO: 28)
```
GCGATTTGACAGATCTGTTGAGAAATGGCGGCGTTTTCATTATGATATAAAGATATTT

AATCAGTGGCTAACAGAAGCTGAACAGTTTCTCAGAAAGACACAAATTCCTGAGAAT

TGGGAACATGCTAAATACAAATGGTATCTTAAG
```

Homo sapiens dystrophin (DMD), transcript variant Dp427m, exon 45
(nucleotide positions 6683-6858 of NCBI Reference Sequence: NM_004006.2)
(SEQ ID NO: 36)
```
GAACTCCAGGATGGCATTGGGCAGCGGCAAACTGTTGTCAGAACATTGAATGCAACT

GGGGAAGAAATAATTCAGCAATCCTCAAAAACAGATGCCAGTATTCTACAGGAAAAA

TTGGGAAGCCTGAATCTGCGGTGGCAGGAGGTCTGCAAACAGCTGTCAGACAGAAAA

AAGAG
```

Homo sapiens dystrophin (DMD), transcript variant Dp427m, exon 46
(nucleotide positions 6859-7006 of NCBI Reference Sequence: NM_004006.2)
(SEQ ID NO: 29)
```
GCTAGAAGAACAAAAGAATATCTTGTCAGAATTTCAAAGAGATTTAAATGAATTTGT

TTTATGGTTGGAGGAAGCAGATAACATTGCTAGTATCCCACTTGAACCTGGAAAAGA

GCAGCAACTAAAAGAAAAGCTTGAGCAAGTCAAG
```

Homo sapiens dystrophin (DMD), transcript variant Dp427m, exon 50
(nucleotide positions 7445-7553 of NCBI Reference Sequence: NM_004006.2)
(SEQ ID NO: 30)
```
AGGAAGTTAGAAGATCTGAGCTCTGAGTGGAAGGCGGTAAACCGTTTACTTCAAGAG

CTGAGGGCAAAGCAGCCTGACCTAGCTCCTGGACTGACCACTATTGGAGCCT
```

```
Homo sapiens dystrophin (DMD), transcript variant Dp427m, exon 51
(nucleotide positions 7554-7786 of NCBI Reference Sequence: NM_004006.2)
                                                           (SEQ ID NO: 31)
CTCCTACTCAGACTGTTACTCTGGTGACACAACCTGTGGTTACTAAGGAAACTGCCAT

CTCCAAACTAGAAATGCCATCTTCCTTGATGTTGGAGGTACCTGCTCTGGCAGATTTC

AACCGGGCTTGGACAGAACTTACCGACTGGCTTTCTCTGCTTGATCAAGTTATAAAAT

CACAGAGGGTGATGGTGGGTGACCTTGAGGATATCAACGAGATGATCATCAAGCAGA

AG

Homo sapiens dystrophin (DMD), transcript variant Dp427m, exon 52
(nucleotide positions 7787-7904 of NCBI Reference Sequence: NM_004006.2)
                                                           (SEQ ID NO: 32)
GCAACAATGCAGGATTTGGAACAGAGGCGTCCCCAGTTGGAAGAACTCATTACCGCT

GCCCAAAATTTGAAAAACAAGACCAGCAATCAAGAGGCTAGAACAATCATTACGGAT

CGAA

Homo sapiens dystrophin (DMD), transcript variant Dp427m, exon 53
(nucleotide positions 7905-8116 of NCBI Reference Sequence: NM_004006.2)
                                                           (SEQ ID NO: 33)
TTGAAAGAATTCAGAATCAGTGGGATGAAGTACAAGAACACCTTCAGAACCGGAGGC

AACAGTTGAATGAAATGTTAAAGGATTCAACACAATGGCTGGAAGCTAAGGAAGAA

GCTGAGCAGGTCTTAGGACAGGCCAGAGCCAAGCTTGAGTCATGGAAGGAGGGTCCC

TATACAGTAGATGCAATCCAAAAGAAAATCACAGAAACCAAG

Homo sapiens dystrophin (DMD), transcript variant Dp427m, exon 55
(nucleotide positions 8272-8461 of NCBI Reference Sequence: NM_004006.2)
                                                           (SEQ ID NO: 34)
GGTGAGTGAGCGAGAGGCTGCTTTGGAAGAAACTCATAGATTACTGCAACAGTTCCC

CCTGGACCTGGAAAAGTTTCTTGCCTGGCTTACAGAAGCTGAAACAACTGCCAATGTC

CTACAGGATGCTACCCGTAAGGAAAGGCTCCTAGAAGACTCCAAGGGAGTAAAAGA

GCTGATGAAACAATGGCAA
```

In some embodiments, an oligonucleotide useful for targeting DMD (e.g., for exon skipping) is 15-40 (e.g., 15-40, 15-35, 15-30, 15-25, 15-20, 20-40, 20-35, 20-30, 20-25, 25-40, 25-35, 25-30, 25-28, 28-30, 30-40, 30-32, 32-35, 30-35, or 35-40) nucleotides in length. In some embodiments, an oligonucleotide useful for targeting DMD (e.g., for exon skipping) is 15, 16, 17, 18, 19, 20, 21, 22, 23, 24, 25, 26, 27, 28, 29, or 30 nucleotides in length, optionally 20-35, or 30 nucleotides in length.

In some embodiments, an oligonucleotide useful for targeting DMD (e.g., for exon skipping) comprises a region of complementarity of at least 8 (e.g., at least 8, 9, 10, 11, 12, 13, 14, 15, 16, 17, 18, 19, 20, 21, 22, 23, 24, 25, 26, 27, 28, 29, or 30) consecutive nucleotides to a DMD RNA. In some embodiments, an oligonucleotide useful for targeting DMD (e.g., for exon skipping) comprises a region of complementarity of at least 8 (e.g., at least 8, 9, 10, 11, 12, 13, 14, 15, 16, 17, 18, 19, 20, 21, 22, 23, 24, 25, 26, 27, 28, 29, or 30) consecutive nucleotides to an exon of a DMD RNA.

In some embodiments, an oligonucleotide useful for targeting DMD (e.g., for exon skipping) comprises a region of complementarity of at least 8 (e.g., at least 8, 9, 10, 11, 12, 13, 14, 15, 16, 17, 18, 19, 20, 21, 22, 23, 24, 25, 26, 27, 28, 29, or 30) consecutive nucleotides to a DMD sequence as set forth in any one of SEQ ID NOs: 23-34.

In some embodiments, an oligonucleotide useful for targeting DMD (e.g., for exon skipping) comprises a region of complementarity of at least 8 (e.g., at least 8, 9, 10, 11, 12, 13, 14, 15, 16, 17, 18, 19, 20, 21, 22, 23, 24, 25, 26, 27, 28, 29, or 30) consecutive nucleotides to a target sequence as set forth in SEQ ID NO: 22 (CTAGAAATGCCATCTTCCTT-GATGTTGGAG). In some embodiments, an oligonucleotide useful for targeting DMD (e.g., for exon skipping) comprises at least 8 (e.g., at least 8, 9, 10, 11, 12, 13, 14, 15, 16, 17, 18, 19, 20, 21, 22, 23, 24, 25, 26, 27, 28, 29, or 30) consecutive nucleotides of a sequence as set forth in SEQ ID NO: 21 (CTCCAACATCAAGGAAGATGGCAT-TTCTAG).

In some embodiments, an oligonucleotide useful for targeting DMD (e.g., for exon skipping) comprises the nucleotide sequence of SEQ ID NO: 21. In some embodiments, any one of the oligonucleotides provided herein is a PMO.

In some embodiments, it should be appreciated that methylation of the nucleobase uracil at the C5 position forms thymine. Thus, in some embodiments, a nucleotide or nucleoside having a C5 methylated uracil (or 5-methyluracil) may be equivalently identified as a thymine nucleotide or nucleoside.

In some embodiments, any one or more of the thymine bases (T's) in any one of the oligonucleotides provided herein (e.g., the oligonucleotide as set forth in SEQ ID NO: 21) may independently and optionally be uracil bases (U's), and/or any one or more of the U's in the oligonucleotides provided herein may independently and optionally be T's.

Compositions

In some embodiments, compositions described herein comprise complexes (i.e., a plurality of complexes), each of which complex comprises an antibody (e.g., anti-TFR1 antibody) covalently linked to one or more oligonucleotides (e.g., an oligonucleotide described herein), wherein the antibody comprises a heavy chain comprising a heavy chain variable region (VH) and a heavy chain constant region, and a light chain comprising a light chain variable region (VL) and a light chain constant region. In some embodiments, the antibody of such complexes comprises a CDR-H1, CDR-H2, CDR-H3, CDR-L1, CDR-L2, and CDR-L3 as set forth in Table 2. Complexes of a composition described herein can comprise any structure provided herein, e.g., a structure of formula (I) (e.g., comprising a group of the formula (Ia), formula (Ib), formula (Ic), or formula (Id)) or formula (A).

In some embodiments, compositions described herein comprise complexes (i.e., a plurality of complexes) wherein each complex comprises a structure of formula (I): $[R^1]_{n1}$—$R^2$, in which each $R^1$ independently comprises a compound comprising an oligonucleotide (e.g., an oligonucleotide described herein) and is covalently linked to $R^2$, wherein $R^2$ comprises an antibody (e.g., anti-TfR1 antibody) comprising a heavy chain comprising a heavy chain variable region (VH) and a heavy chain constant region, and a light chain comprising a light chain variable region (VL) and a light chain constant region. In some embodiments, each $R^1$ of a complex is independently covalently linked to a different amino acid residue (e.g., lysine or cysteine) of $R^2$.

In some embodiments, the value of n1 of complexes in the composition is independently and optionally an integer from one up to the number of amino acid residues to which conjugation is desired or targeted (e.g., the number of lysine residues) in the antibody (e.g., an antibody comprised within $R^2$). In some embodiments, the value of n1 of each complex in the composition is independently and optionally selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 of each complex in the composition is independently and optionally selected from 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 of each complex in the composition is independently selected and optionally from an integer in the range of 1 to 27, 1 to 26, 1 to 10, 1 to 5, or 1 to 3. In some embodiments, the average value of n1 of complexes of the composition is in the range of 1 to 2, 1 to 3, 1 to 5, 1 to 10, 1 to 26, or 1 to 27. In some embodiments, compositions described herein comprise complexes in which the value of n1 is 0. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, a composition described herein comprises antibody that is not conjugated to an oligonucleotide (e.g., in trace amounts) and antibody conjugated to one or more oligonucleotides. In some embodiments, antibody that is not conjugated to an oligonucleotide may be referred to as a compound comprising a structure of formula (I): $[R^1]_{n1}$—$R^2$, for which n1 is zero. Accordingly, in some embodiments, a composition for administration to a subject in the methods described herein comprises compounds (e.g., complexes) comprising a structure of formula (I): $[R^1]_{n1}$—$R^2$, for which each $R^1$ independently comprises a group comprising an oligonucleotide, $R^2$ comprises an antibody and n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a composition, for which n1 is zero, compared with all compounds of that structure in the composition for which n1 is one or greater, is less than 10%, less than 5%, less than 1% less than 0.5%, less than 0.1%, less than 0.05%, or less than 0.01%. As such, in some embodiments, the average value of n1 of complexes in a composition disclosed herein is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

Formulations

Complexes provided herein are formulated in a manner suitable for pharmaceutical use. In some embodiments, complexes can be delivered to a subject using a formulation that minimizes degradation, facilitates delivery and/or (e.g., and) uptake, or provides another beneficial property to complexes in the formulation. Accordingly, in some embodiments, it has been found that formulating complexes (e.g., complexes comprising a PMO covalently linked with a Fab) with histidine and/or sucrose is particularly advantageous for pharmaceutical use, e.g., as described herein. Thus, in some embodiments, provided herein are formulations (e.g., aqueous solutions, lyophilized forms) comprising complexes together with histidine and/or sucrose. In some embodiments, provided herein are formulations comprising complexes together with histidine and/or sucrose in frozen forms. In some embodiments, formulations described herein comprise complexes (e.g., a plurality of complexes comprising a PMO covalently linked with a Fab), histidine, and sucrose. In some embodiments, formulations comprising muscle-targeting complexes (e.g., complexes comprising a PMO covalently linked with a Fab) are formulated with histidine and/or sucrose in aqueous solutions. In some embodiments, formulation comprising a plurality of the complexes, histidine, and sucrose can be lyophilized (e.g., for storage). In some embodiments, the lyophilized formulation may be reconstituted (e.g., with water) for administration to a subject. Such formulations can be suitably prepared such that when administered to a subject, either into the immediate environment of a target cell or systemically, a sufficient amount of the complexes enter target muscle cells.

In some embodiments, formulations are provided herein that comprise complexes (i.e., a plurality of complexes), each of which complex comprises a phosphorodiamidate morpholino oligomer (PMO) covalently linked to an antibody. In some embodiments, provided herein is a formulation comprising complexes, in which each complex comprises a phosphorodiamidate morpholino oligomer (PMO) covalently linked to an anti-TfR1 antibody, optionally wherein the antibody of such complexes comprises a CDR-H1, CDR-H2, CDR-H3, CDR-L1, CDR-L2, and CDR-L3 as set forth in Table 2, and further, in some embodiments, wherein the complexes are formulated with histidine (e.g., L-histidine) and sucrose. In some embodiments, the antibody is an anti-TfR1 antibody.

In some embodiments, formulations are provided that comprise complexes of the formula: $[R^1]_{n1}$—$R^2$, in which each $R^1$ independently comprises a compound comprising an oligonucleotide (e.g., a PMO) and $R^2$ comprises an antibody (e.g., anti-TfR1 antibody), and in which n1 is an integer of one or greater representing the number of instances of $R^1$ in the complex. In some embodiments, formulations are provided that comprise a plurality of complexes wherein each complex comprises a structure of formula (I): $[R^1]_{n1}$—$R^2$, in which each $R^1$ independently comprises a compound comprising an oligonucleotide (e.g., a PMO) and $R^2$ comprises an antibody (e.g., anti-TfR1 antibody), and in which in each complex n1 is an integer independently of one or greater representing the number of instances of $R^1$ in each complex.

In some embodiments, formulations described herein comprise complexes comprising an antibody that comprises a CDR-H1, CDR-H2, CDR-H3, CDR-L1, CDR-L2, and CDR-L3 as set forth in Table 2. In some embodiments, the antibody comprises a VH comprising the amino acid sequence of SEQ ID NO: 17 and a VL comprising the amino acid sequence of SEQ ID NO: 18. In some embodiments, the antibody is a Fab and comprises a heavy chain comprising the amino acid sequence of SEQ ID NO: 19 and a light chain comprising the amino acid sequence of SEQ ID NO: 20.

In some embodiments, the value of n1 of each complex in the formulation is independently and optionally an integer from one up to the number of amino acid residues to which conjugation is desired or targeted (e.g., the number of lysine residues) in the antibody ($R^2$). In some embodiments, the value of n1 of each complex in the formulation is independently and optionally selected from 1, 2, 3, 4, 5, 6, 7, 8, 9, 10, 11, 12, 13, 14, 15, 16, 17, 18, 19, 20, 21, 22, 23, 24, 25, 26, and 27. In some embodiments, the value of n1 of each complex in the formulation is independently and optionally selected from 1, 2, 3, 4, 5, 6, 7, 8, 9, 10, 11, 12, 13, 14, 15, 16, 17, 18, 19, 20, 21, 22, 23, 24, 25 and 26. In some embodiments, the value of n1 of each complex in the formulation is independently selected and optionally from an integer in the range of 1 to 27, 1 to 26, 1 to 10, 1 to 5, or 1 to 3. In some embodiments, the average value of n1 of complexes of the formulation is in the range of 1 to 3, 1 to 5, 1 to 10, 1 to 26 or 1 to 27.

In some embodiments, a formulation described herein comprises antibody that is not conjugated to an oligonucleotide (e.g., in trace amounts) and antibody conjugated to one or more oligonucleotides. In some embodiments, antibody that is not conjugated to an oligonucleotide antibody may be referred to as a compound comprising a structure of formula (I): $[R^1]_{n1}$—$R^2$, for which n1 is zero. Accordingly, in some embodiments, formulations are provided that comprise compounds (e.g., complexes) comprising a structure of formula (I): $[R^1]_{n1}$—$R^2$, for which each $R^1$ independently comprises a group comprising an oligonucleotide, $R^2$ comprises an antibody and n1 is independently an integer of zero or greater that reflects the number of instances of $R^1$ in each compound (e.g., complex). In some embodiments, the fraction of compounds comprising a structure of formula (I): $[R^1]_{n1}$—$R^2$, in a formulation, for which n1 is zero, compared with all compounds of that structure in the formulation for which n1 is one or greater, is less than 10%, less than 5%, less than 1% less than 0.5%, less than 0.1%, less than 0.05%, or less than 0.01%. In some embodiments, the average value of n1 of complexes of the formulation is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1- 4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, each instance of $R^1$ in a complex herein (e.g., a complex of a formulation provided herein) is conjugated to a different amino acid residue of the antibody. In some embodiments, each different amino acid comprises an F-amino group (e.g., lysine, arginine). However, in some embodiments, each different amino acid to which $R^1$ is covalently linked is a cysteine. In some embodiments, $R^1$ is directly covalently linked to an amino acid residue of the antibody. However, in some embodiments, $R^1$ is indirectly covalently linked to an amino acid of the antibody, e.g., covalently linked to a glycosylation site on the amino acid. In some embodiments, formulations are provided in which complexes for which $R^1$ is covalently linked to an amino acid residue residing in a CDR region of the antibody are present in only trace amounts, or in undetectable amount, or not at all. In some embodiments, formulations are provided in which complexes for which $R^1$ is covalently linked to an amino acid residue residing in a CDR region of the antibody are not detectable in the formulation using standard detection techniques.

In some embodiments, formulations provided herein comprise complexes that comprise a structure of formula (I): $[R^1]_{n1}$—$R^2$, in which each instance of $R^1$ in a complex of a formulation provided herein independently comprises a group of the formula (Ia):

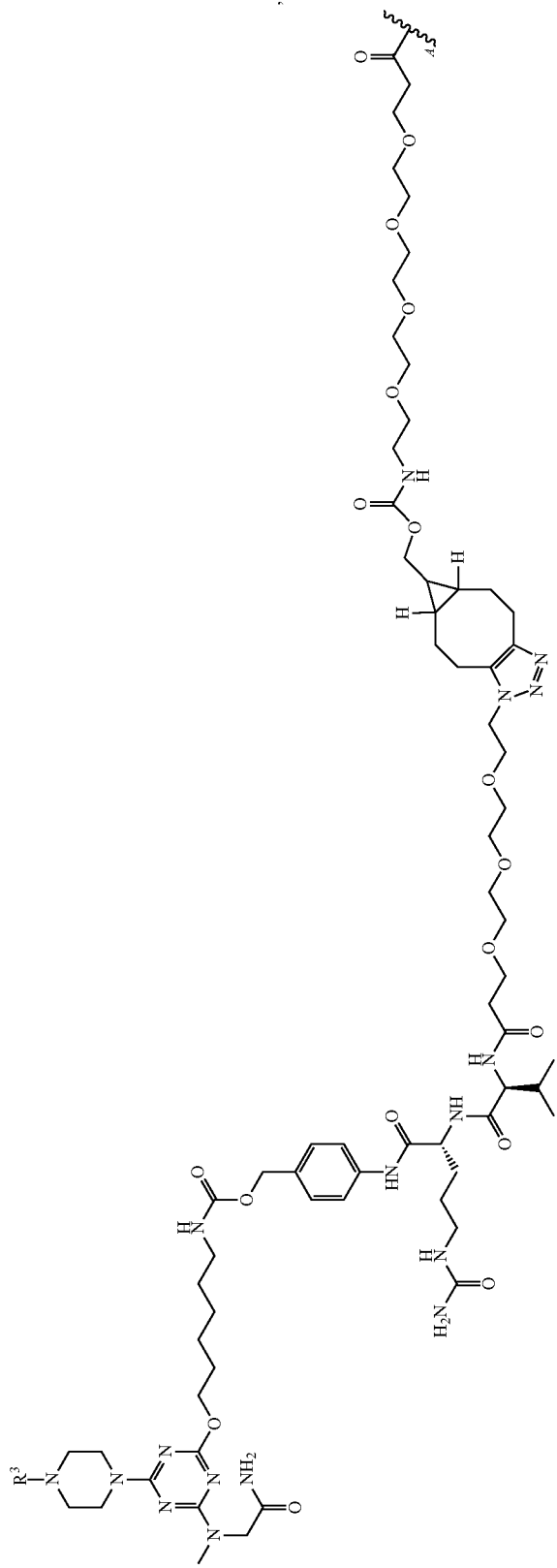

in which $R^3$ comprises an oligonucleotide, e.g., a phosphorodiamidate morpholino oligomer (PMO); and $R^1$ is covalently linked (e.g., indirectly or directly linked, e.g., directly linked) to $R^2$ at attachment point A. In some embodiments, in each complex n1 is independently an integer (e.g., of one or greater) representing the number of instances of $R^1$ in each complex, In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a F(ab')$_2$ fragment, an scFv, or an Fv. In some embodiments, $R^2$ comprises an antibody that is a Fab fragment. In some embodiments, $R^3$ comprises an oligonucleotide, e.g., a phosphorodiamidate morpholino oligomer (PMO) comprising the base sequence of CTCCAACAT-CAAGGAAGATGGCATTTCTAG (SEQ ID NO: 21). In some embodiments, $R^2$ comprises an antibody a Fab and each $R^1$ is covalently linked at attachment point A to a different amino acid residue of the antibody Fab, optionally wherein each different amino acid residue is a lysine. In some embodiments, in each complex n1 is independently an integer (e.g., an integer in the range of 1-27, 1-26, 1-10, 1-5, or 1-3). In some embodiments, formulations provided herein comprise complexes that comprise a structure of formula (I): $[R^1]_{n1}$—$R^2$, wherein n1 is 0. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, formulations provided herein comprise complexes that comprise a structure of formula (I): $[R^1]_{n1}$—$R^2$, in which each instance of $R^1$ in a complex of a formulation provided herein comprises a group of the formula (Ib):

(Ib)
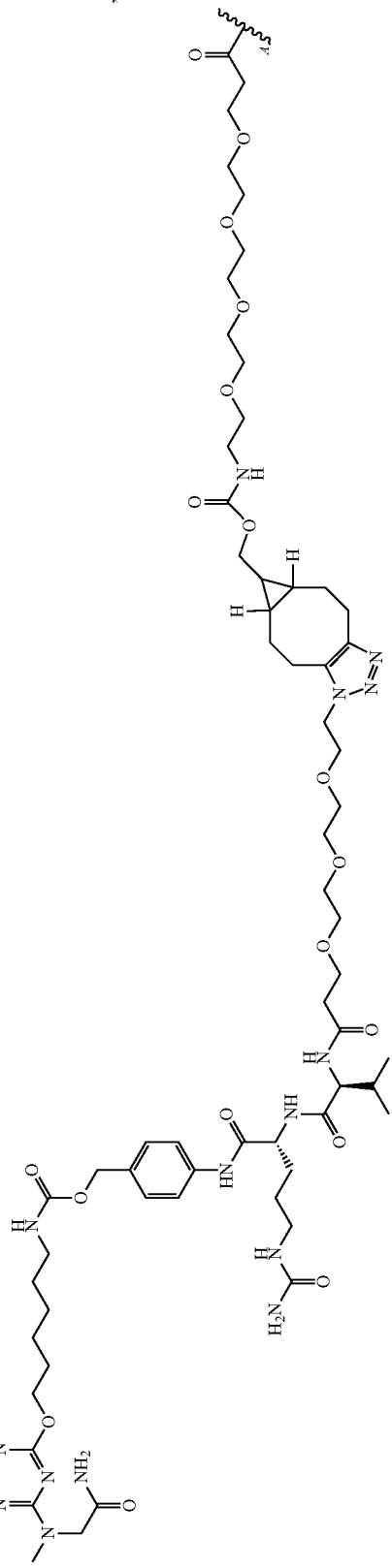

in which -pN indicates a base position of a phosphorodiamidate morpholino oligomer (PMO); $R^1$ is covalently linked (e.g., indirectly or directly linked, e.g., directly linked) to $R^2$ at attachment point A, wherein -p reflects a phosphorodiamidate linkage, and wherein N corresponds to a nucleobase of adenine (A), cytosine (C), guanine (G), or thymine (T), such that the PMO comprises a base sequence of CTCCAACATCAAGGAAGATGGCATTTCTAG (SEQ ID NO: 21). In some embodiments, in each complex n1 is independently an integer (e.g., of one or greater) representing the number of instances of $R^1$ in each complex, and each $R^1$ is covalently linked to $R^2$ at attachment point A. In some embodiments, $R^2$ comprises an antibody comprising a sequence as set forth in Table 2. For example, in some embodiments, $R^2$ comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NO: 6 or 16. In some embodiments, $R^2$ comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody comprising a VH comprising the amino acid sequence of SEQ ID NO: 17 and/or comprising a VL comprising the amino acid sequence of SEQ ID NO: 18. In some embodiments, $R^2$ comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody comprising a heavy chain comprising the amino acid sequence of SEQ ID NO: 19 and/or comprising a light chain comprising the amino acid sequence of SEQ ID NO: 20. In some embodiments, $R^2$ comprises an antibody that is a Fab fragment, a full-length IgG, a Fab' fragment, a F(ab')$_2$ fragment, an scFv, or an Fv. In some embodiments, $R^2$ comprises an antibody that is a Fab fragment. In some embodiments, in each complex n1 is independently an integer (e.g., an integer in the range of 1-27, 1-26, 1-10, 1-5, or 1-3). In some embodiments, $R^2$ comprises a Fab and each $R^1$ is covalently linked at attachment point A to a different amino acid residue of the Fab, optionally wherein each different amino acid residue is a lysine. In some embodiments, formulations provided herein comprise complexes that comprise a structure of formula (I): $[R^1]_{n1}$—$R^2$, wherein n1 is 0. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, formulations provided herein comprise complexes that comprise a structure of formula (I): $[R^1]_n$i-$R^2$, in which each instance of $R^1$ in a complex of a formulation provided herein comprises a group of the formula (Ic):

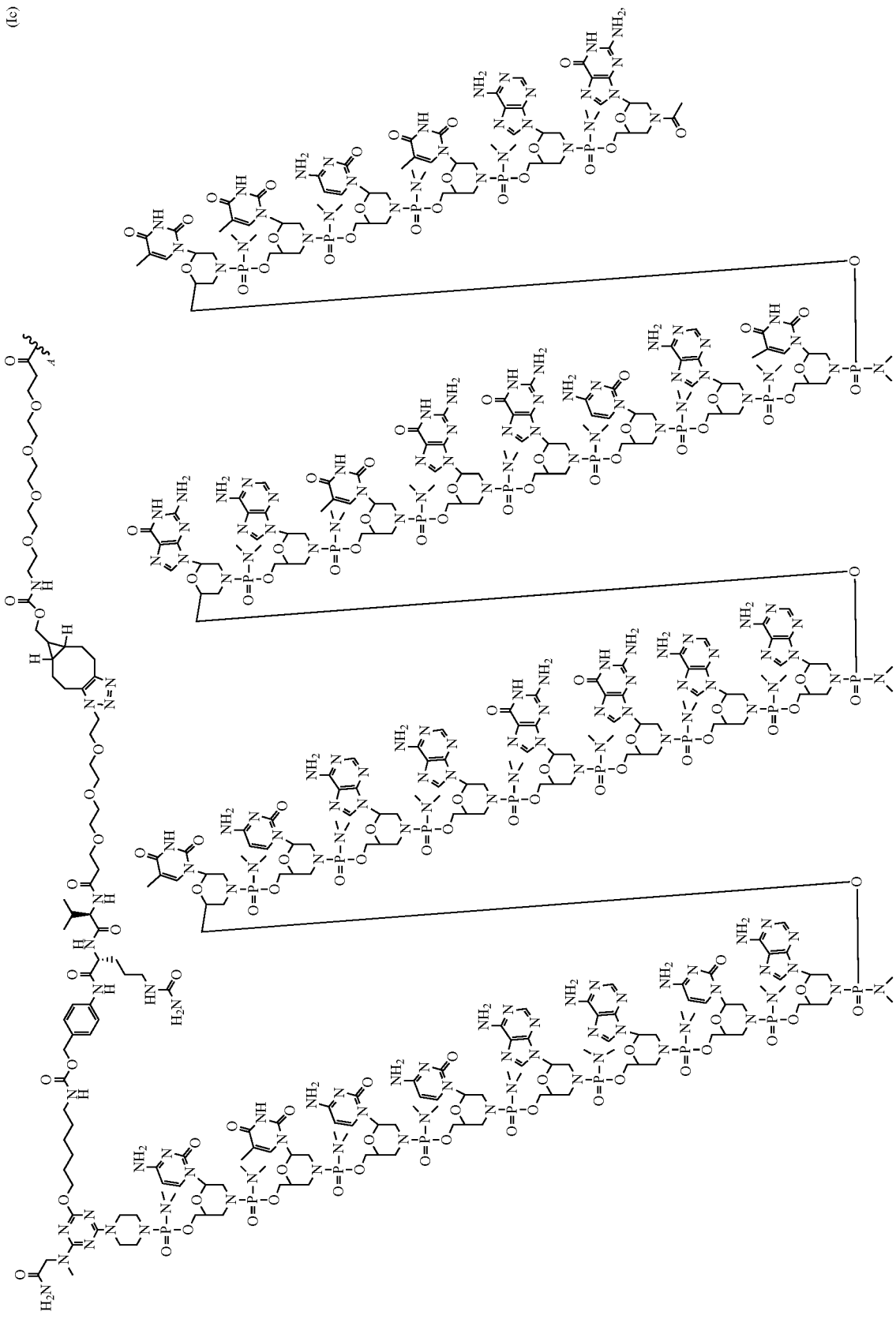

wherein $R^1$ is covalently linked (e.g., indirectly or directly linked, e.g., directly linked) to $R^2$ at attachment point A.

In some embodiments, formulations provided herein comprise complexes that comprise a structure of formula (I): $[R^1]_{n1}$—$R^2$, in which each instance of $R^1$ in a complex of a formulation provided herein is:

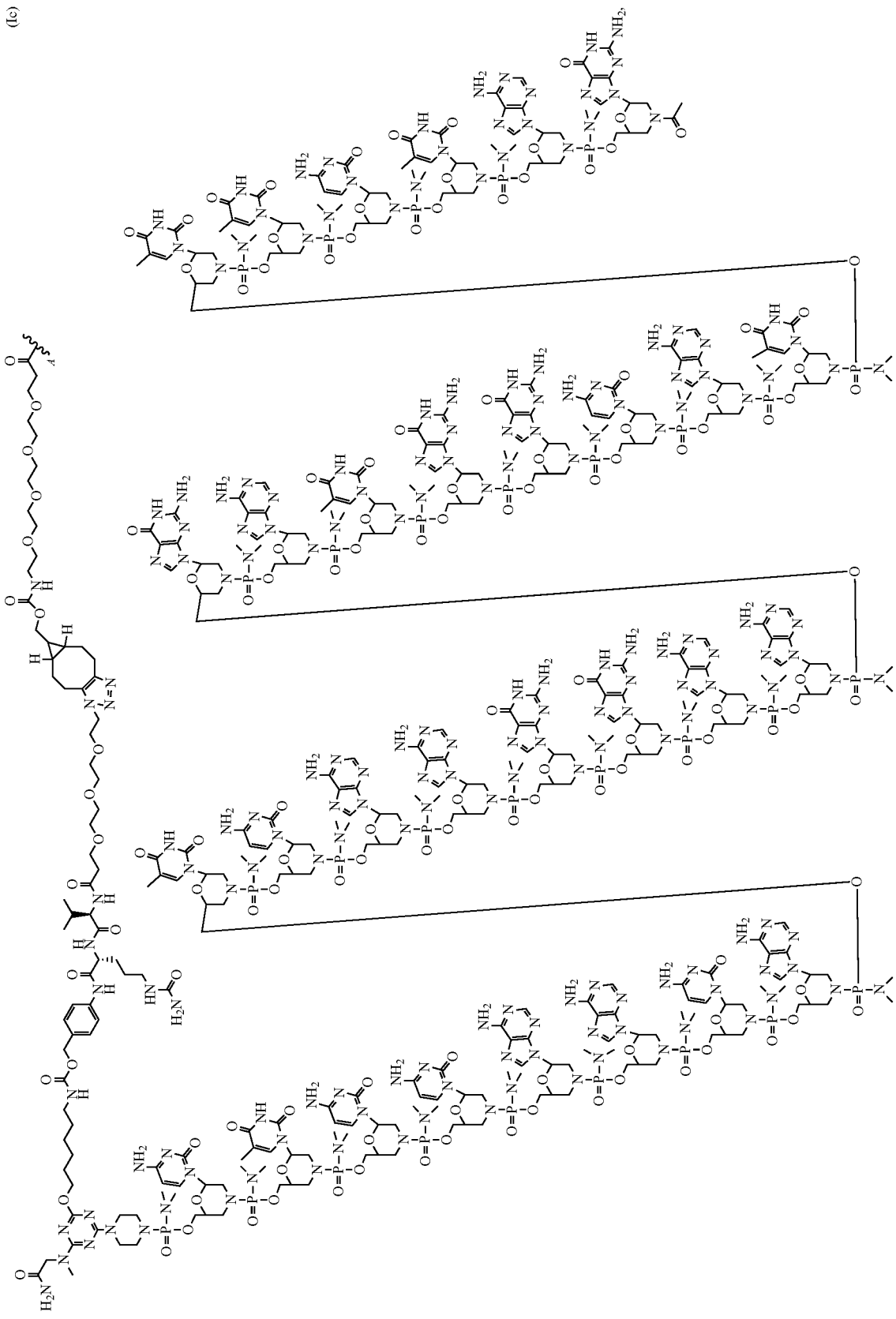

wherein R¹ is covalently linked (e.g., indirectly or directly linked, e.g., directly linked) to R² at attachment point A. In some embodiments, in each complex n1 is independently an integer (e.g., of one or greater) representing the number of instances of R¹ in each complex. In some embodiments, R² comprises an antibody comprising a sequence as set forth in Table 2. For example, in some embodiments, R² comprises an antibody comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, R² comprises an antibody comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, R² comprises an antibody comprising a VH comprising the amino acid sequence of SEQ ID NO: 17 and/or comprising a VL comprising the amino acid sequence of SEQ ID NO: 18. In some embodiments, R² comprises an antibody comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, R² comprises an antibody comprising a heavy chain comprising the amino acid sequence of SEQ ID NO: 19 and/or comprising a light chain comprising the amino acid sequence of SEQ ID NO: 20. In some embodiments, R² comprises an antibody that is a Fab fragment, a full-length IgG, a Fab' fragment, a F(ab')₂ fragment, an scFv, or an Fv. In some embodiments, R² comprises an antibody that is a Fab fragment. In some embodiments, in each complex n1 is independently an integer (e.g., an integer in the range of 1-27, 1-26, 1-10, 1-5, or 1-3). In some embodiments, R² comprises a Fab and each R¹ is covalently linked at attachment point A to a different amino acid residue of the Fab, optionally wherein each different amino acid residue is a lysine. In some embodiments, formulations described herein further comprise complexes that comprise a structure of formula (I): $[R^1]_{n1}$—$R^2$, wherein n1 is 0. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, formulations provided herein comprise complexes that comprise a structure of formula (Id):

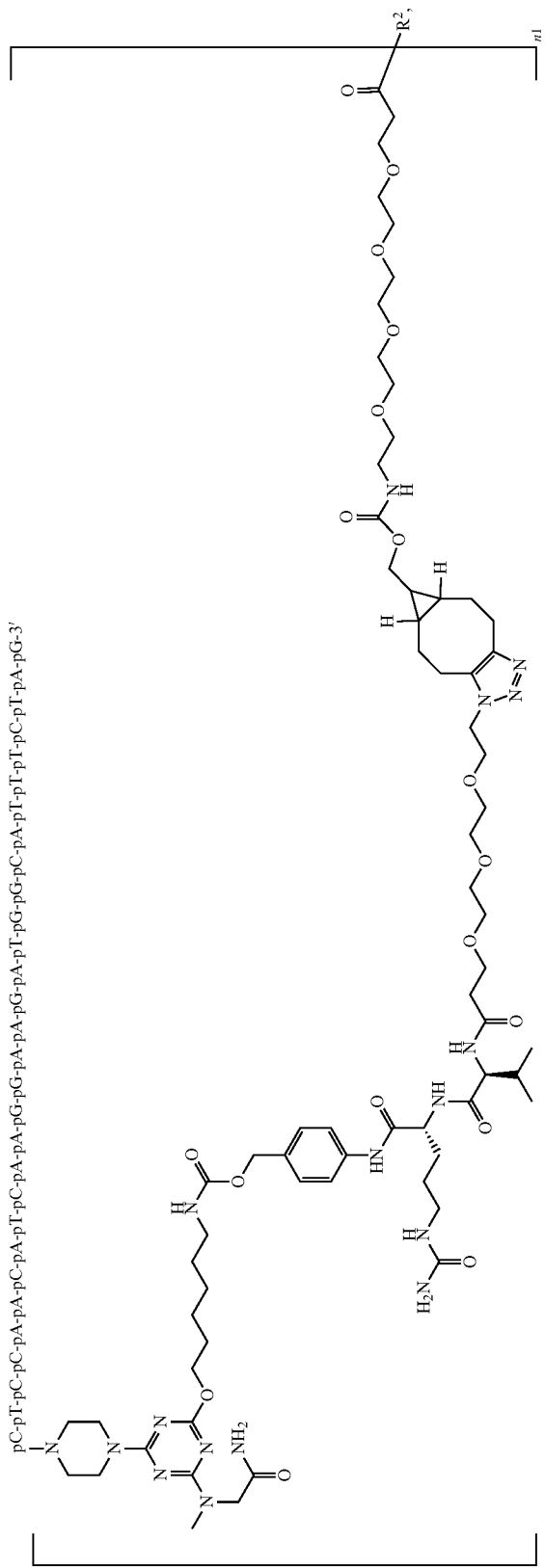

in which -pN indicates a base position of a phosphorodiamidate morpholino oligomer (PMO); wherein -p reflects a phosphorodiamidate linkage, and wherein N corresponds to a nucleobase of adenine (A), cytosine (C), guanine (G), or thymine (T), such that the PMO comprises a base sequence of CTCCAACATCAAGGAAGATGGCATTTCTAG (SEQ ID NO: 21); wherein $R^2$ comprises an antibody comprising a sequence as set forth in Table 2; wherein in each complex n1 is independently an integer (e.g., of one or greater) representing the number of instances of the group enclosed by square brackets, wherein each instance of the group enclosed by square brackets is covalently linked to a different amino acid residue of the antibody (e.g., Fab), optionally wherein each different amino acid residue is a lysine. In some embodiments, $R^2$ comprises an antibody (e.g., a Fab) comprising a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprising a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, $R^2$ comprises an antibody (e.g., a Fab) comprising a heavy chain variable region (VH) comprising an amino acid sequence at least 85% (e.g., at least 95%) identical to SEQ ID NO: 17 and/or comprising a light chain variable region (VL) comprising an amino acid sequence at least 85% (e.g., at least 95%) identical to SEQ ID NO: 18. In some embodiments, $R^2$ comprises an antibody (e.g., a Fab) comprising a VH comprising the amino acid sequence of SEQ ID NO: 17 and/or comprising a VL comprising the amino acid sequence of SEQ ID NO: 18. In some embodiments, $R^2$ comprises an antibody (e.g., a Fab) comprising a heavy chain comprising an amino acid sequence at least 85% (e.g., at least 95%) identical to SEQ ID NO: 19 and/or comprising a light chain comprising an amino acid sequence at least 85% (e.g., at least 95%) identical to SEQ ID NO: 20. In some embodiments, $R^2$ comprises an antibody (e.g., a Fab) comprising a heavy chain comprising the amino acid sequence of SEQ ID NO: 19 and/or comprising a light chain comprising the amino acid sequence of SEQ ID NO: 20. In some embodiments, in each complex n1 is independently an integer (e.g., an integer in the range of 1-27, 1-26, 1-10, 1-5, or 1-3). In some embodiments, $R^2$ comprises an antibody (e.g., a Fab) that is covalently linked via different amino acid residue of the antibody (e.g., Fab), optionally wherein each different amino acid residue is a lysine. In some embodiments, formulations described herein further comprise complexes in which n1 is 0. In some embodiments, the average value of n1 of complexes of the composition is in the range of 1 to 5 (e.g., 1-5, 1-4, 1-3, 1-2, 2-4, 3-5, 1-4.6, 1-4.5, 1-4.4, 1-4.3, 1-4.2, 1-3.5, 1-2.5, 1.1-5, 1.1-4.5, 1.1-4, 1.1-3.5, 1.1-3, 1.1-2.5, 1.1-2.2, 1.2-5, 1.2-4.5, 1.2-4, 1.2-3.5, 1.2-3, 1.2-2.5, 1.2-2.2, 1.3-5, 1.3-4.5, 1.3-4, 1.3-3.5, 1.3-3, 1.3-2.5, 1.3-2.2, 1.4-5, 1.4-4.5, 1.4-4, 1.4-3.5, 1.4-3, 1.4-2.5, 1.4-2.2, 1.5-5, 1.5-4.5, 1.5-4, 1.5-3.5, 1.5-3, 1.5-2.5, 1.5-2.2, 1.6-3, 1.6-2.5, 1.6-2.2, 1.7-3, 1.7-2.5, 1.7-2.2, 1.8-3, 1.8-2.5, or 1.8-2.2).

In some embodiments, complexes provided in the formulations described herein comprise a structure of formula (A):

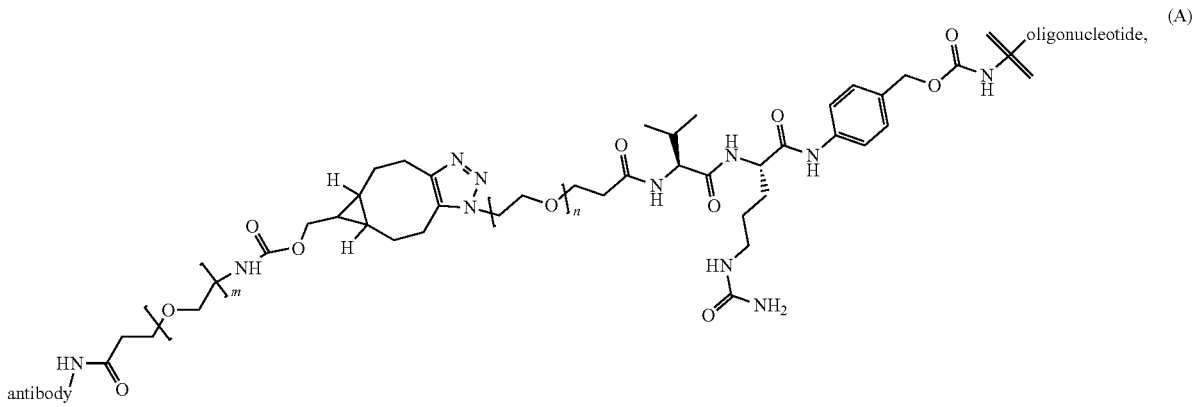

wherein y is 0-15 (e.g., 3) and z is 0-15 (e.g., 4). In some embodiments, the antibody is an anti-TfR1 antibody (e.g., the anti-TfR1 antibody provided in Table 2). In some embodiments, the oligonucleotide is a PMO and comprises the base sequence of SEQ ID NO: 21. In some embodiments, the amide shown adjacent to the anti-TfR1 antibody in the structure (A) results from a reaction with an amine of the antibody, such as a lysine epsilon amine. In some embodiments, a complex described herein comprises an anti-TfR1 Fab covalently linked via a lysine of the Fab to the 5' end of a PMO. In some embodiments, the antibody comprises a sequence as set forth in Table 2. For example, in some embodiments, the antibody comprises a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14; and/or comprises a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5, or 11, and a light chain complementarity determining region 3 (CDR-L3) comprising a sequence as set forth in SEQ ID NO: 6 or 16. In some embodiments, the antibody comprises a heavy chain variable region (VH) comprising an amino acid sequence at least 85% (e.g., at least 95%) identical to SEQ ID NO: 17 and/or comprises a light chain variable region (VL) comprising an amino acid sequence at least 85% (e.g., at least 95%) identical to SEQ ID NO: 18. In some embodiments, the antibody comprises a VH comprising the amino acid sequence of SEQ ID NO: 17 and/or comprises a VL comprising the amino acid sequence of SEQ ID NO: 18. In some embodiments, the antibody comprises a heavy chain comprising an amino acid sequence at least 85% (e.g., at least 95%) identical to SEQ ID NO: 19 and/or comprises a light chain comprising an amino acid sequence at least 85% (e.g., at least 95%) identical to SEQ ID NO: 20. In some embodiments, the antibody comprises a heavy chain comprising the amino acid sequence of SEQ ID NO: 19 and/or comprises a light chain comprising the amino acid sequence of SEQ ID NO: 20. In some embodiments, the antibody is a Fab fragment, a full-length IgG, a Fab' fragment, a F(ab')$_2$ fragment, an scFv, or an Fv.

In some embodiments, provided is a formulation comprising complexes described herein wherein a concentration of the complexes in the formulation therein is between 1-50 mg/mL of the complex, optionally 10-50 mg/ml or 20-35 mg/mL (e.g., 1-10 mg/mL, 10-15 mg/mL, 15-20 mg/mL, 20-22 mg/mL, 22-24 mg/ml, 24-26 mg/ml, 24-25 mg/ml, 25-26 mg/ml, 22-25 mg/mL, 25-27 mg/mL, 27-29 mg/mL, 29-30 mg/mL, 25-30 mg/mL, 29-31 mg/ml, 30-31 mg/ml, 31-32 mg/ml, 30-32 mg/mL, 32-33 mg/ml, 32-35 mg/mL, 30-35 mg/mL, 35-40 mg/mL, 40-45 mg/mL, 45-50 mg/mL), optionally approximately 25 mg/mL (e.g., 25 mg/mL) or approximately 30 mg/mL (e.g., 30 mg/mL).

In some embodiments, any one or a plurality of the complexes described herein is formulated with the histidine (e.g., L-histidine) and the sucrose in a lyophilized form (e.g., lyophilized powder).

In some embodiments, any one or a plurality of the complexes described herein is formulated with the histidine (e.g., L-histidine) and the sucrose in an aqueous solution. In some embodiments, the histidine (e.g., L-histidine) is present in the aqueous solution at a concentration in the range of 10-50 mM, 10-20 mM, 20 mM to 30 mM, or 20 mM to 40 mM, e.g., 20-22 mM, 22-24 mM, 24-25 mM, 25-26 mM, 24-26 mM, 26-27 mM, 24-27 mM, 27-28 mM, 28-29 mM, 29-30 mM, 27-30 mM, approximately 22-27 mM, approximately 23-26 mM, approximately 24-26 mM, approximately 26-28 mM, approximately 28-30 mM, approximately 30-32 mM, approximately 32-35 mM, approximately 35-40 mM, 40-45 mM, 45-50 mM, approximately 25 mM, or optionally, 25 mM. In some embodiments, the sucrose is present in the aqueous solution at a concentration in the range of 5% to 15% weight per volume (w/v %), for example, 8-15% w/v %, 9-15% w/v %, 9-11% w/v %, 9.5-11% w/v %, or for example, in the range of 5-6 w/v %, 6-7 w/v %, 7-8 w/v %, 8-9 w/v %, 9-10 w/v %, 10-11 w/v %, 11-12% w/v %, 10-12 w/v %, 12-13% w/v %, 13-14% w/v %, 12-14 w/v %, 14-15 w/v %, or 8-12 w/v %. In some embodiments, the sucrose is present in the aqueous solution at a concentration in the range of 8-12 w/v % (e.g., 10 w/v %). In some embodiments, the aqueous solution has a pH in the range of 5.0 to 7.0, for example, 5.0-5.2, 5.2-5.4, 5.4-5.6, 5.6-5.8, 5.8-6.0, 5.9-6.0, 5.9-6.1, 6.0-6.1; for example, 5.5 to 6.5, or for example, in the pH range of 5.5-5.8, 5.8-6.0, 5.9-6.1, 6.0-6.1, 6.0-6.2, 6.2-6.4, 6.4-6.5, 6.5-6.7, 6.7-6.8, 6.8-6.9, 6.9-7.0, 7.0-7.1, or 5.8-6.2. In some embodiments, the aqueous solution has a pH in the range of 5.8-6.2 (e.g., 5.8-6.0, 5.8-6.1, 5.9-6.1). In some embodiments, the aqueous solution has a pH in the range of 5.9-6.2. In some embodiments, the aqueous solution has a pH in the range of 6.0-6.1 (e.g., about 6.0, or 6.0).

In some embodiments, provided is a formulation (e.g., in aqueous solution) described herein comprising one or a plurality of complexes, histidine, and sucrose, In some embodiments, any one of the formulations described herein is an aqueous solution, wherein the histidine (e.g., L-histidine) is present in the aqueous solution at a concentration of 25 mM, wherein the sucrose is present in the aqueous solution at a concentration of 10 w/v %, and wherein the aqueous solution is at a pH of about 6.0 (e.g., 6.0, 5.9-6.1).

In some embodiments, provided is a formulation (e.g., in aqueous solution) described herein comprising a plurality of complexes, histidine, and sucrose, wherein the histidine (e.g., L-histidine) is present in the aqueous solution at a concentration of 25 mM, wherein the sucrose is present in the aqueous solution at a concentration of 10 w/v %, and wherein the pH of about 6.0 (e.g., 6.0, 5.9-6.1), and the concentration of complexes in the formulation is 10-50 mg/ml or 20-35 mg/mL (e.g., 1-10 mg/mL, 10-15 mg/mL, 15-20 mg/mL, 20-22 mg/mL, 22-24 mg/ml, 24-26 mg/ml, 22-25 mg/mL, 25-27 mg/mL, 27-29 mg/mL, 29-31 mg/ml, 29-30 mg/mL, 30-31 mg/ml, 31-32 mg/ml, 25-30 mg/mL, 30-32 mg/mL, 32-35 mg/mL, 30-35 mg/mL, 35-40 mg/mL, 40-45 mg/mL, 45-50 mg/mL), optionally 25 mg/mL or 30 mg/mL.

As described herein, in some embodiments, formulations provided herein comprise sucrose. In some embodiments, sucrose serves at least in part as a lyoprotectant. In some embodiments, the sucrose is from a plant, e.g., grass, fruit, or vegetable (e.g., root vegetable) source (e.g., beet (e.g., sugar beet, for example, *Saccharum* spp.)), sugarcane (e.g., *Beta vulgaris*), dates, sugar maple, sweet sorghum, apples, oranges, carrots, molasses, maple syrup, corn sweeteners) or animal product (e.g., honey). In some embodiments, the sucrose is from beet or sugarcane (e.g., beet sucrose, sugarcane sucrose). In some embodiments, a lyoprotectant other than sucrose may be used, e.g., trehalose, mannitol, lactose, polyethylene glycol, or polyvinyl pyrrolidone. However, in some embodiments, a collapse temperature modifier (e.g., dextran, ficoll, or gelatin) may be provided in a formulation.

In some embodiments, any one or a plurality of the complexes described herein is formulated with histidine and sucrose in a lyophilized form (e.g., lyophilized powder). In some embodiments, the lyophilized form (e.g., lyophilized powder) is obtained by lyophilization of any one of the aqueous solutions described herein.

In some embodiments, provided is a product (e.g., lyophilized formulation described herein), produced by a process comprising lyophilizing an aqueous solution of a formulation (e.g., in aqueous form) described herein.

In some embodiments, any one or a plurality of the complexes described herein is formulated with histidine and sucrose in a frozen form (e.g., a frozen aqueous solid). In some embodiments, the frozen form (e.g., frozen aqueous solid) is obtained by freezing of any one of the aqueous solutions described herein. A frozen form may be frozen to a temperature of less than -20° C. (e.g., less than −20° C., less than −30° C., less than −40° C., less than −50° C., less than −60° C., less than −70° C., less than −80° C., or lower).

In some embodiments, provided is a product (e.g., frozen formulation described herein), produced by a process comprising freezing an aqueous solution of a formulation (e.g., in aqueous form) described herein.

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Methods of Use/Treatment

Complexes comprising an anti-TfR1 antibody (e.g., Fab) covalently linked to a molecular payload (e.g., oligonucleotide, e.g., phosphorodiamidate morpholino oligomer (PMO)) as described herein are effective in treating a subject having a dystrophinopathy, e.g., Duchenne Muscular Dystrophy. In some embodiments, complexes comprise a molecular payload that is an oligonucleotide, e.g., an antisense oligonucleotide that facilitates exon skipping of an mRNA expressed from a mutated DMD allele.

In some embodiments, a subject may be a human subject, a non-human primate subject, a rodent subject, or any suitable mammalian subject. In some embodiments, the non-human primate subject is a cynomolgus monkey. In some embodiments, the subject is human. In some embodiments, the subject is a human subject that is between 2-60 (e.g., 2-60, 2-50, 2-40, 2-30, 2-20, 2-10) years of age. In some embodiments, the subject is a human subject that is between 5-30 (e.g., 5, 6, 7, 8, 9, 10, 11, 12, 13, 14, 15, 16, 17, 18, 19, 20, 21, 22, 23, 24, 25, 26, 27, 28, 29, or 30) years old. In some embodiments, the subject is a human subject that is between 5-12 (e.g., 5, 6, 7, 8, 9, 10, 11, or 12) years of age. In some embodiments, the subject is a human subject that is between 4-16 (e.g., 4-16, 5-16, 6-16, 7-16, 8-16, 9-16, 10-16, 11-16, 12-16, 13-16, 14-16, 15-16, 4-15, 5-15, 6-15, 7-15, 8-15, 9-15, 10-15, 11-15, 12-15, 13-15, 14-15, 4-14, 5-14, 6-14, 7-14, 8-14, 9-14, 10-14, 11-14, 12-14, 13-14, 4-13, 5-13, 6-13, 7-13, 8-13, 9-13, 10-13, 11-13, 12-13, 4-12, 5-12, 6-12, 7-12, 8-12, 9-12, 10-12, 11-12, 4-11, 5-11, 6-11, 7-11, 8-11, 9-16, 10-11, 4-10, 5-10, 6-10, 7-10, 8-10, 9-10, 4-9, 5-9, 6-9, 7-9, 8-9, 4-9, 5-9, 6-9, 7-9, 8-9, 4-8, 5-8, 6-8, 7-8, 4-7, 5-7, 6-7, 4-6, 5-6, or 4-5) years of age. In some embodiments, the subject is a human subject that is about 4, 5, 6, 7, 8, 9, 10, 11, 12, 13, 14, 15, or 16 years of age.

In some embodiments, a subject may have Duchenne muscular dystrophy or other dystrophinopathy. In some embodiments, a subject has a mutated DMD allele, which may optionally comprise at least one mutation in a DMD exon that causes a frameshift mutation and leads to improper RNA splicing/processing. In some embodiments, a subject is suffering from symptoms of a severe dystrophinopathy, e.g., muscle atrophy or muscle loss. In some embodiments, a subject has an asymptomatic increase in serum concentration of creatine phosphokinase (CK) and/or (e.g., and) muscle cramps with myoglobinuria. In some embodiments, a subject has a progressive muscle disease, such as Duchenne or Becker muscular dystrophy or DMD-associated dilated cardiomyopathy (DCM). In some embodiments, a subject is not suffering from symptoms of a dystrophinopathy. In some embodiments, a subject is ambulant. In some embodiments, a subject is non-ambulant.

In some embodiments, a subject has a mutation in a DMD gene that is amenable to exon 51 skipping. In some embodiments, a complex as described herein is effective in treating a subject having a mutation in a DMD gene that is amenable to exon 51 skipping. In some embodiments, a complex comprises an oligonucleotide, e.g., an oligonucleotide that facilitates skipping of exon 51 of a pre-mRNA, such as in a pre-mRNA encoded from a mutated DMD gene (e.g., a mutated DMD gene that is amenable to exon 51 skipping).

An aspect of the disclosure includes methods involving administering to a subject a formulation comprising an effective amount of complex(es) as described herein. In some embodiments, an effective amount of a pharmaceutical composition that comprises complex(es) comprising an antibody (e.g., Fab) described herein covalently linked to an oligonucleotide (e.g., PMO) described herein can be administered to a subject in need of treatment. In some embodiments, a pharmaceutical composition is administered systemically. In some embodiments, a pharmaceutical composition comprising complex(es) as described herein may be administered by a suitable route, which may include intravenous administration, e.g., as a bolus or by continuous infusion over a period of time. In some embodiments, administration may be performed by intravenous, intramuscular, intraperitoneal, intracerebrospinal, subcutaneous, intra-articular, intrasynovial, or intrathecal routes. In some embodiments, a pharmaceutical composition comprising complex(es) as described herein is administered by infusion (e.g., intravenous infusion). In some embodiments, a pharmaceutical composition comprising a plurality of complexes described herein may be in solid form, aqueous form, or a liquid form. In some embodiments, an aqueous or liquid form may be nebulized or lyophilized. In some embodiments, a lyophilized form may be reconstituted with an aqueous or liquid solution.

In some embodiments, provided are methods of and/or uses for treating a subject having a mutated DMD allele associated with Duchenne Muscular Dystrophy, comprising administering to the subject a formulation comprising a complex or plurality of complexes described herein with an effective amount of the complex(es). In some embodiments, provided are methods of and/or uses for promoting the expression or activity of a dystrophin protein in a subject, the methods comprising contacting the cell with the formulation comprising a plurality of complexes described herein with an effective amount of the complex(es). In some embodiments, the dystrophin protein is a truncated dystrophin protein. The truncated dystrophin protein is functional (e.g., retains activities of a wild-type dystrophin protein). In some embodiments, the truncated dystrophin protein retains partial function of a wild-type dystrophin protein. In some embodiments, the method comprises administering a lyophilized form (e.g., lyophilized powder) of a formulation comprising a plurality of complexes described herein, comprising reconstituting a lyophilized form of the formulation in an aqueous solution, and administering the aqueous solution of the formulation to a subject in need thereof. For example, in some embodiments, a lyophilized form of the formulation comprising a complex or plurality of complexes is shipped and/or stored in the lyophilized form, reconstituted at a location for administering the aqueous solution of the formulation (e.g., healthcare provider location), and administered in the reconstituted form (e.g., as an aqueous solution) by injection or intravenously, e.g., by infusion. In some embodiments, the subject has a mutated DMD allele comprises a mutation amenable to exon 51 skipping. In some embodiments, the mutated DMD allele comprises a frameshift mutation in exon 51.

In some embodiments, a pharmaceutical composition is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising an anti-TfR1 antibody (e.g., a Fab) covalently linked to a molecular payload (e.g., oligonucleotide, e.g., phosphorodiamidate morpholino oligomer (PMO)) is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex(es) in a subject, generally will contribute to determination of the concentration of pharmaceutical composition that is used for treatment. The frequency of administration may be empirically determined and adjusted to maximize the efficacy of the treatment. The efficacy of treatment may be assessed using any suitable methods. In some embodiments, the efficacy of treatment may be assessed by evaluation or observation of symptoms associated with a dystrophinopathy, e.g. muscle atrophy or muscle weakness, through measures of a subject's self-reported outcomes, e.g. mobility, self-care, usual activities, pain/discomfort, and anxiety/depression, or by quality-of-life indicators, e.g. lifespan. In some embodiments, a pharmaceutical composition that comprises a complex comprising a muscle-targeting agent covalently linked to a molecular payload described herein is administered to a subject at an effective concentration sufficient to modulate activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

EXAMPLES

Example 1. Exon-Skipping Activity of Anti-TfR1 Conjugates in Duchenne Muscular Dystrophy Patient Myotubes This study evaluated the exon-skipping activities of anti-TfR1 conjugates comprising the anti-TfR1 Fab having the VH and VL sequences shown in Table 2 covalently linked (through lysine conjugation) via a linker comprising a Valine-Citrulline sequence to a DMD exon 51-skipping antisense oligonucleotide (ASO). The DMD exon 51-skipping ASO is a PMO and comprises the nucleotide sequence of SEQ ID NO: 21. The conjugates comprise a structure of:

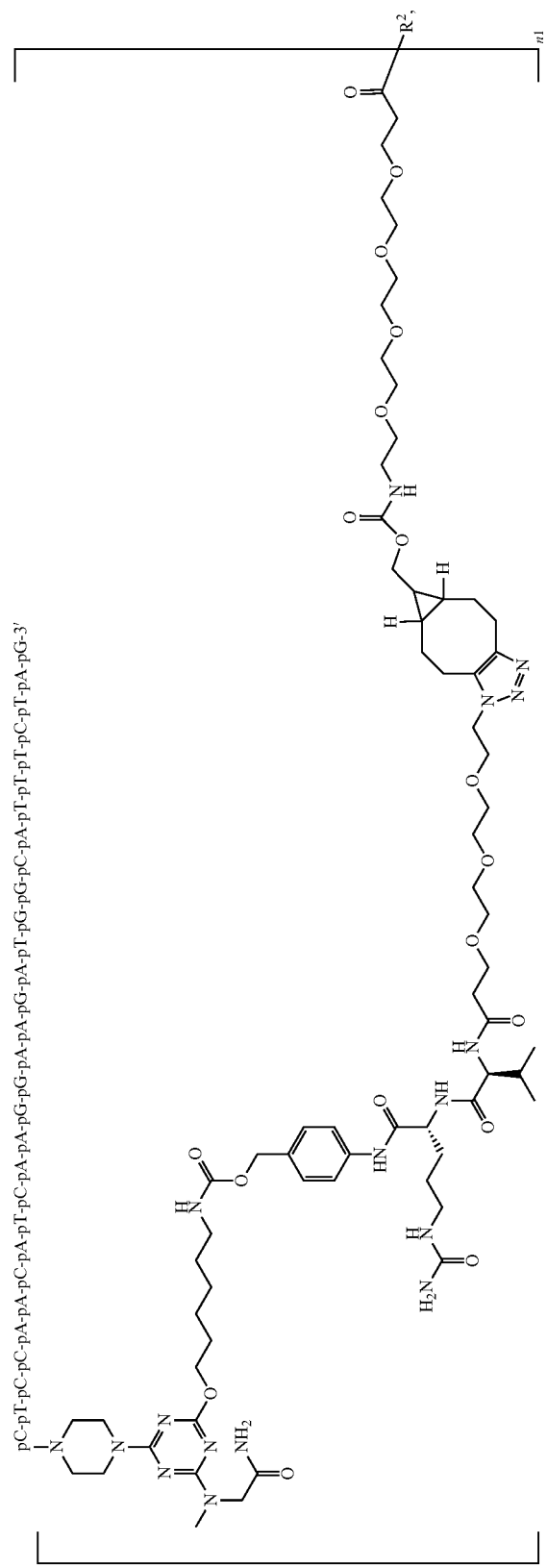

wherein $R^2$ is the anti-TfR1 Fab shown in Table 2, and wherein in each conjugate n1 is independently an integer of zero or greater.

Immortalized human myoblasts bearing an exon 52 deletion were thawed and seeded at a density of $1 \times 10^6$ cell/flask in Promocell Skeletal Cell Growth Media (with 5% FBS and 1× Pen-Strep) and allowed to grow to confluency. Once confluent, cells were trypsinized and pelleted via centrifugation and resuspended in fresh Promocell Skeletal Cell Growth Media. The cell number was counted and cells were seeded into Matrigel-coated 96-well plates at a density of 50 k cells/well. Cells were allowed to recover for 24 hours. Cells were induced to differentiate by aspirating the growth media and replacing with differentiation media with no serum. Cells were then treated with the DMD exon 51-skipping oligonucleotide (not covalently linked to an antibody -"naked") at a concentration of 10 µM oligonucleotide or treated with the conjugate to a final concentration of 10 µM oligonucleotide equivalent. Cells were incubated with test articles for ten days then total RNA was harvested from the 96 well plates. cDNA synthesis was performed on 75 ng of total RNA, and mutation specific PCRs were performed to evaluate the degree of exon 51 skipping in each cell type. Mutation-specific PCR products were run on a 4% agarose gel and visualized using SYBR gold. Densitometry was used to calculate the relative amounts of the skipped and unskipped amplicon and exon skipping was determined as a ratio of the Exon 51 skipped amplicon divided by the total amount of amplicon present:

$$\% \text{ Exon Skipping} = \frac{\text{Skipped Amplicon}}{(\text{Skipped Amplicon} + \text{Unskipped Amplicon})} * 100$$

The results demonstrate that the conjugates resulted in enhanced exon skipping compared to the same DMD exon 51-skipping oligonucleotide that is not covalently linked to an antibody in patient myotubes (FIG. 1). This indicates that an anti-TfR1 Fab (e.g., having a sequence set forth in Table 2) facilitated cellular internalization of the conjugate into muscle cells resulting in activity of the exon 51-skipping oligonucleotide in the muscle cells. Similarly, an anti-TfR1 antibody can facilitate internalization of a conjugate comprising the anti-TfR1 antibody covalently linked to other exon skipping oligonucleotides (e.g., an exon skipping oligonucleotide provided herein, such as an exon 51 skipping oligonucleotide) into muscle cells and facilitate activity of the exon skipping oligonucleotide in the muscle cells.

Example 2. Exon Skipping Activity of Anti-TfR1 Fab-ASO Conjugate In Vivo in Cynomolgus Monkeys The anti-TfR1 oligonucleotide conjugates described in Example 1 were tested for their exon skipping activity in vivo in healthy non-human primates. Naïve male cynomolgus monkeys (n=4-5 per group) were administered two doses of vehicle, 30 mg/kg naked ASO (i.e., not covalently linked to an antibody), or 122 mg/kg anti-TfR1 Fab covalently linked to the DMD exon 51-skipping oligonucleotide (30 mg/kg ASO equivalent) via intravenous infusion on days 1 and 8. Animals were sacrificed and tissues harvested either 2 weeks or 4 weeks after the first dose was administered. Total RNA was collected from tissue samples using a Promega Maxwell® RSC instrument and cDNA synthesis was performed using qScript cDNA SuperMix. Assessment of exon 51 skipping was performed using end-point PCR.

Capillary electrophoresis of the PCR products was used to assess exon skipping, and % exon 51 skipping was calculated using the following formula:

$$\% \text{ Exon Skipping} = \frac{\text{Molarity of Skipped Band}}{\text{Molarity of Skipped Band} + \text{Molarity of Unskipped Band}} * 100.$$

Calculated exon 51 skipping results are shown in Table 4.

TABLE 4

Exon 51 skipping of DMD in cynomolgus monkey DMD

| | | Time | | | |
|---|---|---|---|---|---|
| | | 2 weeks | | 4 weeks | |
| | | Group | | | |
| | Vehicle | ASO alone[a] | Conjugate | ASO alone[a] | Conjugate |
| Conjugate dose[b] | 0 | n/a | 122 | n/a | 122 |
| ASO alone Dose[c] | 0 | 30 | 30 | 30 | 30 |
| Quadriceps [d] | 0.00 | 1.216 | 4.906 | 0.840 | 1.708 |
| | (0.00) | (1.083) | (3.131) | (1.169) | (1.395) |
| Diaphragm [d] | 0.00 | 1.891 | 7.315 | 0.717 | 9.225 |
| | (0.00) | (2.911) | (1.532) | (1.315) | (4.696) |
| Heart [d] | 0.00 | 0.043 | 3.42 | 0.00 | 4.525 |
| | (0.00) | (0.096) | (1.192) | (0.00) | (1.400) |
| Biceps [d] | 0.00 | 0.607 | 3.129 | 1.214 | 4.863 |
| | (0.00) | (0.615) | (0.912) | (1.441) | (3.881) |
| Tibialis anterior [d] | 0.00 | 0.699 | 1.042 | 0.384 | 0.816 |
| | (0.00) | (0.997) | (0.685) | (0.615) | (0.915) |
| Gastrocnemius [d] | 0.00 | 0.388 | 2.424 | 0.00 | 5.393 |
| | (0.00) | (0.573) | (2.329) | (0.00) | (2.695) |

[a]ASO = antisense oligonucleotide.
[b]Conjugate doses are listed as mg/kg of anti-TfR1 Fab-ASO conjugate.
[c]ASO doses are listed as mg/kg ASO equivalent of the anti-TfR1 Fab-ASO dose.
[d] Exon skipping values are mean % exon 51 skipping with standard deviations (n = 5) in parentheses.

Tissue ASO accumulation was also quantified using a hybridization ELISA with a probe complementary to the ASO sequence. A standard curve was generated and ASO levels (in ng/g) were derived from a linear regression of the standard curve. The ASO was distributed to all tissues evaluated at a higher level following the administration of the anti-TfR1 Fab-ASO conjugate as compared to the administration of unconjugated ASO (not covalently linked to antibody). Intravenous administration of unconjugated ASO resulted in levels of ASO that were close to background levels in all tissues evaluated at 2 and 4 weeks after the first dose was administered. Administration of the conjugate resulted in distribution of ASO through the tissues evaluated with a rank order of heart>diaphragm>bicep>quadriceps>gastrocnemious>tibialis anterior 2 weeks after first dosing. The duration of tissue concentration was also assessed. ASO levels were detectable at 4 weeks post dose in all tissues (Table 5). This indicates that the anti-TfR1 Fab shown in Table 2 enabled cellular internalization of the conjugate into muscle cells in vivo, resulting in activity of the exon skipping oligonucleotide in the muscle cells.

TABLE 5

Tissue distribution of DMD exon 51 skipping ASO in cynomolgus monkeys

| | Time | | | |
|---|---|---|---|---|
| | 2 weeks | | 4 weeks | |
| | Group | | | |
| | Vehicle | ASO alone[a] | Conjugate | ASO alone[a] | Conjugate |
|---|---|---|---|---|---|
| Conjugate Dose[b] | 0 | n/a | 122 | n/a | 122 |
| ASO alone Dose[c] | 0 | 30 | 30 | 30 | 30 |
| Quadriceps[d] | 0 (59.05) | 696.8 (868.15) | 2436 (954.0) | 197 (134) | 682 (281) |
| Diaphragm[d] | 0± (144.3) | 580.02 (360.11) | 6750 (2256) | 60 (120) | 3131 (1618) |
| Heart[d] | 0 (396.03) | 1449 (1337) | 27138 (6315) | 943 (1803) | 30410 (9247) |
| Biceps[d] | 0 (69.58) | 615.63 (335.17) | 2840 (980.31) | 130 (80) | 1326 (623) |
| Tibialis anterior[d] | 0 (76.31) | 564.71 (327.88) | 1591 (253.50) | 169 (110) | 1087 (514) |
| Gastrocnemius[d] | 0 (41.15) | 705.47 (863.75) | 2096 (474.04) | 170 (69) | 1265 (272) |

[a] ASO = Antisense oligonucleotide.
[b] Conjugate doses are listed as mg/kg of anti-TfR1 Fab-ASO conjugate.
[c] ASO doses are listed as mg/kg ASO or ASO equivalent of the anti-TfR1 Fab-ASO conjugate dose.
[d] ASO values are mean concentrations of ASO in tissue as ng/g with standard deviations (n = 5) in parentheses.

Example 3. Comparison of Freeze-Thaw Stability Tests of Different Exemplary Formulations The following formulations were prepared. The formulation comprises the anti-TfR1 Fab having the VH/VL sequences shown in Table 2 covalently linked (through lysine conjugation) via a linker comprising a Valine-Citrulline sequence to a DMD exon 51-skipping ASO, wherein the anti-TfR1 Fab-ASO conjugate was at a concentration of 25 mg/ml, in a 2 mL glass vial with 500 µL fill volume. The DMD exon 51-skipping ASO is a PMO and comprises the nucleotide sequence of SEQ ID NO: 21.
  Formulation 1: 25 mM histidine, 10% sucrose, pH 6
  Formulation 2: 25 mM histidine, 10% sucrose, pH 5.5
  Formulation 3: 25 mM histidine, 10% sucrose, pH 6.5
  Formulation 4: 25 mM histidine, 10% sucrose, 0.02% PS-80, pH 6
  Formulation 5: 10 mM histidine, 10% sucrose, pH 6
  Formulation 6: 50 mM histidine, 10% sucrose, pH 6
  Formulation 7: 25 mM histidine, 150 mM NaCl, pH 6
  Formulation 8: 25 mM phosphate, 150 mM NaCl, pH 7

The formulations were frozen at −80° C. and followed by thawing at ambient temperature (e.g., room temperature of approximately 20° C.), with 5×F/T (freeze/thaw) cycles, and held at 2-8° C. for 3-4 hours before analysis.

Formulation buffers prepared: The formulation drug substance (formulation with conjugate described herein) was buffer-exchanged with appropriate formulation buffer. Sartorius Vivaspin Filters were used (30 kDa MWCO). After 5 buffer changes, the anti-TfR1 Fab-ASO was concentrated to 25 mg/ml. The drug products were sterile filtered and loaded into the vials (a 700 µL fill was used for the vials). The sample formulations were visually observed at the following timepoints: T0 (week 0), T1 (week 1), T2 (week 2), T4 (week 4), T8 (week 8), and at the temperatures of −20° C., 2-8° C., 25° C., and 40° C.

At time points T0, T1, T2, T4, and T8, formulations 1-6 were observed to be clear and colorless, at all temperatures including −20° C., 2-8° C., 25° C., and 40° C. Formulations 7 and 8 were observed to be show precipitation with opalescence and particles, at all temperatures including −20° C., 2-8° C., 25° C., and 40° C.

Example 4. Analysis of Thermal Stability of Exemplary Formulation

The following formulation was prepared. The formulation comprises the anti-TfR1 Fab having the VH/VL sequences shown in Table 2 having the VH/VL sequences shown in Table 2 covalently linked (through lysine conjugation) via a linker comprising a Valine-Citrulline sequence to a DMD exon 51-skipping ASO (PMO comprising the nucleotide sequence of SEQ ID NO: 21), wherein the anti-TfR1 Fab-ASO conjugate was at a concentration of 25 mg/ml, in a 2 mL glass vial with 500 µL fill volume. In this formulation (Formulation 1) were: 25 mM histidine, 10% sucrose, pH 6.

Figure 2:
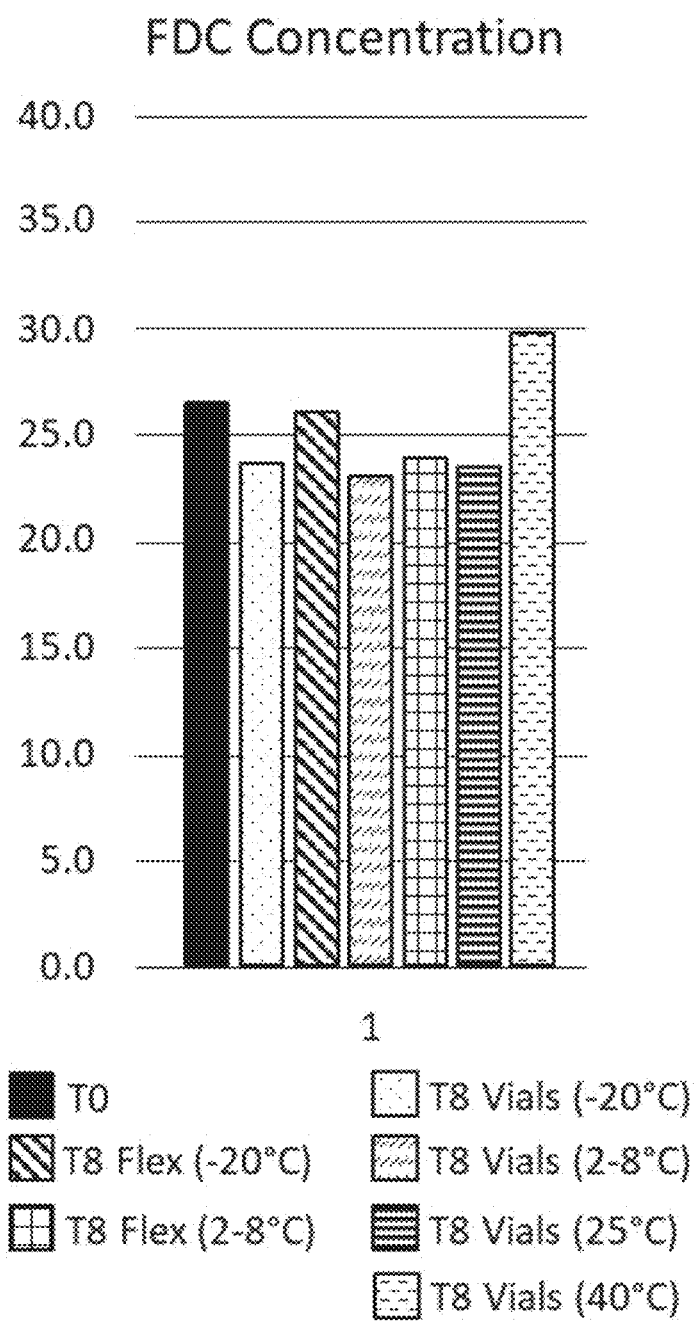
FIG. 2 shows the stability of a composition comprising conjugates comprising an anti-TfR1 Fab having the VH/VL sequences shown in Table 2 covalently linked (through lysine conjugation) via a linker comprising a valine-citrulline sequence to a DMD exon 51-skipping antisense oligonucleotide (ASO) (referred to as "conjugate 1") in Formulation 1 (25 mg/mL conjugate in 25 mM histidine, 10% sucrose, pH 6) with respect to the concentration of the conjugate over time.

Formulation buffers were prepared: The formulation drug substance (formulation with conjugate described herein) was buffer-exchanged with appropriate formulation buffer. Sartorius Vivaspin Filters were used (30 kDa MWCO). After 5 buffer changes, the anti-TfR1 Fab-ASO was concentrated to 25 mg/ml. The drug products were sterile filtered and loaded into the vials (a 700 µL fill was used for the vials). Next, an analysis of the thermal stability of the formulation described above in Example 4 ("Formulation 1") was conducted. This analysis shows the conjugate concentration of the anti-TfR1 Fab-ASO conjugate at the specified timepoints of T0 (week 0) and T8 (week 8)), and at the specified temperatures. See FIG. 2. Standard BCA (Bicinchoninic Acid) analysis was used to measure the protein conjugate concentration. BCA assay was carried out using standard procedure:
  1) Prepare Working Reagent (WR). 100 uL of WR is required for each sample in the microplate procedure. Prepare WR by mixing 50:1 (BCA reagent A: BCA reagent B) thoroughly. 10 mL of WR reagent is needed for a full 96 well plate. Therefore, combine 10 mL of Reagent A with 200 µL of Reagent B and ensure buffer is at RT and used within 90 minutes of mixing. It is recommended to use freshly made working solution.
  2) Prepare standard curve and dilution curve for unknown samples. 10 µL of standard or unknown sample is added to 200 µL of WR and incubated at 60° C. for 10 minutes. This is added to the first row of the plate and serial diluted 100 µL:100 µL in subsequent columns, 96-well clear plate: Standard: Known Fab: 15G11 (11 mg/mL). Prepare an 8-point standard curve and unknown sample dilution curve by doing 1:1 dilution for each point.
  3) Incubate for 5 minutes.
  4) Measure the absorbance at 480 nM on a plate reader.
  5) Use standard curve to determine the protein concentration of each unknown sample (6 dilutions were measured).

In Formulation 1, slight decreases in concentration of the conjugate were observed in different containers (2 mL glass vial with 600 µL fill volume referred to as "vial"; plastic Flexboy bag with a 1 mL fill volume referred to as "flex"), indicating overall stability of this formulation at specified temperatures and in the specified containers. Less of a conjugate concentration decrease from week 0 (T0) to the timepoint at week 8 (T8) was observed for formulations in the plastic Flexboy bag as compared to the glass vial for temperatures −20° C. and 2-8° C. However, at timepoint 8 (T8) for Formulation 1 in the glass vials at 40° C., no decrease in conjugate concentration was observed.

Example 5. Analysis of Material Adhesion to Container Types

A study was conducted to analyze material losses through adhesion of formulations, to evaluate possible adhesion to various plastics, comprising the exemplary anti-TfR1 Fab having the VH/VL sequences shown in Table 2 covalently linked (through lysine conjugation) via a linker comprising a Valine-Citrulline sequence to a DMD exon 51-skipping ASO (PMO comprising the nucleotide sequence of SEQ ID NO: 21). This TfR1 Fab-ASO conjugate formulated in Formulation 1 (25 mM histidine, 10% sucrose buffer (pH 6)) described in Example 3: showed less material loss. The study was conducted as follows: repeat the previous study of Example 3 at 25 mg/mL; add the formulations to the plastics and perform 1 freeze/thaw (F/T) cycle (freeze at −80° C. overnight, thaw at 2-8° C. for 4 hours); and analyze by standard tests, including Visual, BCA, SEC-HPLC (SEC). Following one freeze-thaw cycle at −80° C. as discussed, the concentration of the conjugate in Formulation 1 was measured. Standard BCA (Bicinchoninic Acid) analysis was used to measure the protein conjugate concentration, as disclosed in Example 4.

SEC-HPLC analytical method was as follows:
HPLC System Thermo Ultimate-3000 UHPLC system
Sample Concentration: 1 mg/mL (diluted with HPLC-grade water); Injection Volume: 10 μL
Buffer: 100 mM sodium phosphate, 100 mM NaCl, 15% Acetonitrile, pH 7.0
Run: Isocratic, 0.25 mL/min, 20 min
Column oven temperature: Ambient. Column: Waters AQUITY UPLC Protein BEH SEC Column 200 Å, 1.7 μm, 4.6×300 mm (P/N: 186005226)
Wavelengths: 280 nm and 260 nm Samples injected in duplicate, average values reported.

Figure 3:
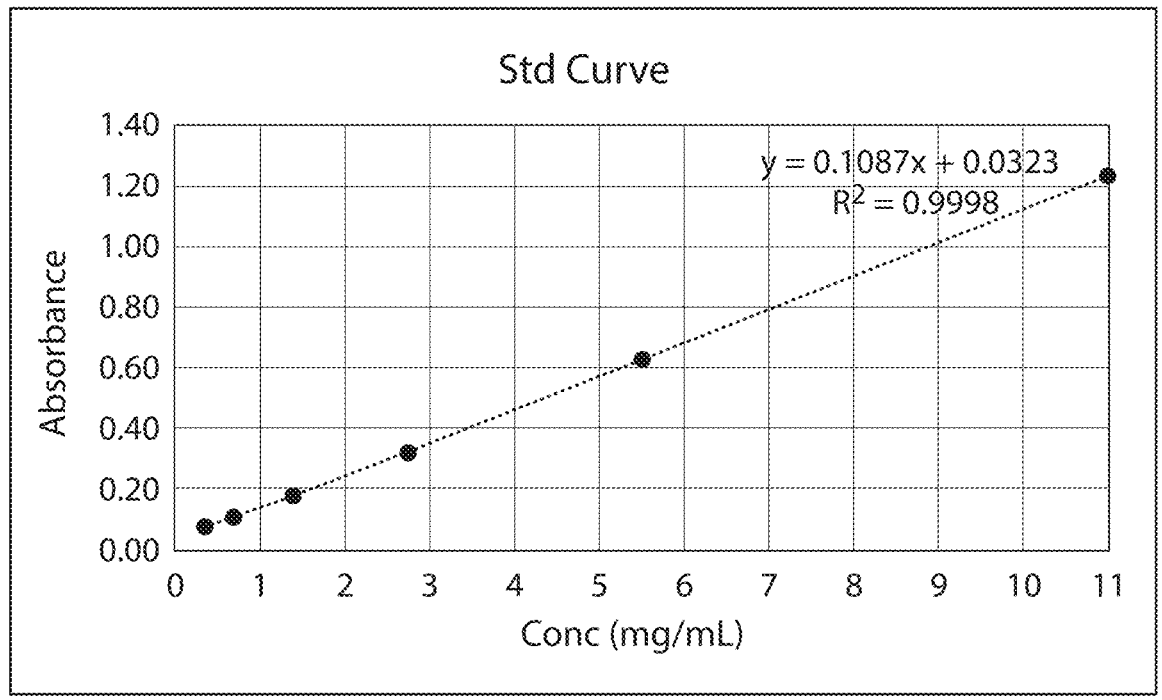
FIG. 3 shows BCA assay results of Formulation 1 comprising the anti-TfR1 Fab having the VH/VL sequences shown in Table 2 covalently linked (through lysine conjugation) via a linker comprising a valine-citrulline sequence to a DMD exon 51-skipping ASO ("conjugate 1"). Once the anti-TfR1 Fab-ASO conjugate 1 was at a 25 mg/mL concentration, samples of the conjugate were added to the desired containers (glass, EVA, PC, HDPE) and frozen at −80° C. overnight, then thawed at 2-8° C. for 4 hours. The standard curves were generated with an R² value of 0.9998. Concentrations of the samples were calculated based on this curve.

The strong stability and lack of surface adhesion to different plastic container types (ethylene vinyl acetate plastic (EVA), polycarbonates plastic (PC), High Density Poly Ethylene plastic (HDPE)) using the 25 mM histidine, 10% sucrose, pH 6.0 formulation of the conjugate is demonstrated collectively in FIGS. 3 and 4. FIGS. 3 and 4 show the good stability and lack of surface adhesion, demonstrated by a higher concentration of the conjugate in Formulation 1 for the plastic container types, as compared to the lower concentration of the conjugate for the glass container. FIG. 4 shows that via the SEC analysis, there were no significant changes in the composition of the HPLC peaks across all of the samples, including the sample with the 10 mg/ml glass standard (FDC conjugate which was at ~10 mg/mL, was stored in glass, and was subjected to one freeze thaw cycle (frozen from shipping and held at 2-8° C.)), and the 25 mg/ml samples in glass or specified plastics (25 mg/mL conjugate concentrated in spin filters, then added to the indicated plastics or glass and subjected to one F/T cycle).

The results of FIG. 4 indicate good stability of Formulation 1.

Additional Embodiments

1. A formulation comprising complexes that comprise a phosphorodiamidate morpholino oligomer (PMO) covalently linked to an anti-transferrin receptor 1 (TfR1) antibody, wherein the antibody comprises: a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16, and wherein the complexes are formulated with histidine and sucrose.

2. A formulation comprising complexes of the formula: $[R^1]_{n1}$—$R^2$, wherein each $R^1$ independently comprises a group of the formula:

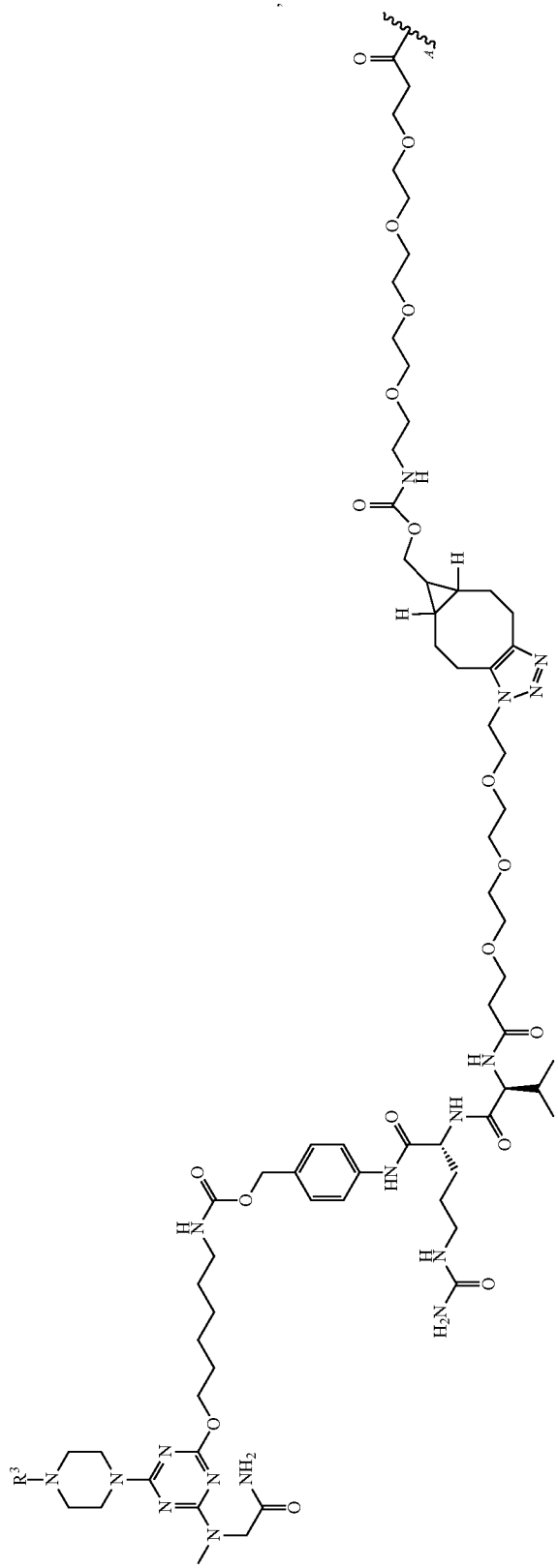

R² comprises an antibody, and

R³ is a phosphorodiamidate morpholino oligomer (PMO);

wherein R¹ is covalently linked to R² at attachment point A; and wherein n1 is an integer of one or greater representing the number of instances of R¹, wherein each instance of R¹ is covalently linked to a different amino acid residue of the antibody, optionally wherein each different amino acid residue is a lysine;

wherein the complexes are formulated with histidine and sucrose, optionally wherein the antibody is an anti-TfR1 antibody, and optionally wherein the average value of n1 of complexes in the formulation is in the range of 1 to 5.

3. The formulation of embodiment 2, wherein the antibody comprises:

a heavy chain complementarity determining region 1 (CDR-H1) comprising a sequence as set forth in SEQ ID NOs: 1, 7, or 12, a heavy chain complementarity determining region 2 (CDR-H2) comprising a sequence as set forth in SEQ ID NOs: 2, 8, or 13, a heavy chain complementarity determining region 3 (CDR-H3) comprising a sequence as set forth in SEQ ID NOs: 3, 9, or 14, a light chain complementarity determining region 1 (CDR-L1) comprising a sequence as set forth in SEQ ID NOs: 4, 10, or 15, a light chain complementarity determining region 2 (CDR-L2) comprising a sequence as set forth in SEQ ID NOs: 5 or 11, and a light chain complementarity determining region 3 (CDR-L3) comprising a sequence as set forth in SEQ ID NOs: 6 or 16.

4. The formulation of any one of embodiments 1 to 3, wherein the formulation is in a lyophilized form.

5. The formulation of any one of embodiments 1 to 3, wherein the formulation is in an aqueous solution.

6. The formulation of embodiment 5, wherein the histidine is present in the aqueous solution at a concentration in the range of 10 mM to 50 mM.

7. The formulation of embodiment 5 or 6, wherein the sucrose is present in the aqueous solution at a concentration in the range of 5% to 15% weight per volume (w/v %).

8. The formulation of any one of embodiments 5 to 7, wherein the aqueous solution has a pH in the range of 5.0 to 7.0.

9. The formulation of any one of embodiments 5-8, wherein the histidine is present in the aqueous solution at a concentration of 25 mM and/or the sucrose is present in the aqueous solution at a concentration of 10 w/v % and/or the aqueous solution is at a pH of 6.0.

10. The formulation of any one of embodiments 1-9, wherein the antibody is a Fab fragment, a full-length IgG, a Fab' fragment, a F(ab')₂ fragment, an scFv, or an Fv.

11. The formulation of embodiment 10, wherein the antibody is a Fab fragment.

12. The formulation of any one of embodiments 1-11, wherein the antibody comprises a heavy chain variable region (VH) comprising an amino acid sequence at least 85% identical to SEQ ID NO: 17; and/or wherein the antibody comprises a light chain variable region (VL) comprising an amino acid sequence at least 85% identical to SEQ ID NO: 18, optionally wherein the antibody comprises a VH comprising the amino acid sequence of SEQ ID NO: 17 and a VL comprising the amino acid sequence of SEQ ID NO: 18.

13. The formulation of any one of embodiments 1-12, wherein the antibody comprises a heavy chain comprising an amino acid sequence at least 85% identical to SEQ ID NO: 19; and/or wherein the antibody comprises a light chain comprising an amino acid sequence at least 85% identical to SEQ ID NO: 20, optionally wherein the antibody comprises a heavy chain comprising the amino acid sequence of SEQ ID NO: 19 and a light chain comprising the amino acid sequence of SEQ ID NO: 20.

14. The formulation of any one of embodiments 1-13, wherein the PMO comprises a nucleotide sequence that is 15-35 nucleotides in length.

15. The formulation of any one of embodiments 1-14, wherein the PMO comprises a nucleotide sequence having a region of complementarity of at least 8 consecutive nucleotides in length to SEQ ID NO: 23, to SEQ ID NO: 24, or to SEQ ID NO: 22.

16. The formulation of any one of embodiments 1-15, wherein the PMO comprises at least 8 consecutive nucleotides of a nucleotide sequence as set forth in SEQ ID NO: 21, optionally wherein the PMO comprises the nucleotide sequence of SEQ ID NO: 21.

17. The formulation of any one of embodiments 2-16, wherein each R¹ comprises formula:

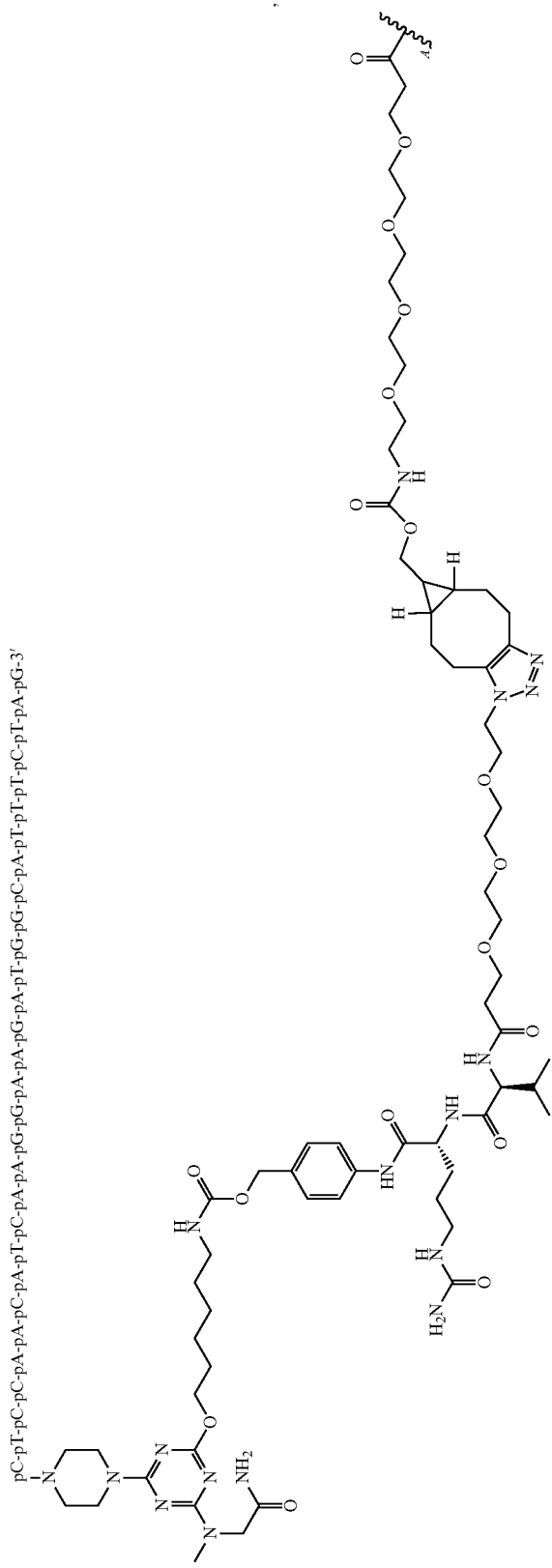

which -pN indicates a base position of a phosphorodiamidate morpholino oligomer (PMO), $R^1$ is covalently linked to $R^2$ at attachment point A; wherein -p reflects a phosphorodiamidate linkage, wherein N corresponds to a nucleobase of adenine (A), cytosine (C), guanine (G), or thymine (T), such that the PMO has a nucleobase sequence of CTCCAA-CATCAAGGAAGATGGCATTTCTAG (SEQ ID NO: 21).

18. The formulation of any one of embodiments 2-16, wherein each $R^1$ comprises formula:

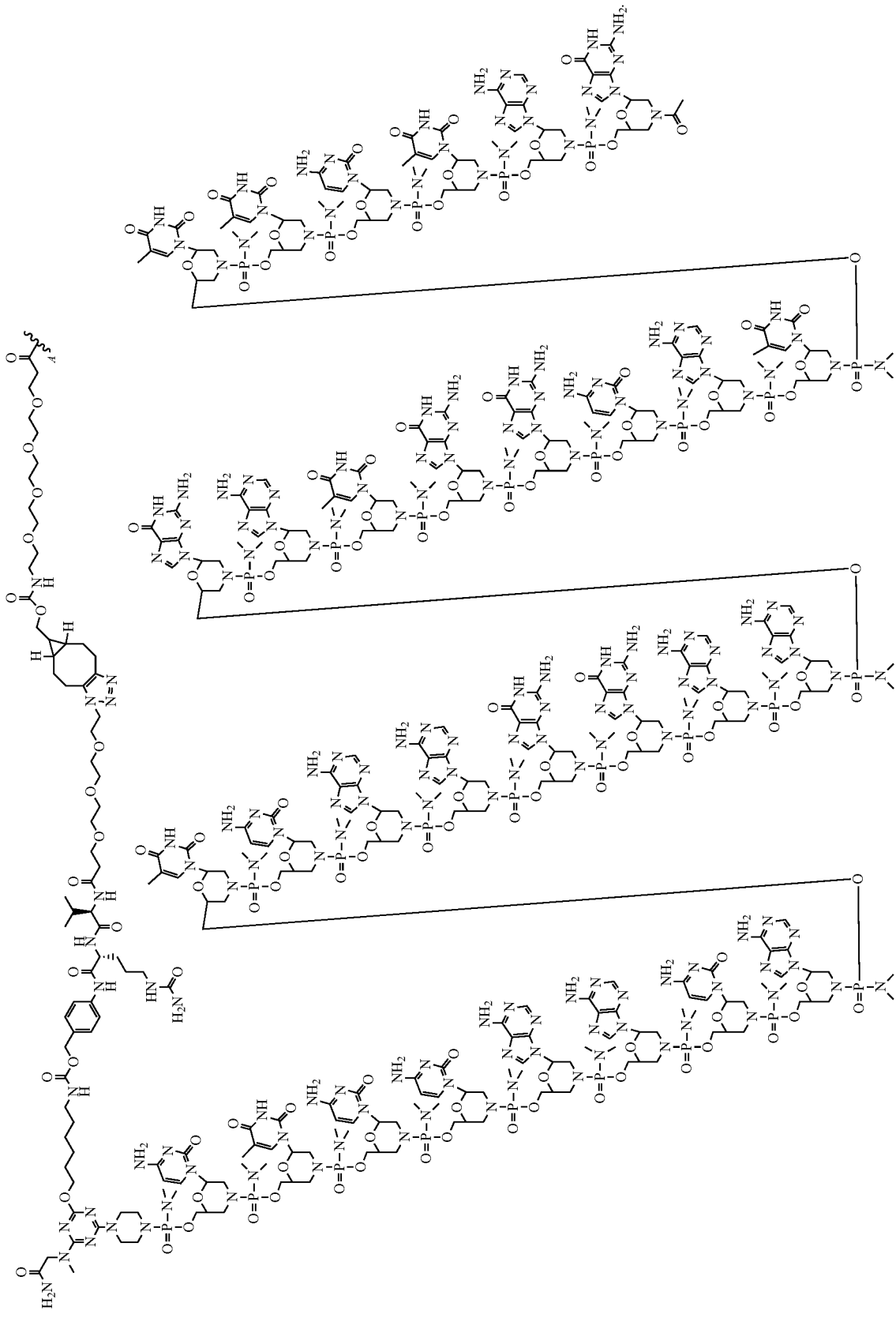

19. The formulation of any one of embodiments 1-18, wherein the complexes are present in the formulation at a concentration in the range of 10 mg/mL to 50 mg/mL.

20. A method of promoting expression or activity of a dystrophin protein in a subject, the method comprising administering to the subject the formulation of any one of embodiments 1-19.

21. The method of embodiment 20, wherein the dystrophin protein is a truncated dystrophin protein.

22. A method of treating a subject having a mutated DMD allele associated with Duchenne Muscular Dystrophy, the method comprising administering to the subject the formulation of any one of embodiments 1-19.

23. The method of embodiment 22, wherein the mutated DMD allele comprises a mutation amenable to exon 51 skipping.

24. The method of embodiment 22 or embodiment 23, wherein the mutated DMD allele comprises a frameshift mutation in exon 51.

25. A complex comprising a structure of the formula $[R^1]_{n1}$—$R^2$, wherein each $R^1$ comprises a group of the formula:

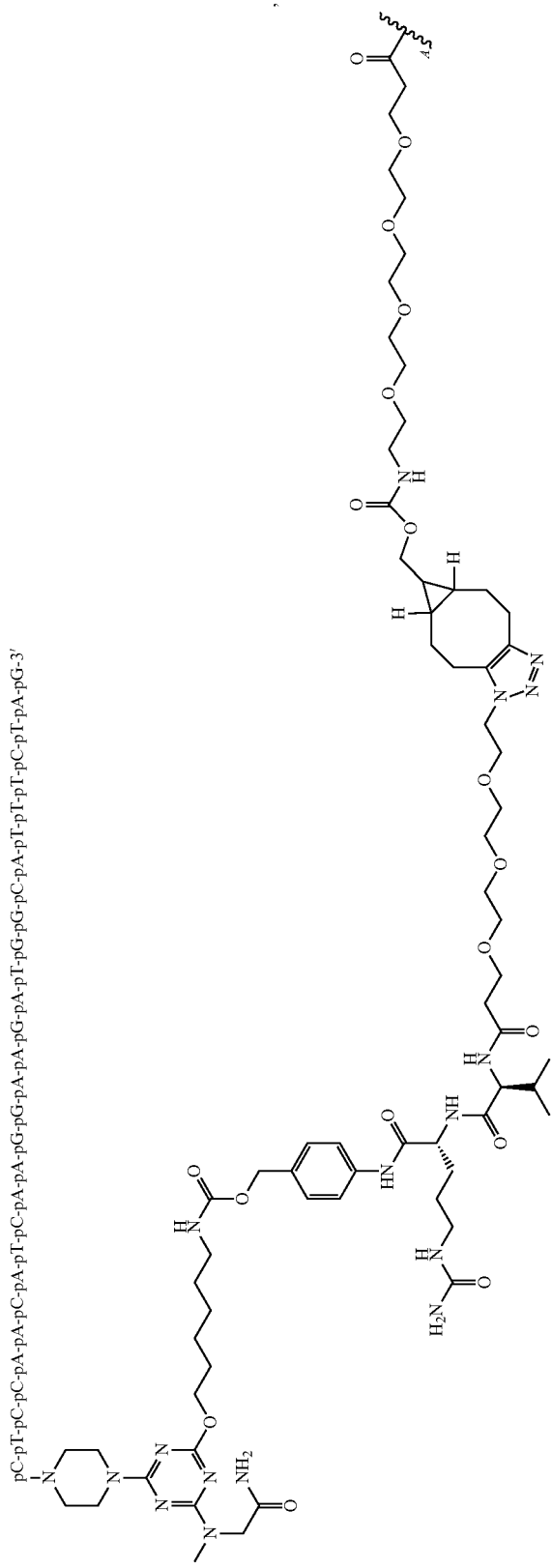

wherein R² comprises a Fab, and wherein the Fab comprises a CDR-H1, a CDR-H2, a CDR-H3, a CDR-L1, a CDR-L2, and a CDR-L3 selected from Table 2, optionally wherein the Fab comprises a VH comprising the amino acid sequence of SEQ ID NO: 17 and a VL comprising the amino acid sequence of SEQ ID NO: 18, further optionally wherein the Fab comprises a heavy chain comprising the amino acid sequence of SEQ ID NO: 19 and a light chain comprising the amino acid sequence of SEQ ID NO: 20, wherein -pN indicates a base position of a phosphorodiamidate morpholino oligomer (PMO), wherein -p reflects a phosphorodiamidate linkage, and wherein N corresponds to a nucleobase of adenine (A), cytosine (C), guanine (G), or thymine (T), such that the oligonucleotide PMO has a nucleobase sequence of CTCCAACATCAAGGAAGATGGCATTCTAG (SEQ ID NO: 21); wherein R¹ is covalently linked to R² at attachment point A; and wherein n1 is an integer of one or greater representing the number of instances of R¹, wherein each instance of R¹ is covalently linked to a different amino acid residue of the Fab, optionally wherein each different amino acid residue is a lysine.

26. A complex comprising a structure of the formula $[R^1]_{n1}$—$R^2$, wherein $R^1$ comprises a group of the formula:

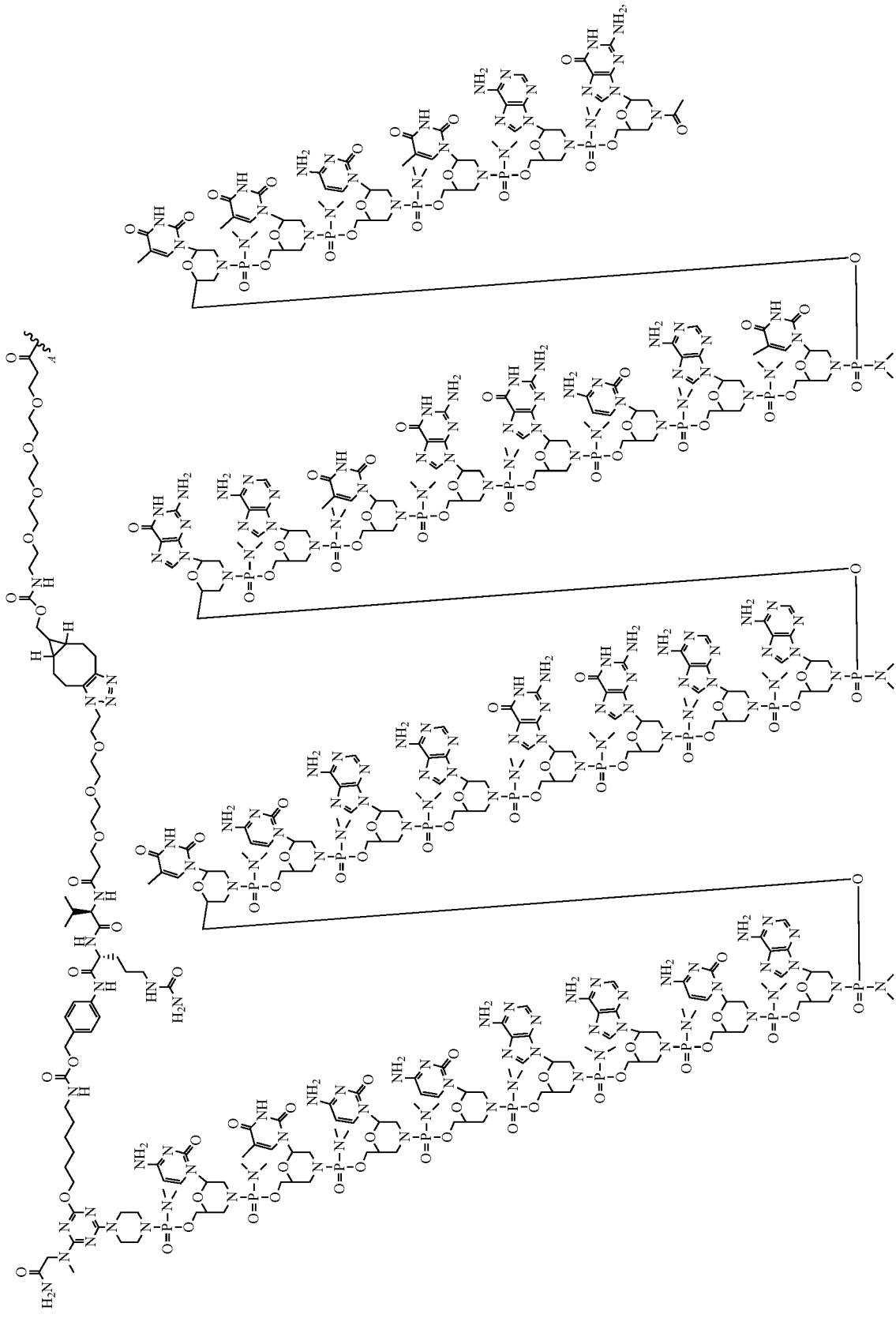

wherein R² comprises a Fab comprising a CDR-H1, a CDR-H2, a CDRH3, a CDR-L1, a CDR-L2, and a CDR-L3 selected from Table 2, optionally wherein R² comprises a Fab comprising a VH comprising the amino acid sequence of SEQ ID NO: 17 and a VL comprising the amino acid sequence of SEQ ID NO: 18, further optionally wherein R² comprises a Fab comprising a heavy chain comprising the amino acid sequence of SEQ ID NO: 19 and a light chain comprising the amino acid sequence of SEQ ID NO: 20; wherein R¹ is covalently linked to at attachment point A; wherein n1 is an integer of one or greater representing the number of instances of R¹, wherein each instance of R¹ is covalently linked to a different amino acid residue of the Fab, optionally wherein each different amino acid residue is a lysine.

27. A formulation comprising a plurality of complexes of embodiment 25 or embodiment 26, and histidine at a concentration of 25 mM, and sucrose at a concentration of 10 w/v %, wherein the formulation is an aqueous solution and is at a pH of 6.0.

28. A lyophilized form of the formulation of embodiment 27.

29. A product produced by a process comprising lyophilizing the formulation of embodiment 27.

30. A frozen form of the formulation of embodiment 27.

31. A product produced by a process comprising freezing the formulation of embodiment 27.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or (e.g., and) one or more modified nucleotides and/or (e.g., and) one or more modified internucleotide linkages and/or (e.g., and) one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A complex comprising a structure of formula (I):
$[R^1]_{n1}$—$R^2$,
wherein each $R^1$ comprises a group of the formula (Ic):

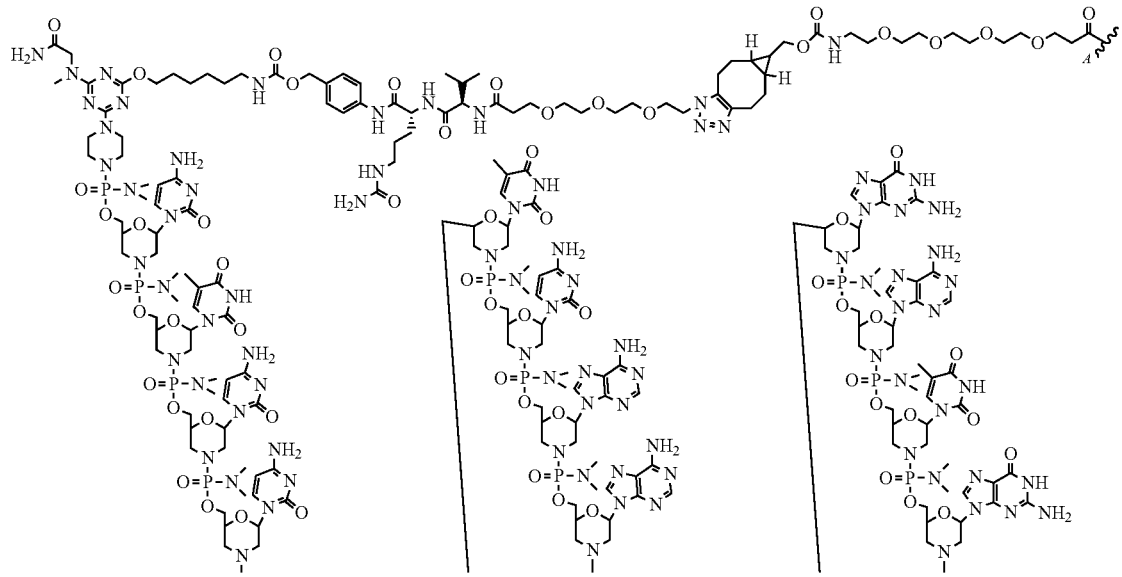

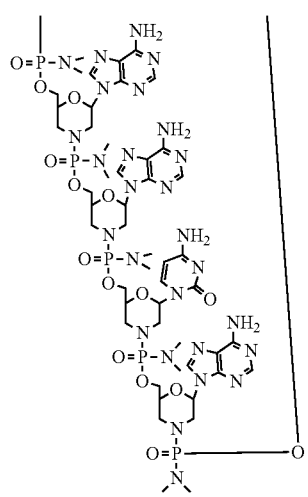
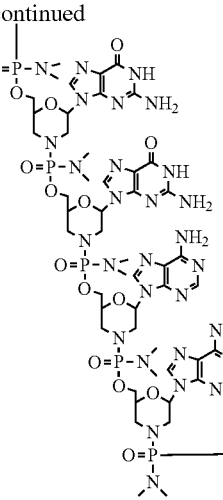
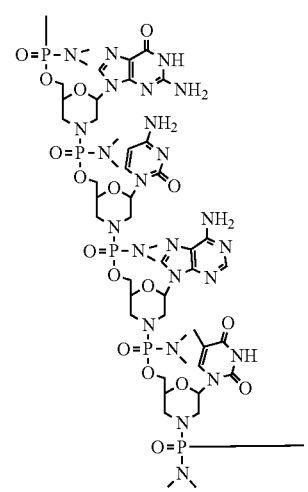
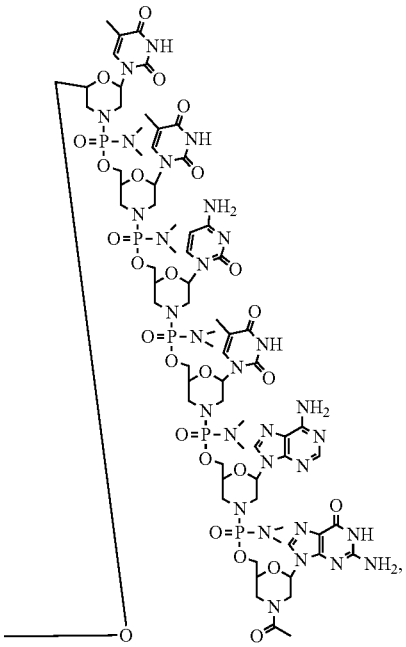

wherein R² comprises a Fab that binds to transferrin receptor 1 (TfR1), wherein the Fab comprises a heavy chain comprising the amino acid sequence of SEQ ID NO: 19 and a light chain comprising the amino acid sequence of SEQ ID NO: 20;

wherein R¹ is covalently linked to R² at attachment point A; wherein n1 is an integer of 1-5 representing the number of instances of R¹, and wherein each instance of R¹ is covalently linked to a different amino acid residue of the Fab.

2. The complex of claim 1, wherein each different amino acid residue is a lysine.

3. The complex of claim 1, wherein the heavy chain of the Fab comprises an N-terminal pyroglutamate.

4. A method of promoting expression or activity of a dystrophin protein in a subject, the method comprising administering to the subject an effective amount of a composition comprising the complex of claim 1.

5. The method of claim 4, wherein the dystrophin protein is a truncated dystrophin protein.

6. A method of treating a subject having a mutated DMD allele associated with Duchenne Muscular Dystrophy, the method comprising administering to the subject an effective amount of a composition comprising the complex of claim 1.

7. The method of claim 6, wherein the mutated DMD allele comprises a mutation amenable to exon 51 skipping.

8. A complex comprising a structure of formula (I):

$[R^1]_{n1}$—$R^2$, wherein each R¹ comprises a group of the formula (Ia):

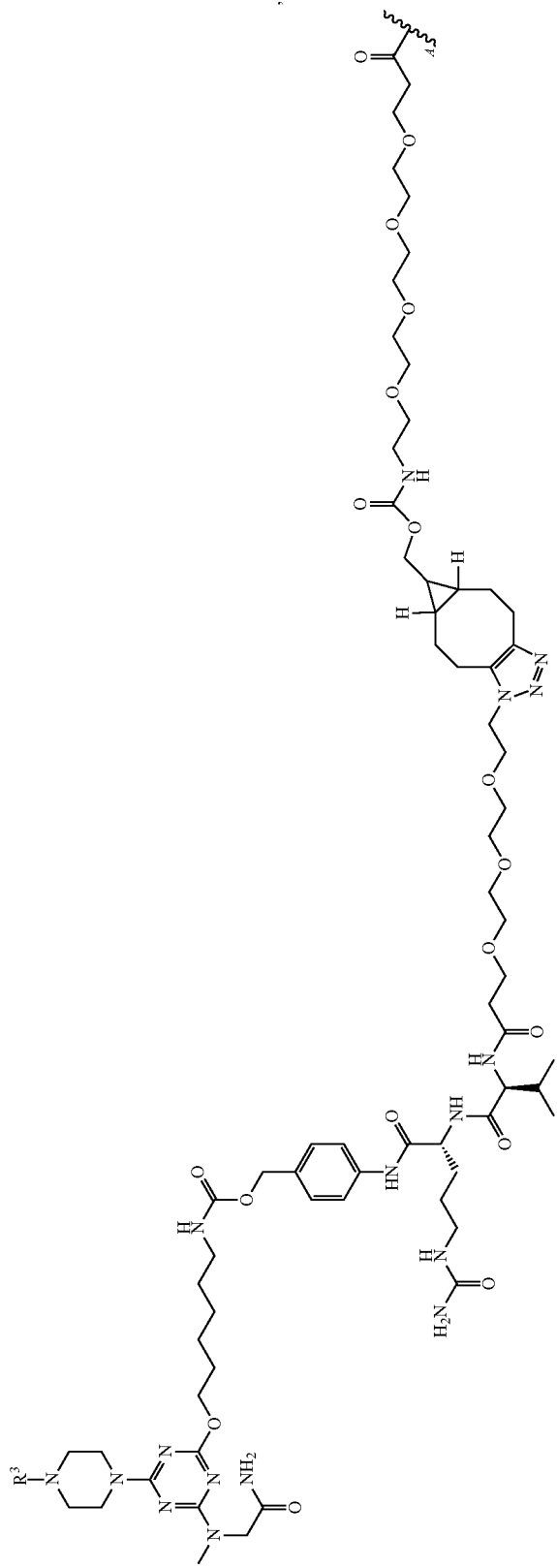

wherein R³ comprises a phosphorodiamidate morpholino oligomer (PMO) comprising the base sequence of CTCCAACATCAAGGAAGATGGCATTTCTAG (SEQ ID NO: 21), wherein the piperazine ring is covalently linked to the 5' end of the PMO of R³;

wherein R² comprises a Fab that binds to transferrin receptor 1 (TfR1), wherein the Fab comprises a heavy chain comprising the amino acid sequence of SEQ ID NO: 19 and a light chain comprising the amino acid sequence of SEQ ID NO: 20;

wherein R¹ is covalently linked to R² at attachment point A; wherein n1 is an integer of 1-5 representing the number of instances of R¹, and wherein each instance of R¹ is covalently linked to a different amino acid residue of the Fab.

9. The complex of claim 8, wherein each different amino acid residue is a lysine.

10. The complex of claim 8, wherein the heavy chain of the Fab comprises an N-terminal pyroglutamate.

11. A method of promoting expression or activity of a dystrophin protein in a subject, the method comprising administering to the subject an effective amount of a composition comprising the complex of claim 8.

12. The method of claim 11, wherein the dystrophin protein is a truncated dystrophin protein.

13. A method of treating a subject having a mutated DMD allele associated with Duchenne Muscular Dystrophy, the method comprising administering to the subject an effective amount of a composition comprising the complex of claim 8.

14. The method of claim 13, wherein the mutated DMD allele comprises a mutation amenable to exon 51 skipping.

15. A complex comprising a structure of formula (I): $[R^1]_{n1}—R^2$, wherein each R¹ comprises a group of the formula (Ib):

(Ib)
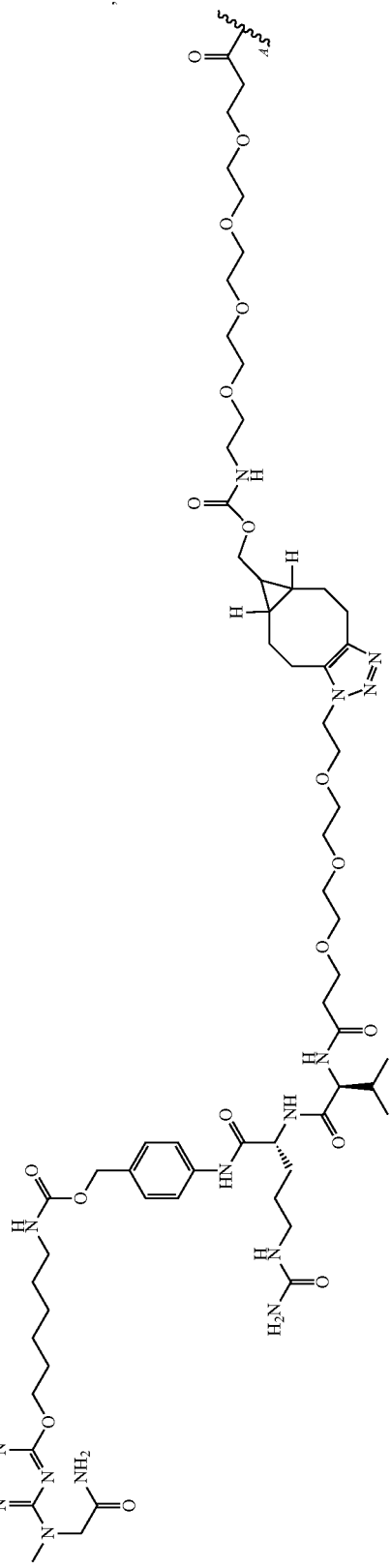

wherein R² comprises a Fab that binds to transferrin receptor 1 (TfR1), wherein the Fab comprises a heavy chain comprising the amino acid sequence of SEQ ID NO: 19 and a light chain comprising the amino acid sequence of SEQ ID NO: 20, wherein -pA, -pC, -pT, and -pG indicate base positions of a phosphorodiamidate morpholino oligomer (PMO), wherein -p reflects a phosphorodiamidate linkage, such that the PMO has a nucleobase sequence of CTCCAACATCAAGGAAGATGGCATTTCTAG (SEQ ID NO: 21), wherein R¹ is covalently linked to R² at attachment point A, wherein n1 is an integer of 1-5 representing the number of instances of R¹, wherein each instance of R¹ is covalently linked to a different amino acid residue of the Fab via a linkage comprising an amide bond formed with each different amino acid residue.

16. The complex of claim 15, wherein each different amino acid residue is a lysine or an arginine.

17. The complex of claim 15, wherein the heavy chain of the Fab comprises an N-terminal pyroglutamate.

18. A method of promoting expression or activity of a dystrophin protein in a subject, the method comprising administering to the subject an effective amount of a composition comprising the complex of claim 15.

19. The method of claim 18, wherein the dystrophin protein is a truncated dystrophin protein.

20. A method of treating a subject having a mutated DMD allele associated with Duchenne Muscular Dystrophy, the method comprising administering to the subject an effective amount of a composition comprising the complex of claim 15.

21. The method of claim 20, wherein the mutated DMD allele comprises a mutation amenable to exon 51 skipping.

22. A composition comprising a complex comprising a structure of formula (Id):

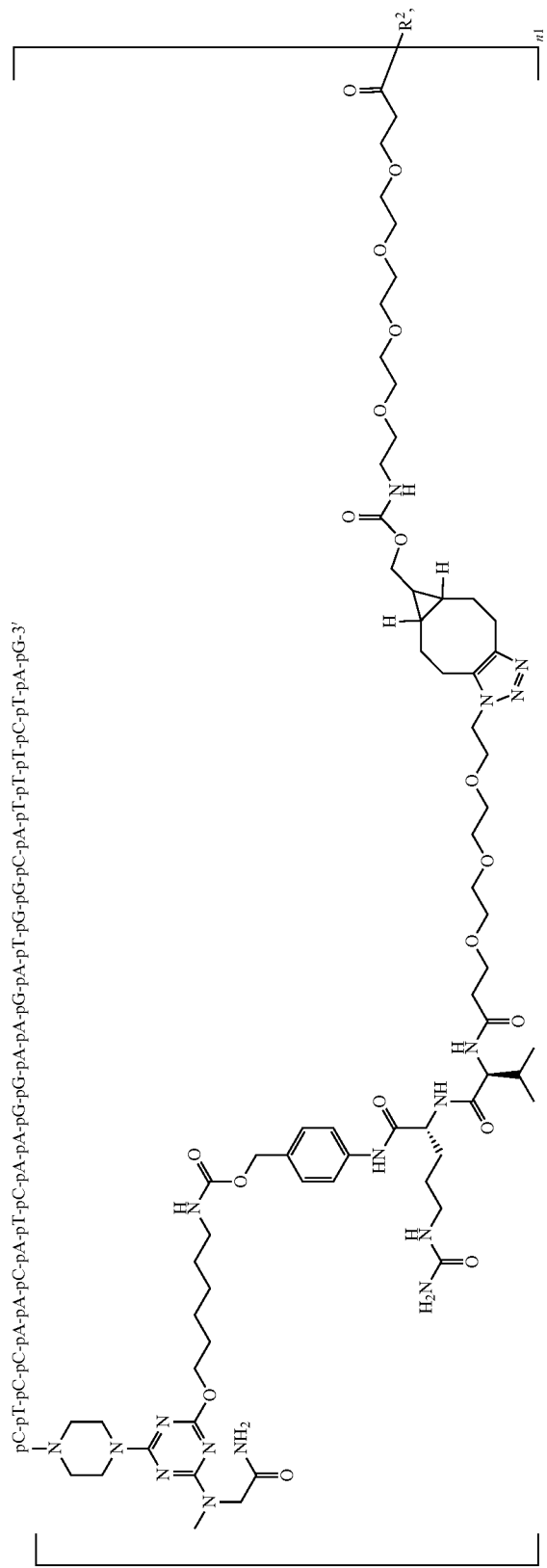

wherein R² comprises a Fab that binds to transferrin receptor 1 (TfR1), wherein the Fab comprises a heavy chain comprising the amino acid sequence of SEQ ID NO: 19 and a light chain comprising the amino acid sequence of SEQ ID NO: 20;

wherein -pA, -pC, -pT, and -pG indicate base positions of a phosphorodiamidate morpholino oligomer (PMO); wherein -p reflects a phosphorodiamidate linkage, such that the PMO comprises a base sequence of CTCCAACATCAAGGAAGATGGCATTTCTAG (SEQ ID NO: 21);

wherein n1 is an integer of 1-5 representing the number of instances of the group enclosed by square brackets, wherein each instance of the group enclosed by square brackets is covalently linked to a different amino acid residue of the Fab, wherein the composition is formulated in a manner suitable for pharmaceutical use.

23. The composition of claim 22, wherein each different amino acid residue is a lysine.

24. The composition of claim 22, wherein the heavy chain of the Fab comprises an N-terminal pyroglutamate.

25. A method of promoting expression or activity of a dystrophin protein in a subject, the method comprising administering to the subject an effective amount of the composition of claim 22.

26. The method of claim 25, wherein the dystrophin protein is a truncated dystrophin protein.

27. A method of treating a subject having a mutated DMD allele associated with Duchenne Muscular Dystrophy, the method comprising administering to the subject an effective amount of the composition of claim 22.

28. The method of claim 27, wherein the mutated DMD allele comprises a mutation amenable to exon 51 skipping.

* * * * *

SEQUENCE LISTING

```
Sequence total quantity: 36
SEQ ID NO: 1           moltype = AA  length = 9
FEATURE                Location/Qualifiers
REGION                 1..9
                       note = Synthetic
source                 1..9
                       mol_type = protein
                       organism = synthetic construct
```

```
SEQUENCE: 1
GYSITSGYY                                                                              9

SEQ ID NO: 2            moltype = AA  length = 7
FEATURE                 Location/Qualifiers
REGION                  1..7
                        note = Synthetic
source                  1..7
                        mol_type = protein
                        organism = synthetic construct
SEQUENCE: 2
ITFDGAN                                                                                7

SEQ ID NO: 3            moltype = AA  length = 12
FEATURE                 Location/Qualifiers
REGION                  1..12
                        note = Synthetic
source                  1..12
                        mol_type = protein
                        organism = synthetic construct
SEQUENCE: 3
TRSSYDYDVL DY                                                                         12

SEQ ID NO: 4            moltype = AA  length = 6
FEATURE                 Location/Qualifiers
REGION                  1..6
                        note = Synthetic
source                  1..6
                        mol_type = protein
                        organism = synthetic construct
SEQUENCE: 4
QDISNF                                                                                 6

SEQ ID NO: 5            moltype =     length =
SEQUENCE: 5
000

SEQ ID NO: 6            moltype = AA  length = 9
FEATURE                 Location/Qualifiers
REGION                  1..9
                        note = Synthetic
source                  1..9
                        mol_type = protein
                        organism = synthetic construct
SEQUENCE: 6
QQGHTLPYT                                                                              9

SEQ ID NO: 7            moltype = AA  length = 6
FEATURE                 Location/Qualifiers
REGION                  1..6
                        note = Synthetic
source                  1..6
                        mol_type = protein
                        organism = synthetic construct
SEQUENCE: 7
SGYYWN                                                                                 6

SEQ ID NO: 8            moltype = AA  length = 16
FEATURE                 Location/Qualifiers
REGION                  1..16
                        note = Synthetic
source                  1..16
                        mol_type = protein
                        organism = synthetic construct
SEQUENCE: 8
YITFDGANNY NPSLKN                                                                     16

SEQ ID NO: 9            moltype = AA  length = 10
FEATURE                 Location/Qualifiers
REGION                  1..10
                        note = Synthetic
source                  1..10
                        mol_type = protein
                        organism = synthetic construct
SEQUENCE: 9
SSYDYDVLDY                                                                            10

SEQ ID NO: 10           moltype = AA  length = 11
FEATURE                 Location/Qualifiers
```

```
REGION                  1..11
                        note = Synthetic
source                  1..11
                        mol_type = protein
                        organism = synthetic construct
SEQUENCE: 10
RASQDISNFL N                                                              11

SEQ ID NO: 11           moltype = AA   length = 7
FEATURE                 Location/Qualifiers
REGION                  1..7
                        note = Synthetic
source                  1..7
                        mol_type = protein
                        organism = synthetic construct
SEQUENCE: 11
YTSRLHS                                                                    7

SEQ ID NO: 12           moltype = AA   length = 8
FEATURE                 Location/Qualifiers
REGION                  1..8
                        note = Synthetic
source                  1..8
                        mol_type = protein
                        organism = synthetic construct
SEQUENCE: 12
GYSITSGY                                                                   8

SEQ ID NO: 13           moltype =    length =
SEQUENCE: 13
000

SEQ ID NO: 14           moltype = AA   length = 8
FEATURE                 Location/Qualifiers
REGION                  1..8
                        note = Synthetic
source                  1..8
                        mol_type = protein
                        organism = synthetic construct
SEQUENCE: 14
SYDYDVLD                                                                   8

SEQ ID NO: 15           moltype = AA   length = 7
FEATURE                 Location/Qualifiers
REGION                  1..7
                        note = Synthetic
source                  1..7
                        mol_type = protein
                        organism = synthetic construct
SEQUENCE: 15
SQDISNF                                                                    7

SEQ ID NO: 16           moltype = AA   length = 6
FEATURE                 Location/Qualifiers
REGION                  1..6
                        note = Synthetic
source                  1..6
                        mol_type = protein
                        organism = synthetic construct
SEQUENCE: 16
GHTLPY                                                                     6

SEQ ID NO: 17           moltype = AA   length = 119
FEATURE                 Location/Qualifiers
REGION                  1..119
                        note = Synthetic
source                  1..119
                        mol_type = protein
                        organism = synthetic construct
SEQUENCE: 17
QVQLQESGPG LVKPSQTLSL TCTVTGYSIT SGYYWNWIRQ PPGKGLEWIG YITFDGANNY          60
NPSLKNRVSI SRDTSKNQFS LKLSSVTAED TATYYCTRSS YDYDVLDYWG QGTTVTVSS          119

SEQ ID NO: 18           moltype = AA   length = 107
FEATURE                 Location/Qualifiers
REGION                  1..107
                        note = Synthetic
source                  1..107
                        mol_type = protein
```

```
                              organism = synthetic construct
SEQUENCE: 18
DIQMTQSPSS LSASVGDRVT ITCRASQDIS NFLNWYQQKP GQPVKLLIYY TSRLHSGVPS    60
RFSGSGSGTD FTLTISSLQP EDFATYYCQQ GHTLPYTFGQ GTKLEIK                 107

SEQ ID NO: 19             moltype = AA  length = 227
FEATURE                   Location/Qualifiers
REGION                    1..227
                          note = Synthetic
source                    1..227
                          mol_type = protein
                          organism = synthetic construct
SEQUENCE: 19
QVQLQESGPG LVKPSQTLSL TCTVTGYSIT SGYYWNWIRQ PPGKGLEWIG YITFDGANNY    60
NPSLKNRVSI SRDTSKNQFS LKLSSVTAED TATYYCTRSS YDYDVLDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHT                227

SEQ ID NO: 20             moltype = AA  length = 214
FEATURE                   Location/Qualifiers
REGION                    1..214
                          note = Synthetic
source                    1..214
                          mol_type = protein
                          organism = synthetic construct
SEQUENCE: 20
DIQMTQSPSS LSASVGDRVT ITCRASQDIS NFLNWYQQKP GQPVKLLIYY TSRLHSGVPS    60
RFSGSGSGTD FTLTISSLQP EDFATYYCQQ GHTLPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 21             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 21
ctccaacatc aaggaagatg gcatttctag                                    30

SEQ ID NO: 22             moltype = DNA  length = 30
FEATURE                   Location/Qualifiers
misc_feature              1..30
                          note = Synthetic
source                    1..30
                          mol_type = other DNA
                          organism = synthetic construct
SEQUENCE: 22
ctagaaatgc catcttcctt gatgttggag                                    30

SEQ ID NO: 23             moltype = DNA  length = 13993
FEATURE                   Location/Qualifiers
source                    1..13993
                          mol_type = genomic DNA
                          organism = Homo sapiens
SEQUENCE: 23
tcctggcatc agttactgtg ttgactcact cagtgttggg atcactcact ttcccctac    60
aggactcaga tctgggaggc aattaccttc ggagaaaaac gaataggaaa aactgaagtg   120
ttacttttt taaagctgct gaagtttgtt ggtttctcat tgtttttaag cctactggag   180
caataaagtt tgaagaactt ttaccaggtt tttttatcg ctgccttgat atacactttt   240
caaaatgctt tggtgggaag aagtagagga ctgttatgaa agagaagatg ttcaaaagaa   300
acattcaca aaatgggtaa atgcacaatt ttctaagttt gggaagcagc atattgagaa   360
cctcttcagt gacctacagg atgggaggcg cctcctagac ctccttgaag gcctgacagg   420
gcaaaaactg ccaaaagaaa aaggatccac aagagttcat gccctgaaca atgtcaacaa   480
ggcactgcgg gttttgcaga acaataatgt tgatttagtg aatattggaa gtactgacat   540
cgtagatgaa aatcataaac tgactcttgg ttttgatttgg aatataatcc tccactggca   600
ggtcaaaaat gtaatgaaaa atatcatggc tggattgcaa caaaccaaca gtgaaaagat   660
tctcctgagc tgggtccgac aatcaactcg taattatcca caggttaatg taatcaactt   720
caccaccagc tggtctgatg gcctggcttt gaatgtctc atccatagtc ataggccaga   780
cctatttgac tggaatagtg tggtttgcca gcagtcagcc acacaacgac tggaacatgc   840
attcaacatc gccagatatc aattaggcat agagaaacta ctcgatcctg aagatgttga   900
taccacctat ccagataaga agtccatctt aatgtacatc acatcactct ccaagttttt   960
gcctcaacaa gtgagcattg aagccatcca ggaagtggaa atgttgccaa ggccacctaa  1020
agtgactaaa gaagaacatt tcagttacca tcatcaaatg cactattctc aacagatcac  1080
ggtcagtcta gcacagggat atgagagaac ttcttcccct aagcctcgat tcaagagcta  1140
tgcctacaca caggctgctt atgtcaccac ctctgaccct acacggagcc catttccttc  1200
acagcatttg gaagctcctg aagacaagtc atttggcagt tcattgatgg agagtgaagt  1260
aaaacctgga cgttatcaaa cagctttaga agaagtatta tcgtggctgc tttctgctga  1320
```

```
ggacacattg caagcacaag gagagatttc taatgatgtg gaagtggtga aagaccagtt   1380
tcatactcat gaggggtaca tgatggattt gacagcccat cagggccggg ttggtaatat   1440
tctacaattg ggaagtaagc tgattggaac aggaaaatta tcagaagatg aagaaactga   1500
agtacaagag cagatgaatc tcctaaattc aagatgggaa tgcctcaggg tagctagcat   1560
ggaaaaacaa agcaatttac atagagtttt aatggatctc cagaatcaga aactgaaaga   1620
gttgaatgac tggctaacaa aaacagaaga aagaacaagg aaaatggagg aagagcctct   1680
tggacctgat cttgaagacc taaaacgcca agtacaacaa cataaggtgc ttcaagaaga   1740
tctagaacaa gaacaagtca gggtcaattc tctcactcac atggtggtgg tagttgatga   1800
atctagtgga gatcacgcaa ctgctgcttt ggaagaacaa cttaaggtat tgggagatcg   1860
atgggcaaac atctgtagat ggacagaaga ccgctgggtt cttttacaag acatccttct   1920
caaatggcaa cgtcttactg aagaacagtg ccttttagt gcatggcttt cagaaaaaga   1980
agatgcagtg aacaagattc acacaactgg ctttaaagat caaatgaaa tgttatcaag   2040
tcttcaaaaa ctggccgttt taaaagcgga tctagaaaaa aaaagcaat ccatgggcaa   2100
actgtattca ctcaaacaag atcttctttc aactactgaa aataagtcag tgacccagaa   2160
gacggaagca tggctggata actttgcccg gtgttgggat aatttagtcc aaaaacttga   2220
aaagagtaca gcacaggattt cacaggctgt caccaccact cagccatcac taacacagac   2280
aactgtaatg gaaacagtaa ctacggtgac acacaaggaa cagatcctgg taaagcatgc   2340
tcaagaggaa cttccaccac caccccccca aaagaagagg cagattactg tggattctga   2400
aattaggaaa aggttggatg ttgatataac tgaacttcac agctggatta ctcgctcaga   2460
agctgtgttg cagagtcctg aatttgcaat cttcggaag gaaggcaact tctcagactt   2520
aaaagaaaaa gtcaatgcca tagagcgaga aaagctgag aagttcagaa aactgcaaga   2580
tgccagcaga tcagctcagg ccctggtgga acagtggtg aatgagggtg ttaatgcaga   2640
tagcatcaaa caagcctcag aacaactgaa cagccggtgg atcgaattct gccagttgct   2700
aagtgagaga cttaactggc tgagtatca gaacaacatc atcgctttct ataatcagct   2760
acaacaattg gagcagatga caactactgc tgaaaactgg ttgaaaatcc aacccaccac   2820
cccatgcgag ccaacagcaa ttaaaagtca gttaaaaatt tgtaaggatg aagtcaaccg   2880
gctatcaggt cttcaacctc aaattgaacg attaaaaatt caaagcatag ccctgaaaga   2940
gaaaggacaa ggacccatgt tcctggatgc agactttgtg gcctttacaa atcattttaa   3000
gcaagtcttt tctgatgtgc aggccagaga gaaagagcta cagacaattt ttgacacttt   3060
gccaccaatg cgctatcagg agaccatgag tgccatcagg acatgggtcc agcagtcaga   3120
aaccaaactc tccatacctc aacttagtgt caccgactat gaaatcatgg agcagagact   3180
cggggaattg caggctttac aaagttctct gcaagagcaa caaagtggcc tatactatct   3240
cagcaccact gtgaaagaga tgtcgaagaa agcgccctct gaaattagcc ggaaatatca   3300
atcagaattt gaagaaattg agggacgctg gaagaagctc tcctcccagc tggttgacaa   3360
ttgtcaaaag ctagaggagc aaatgaataa actcccgaaaa attcagaatc acatacaaac   3420
cctgaagaaa tggatggctg aagttgatgt ttttctgaag gaggaatggc ctgcccttgg   3480
ggattcagaa attctaaaaa agcagctgaa acagtcaga cttttagtca gtgatattca   3540
gacaattcag cccagtctaa acagtgtcaa tgaaggtggg cagaagataa agaatgaagc   3600
agagccagag tttgcttcga gacttgagac agaactcaaa gaacttaaca ctcagtggga   3660
tcacatgtgc caacaggtct atgccagaaa ggaggccttg aagggaggtt tggagaaaac   3720
tgtaagcctc cagaaagatc tatcagagat gcacgaatgg atgacacaag ctgaagaaga   3780
gtatcttgag agagattttg aatataaaac tccagatgaa ttacagaaag cagttgaaga   3840
gatgaagaga gctaaagaag aggcccaaca aaaagaggag aaagtgaaac tccttactga   3900
gtctgtaaat agtgtcatag ctcaagctcc acctgtagca caagaggcct taaaaaagga   3960
acttgaaact ctaaccacca actaccagtg gctctgcact aggctgaatg ggaaatgcaa   4020
gactttggaa gaagtttggg catgttgcca tgagttattg tcatacttgg agaaagcaaa   4080
caagtggcta attgaagtag aatttaaact taaaccact gaaaacattc ctggcggagc   4140
tgaggaaatc tctgaggtgc tagattcact tgaaaatttg atgcgacatt cagaggataa   4200
cccaaatcag attcgcatat ggcacagacc cctaacagat ggcggagtca tggatgagct   4260
aatcaatgag gaacttgaga catttaattc tcgttgagg gaactacatg aagaggctgt   4320
aaggaagcaa aagttgcttg aacagagcat ccagtctgcc caggagactg aaaaatcctt   4380
acacttaatc caggagtccc tcacattcat tgacaagcag ttggcagctt atattgcaga   4440
caaggtggac gcagctcaaa tgcctcagga agcccagaaa atccaatctg atttgacaag   4500
tcatgagatc agtttagaag aaatgaagaa acataatcag gggaaggagg ctgcccaaag   4560
agtcctgtct cagattgatg ttgcacagaa aaaattacaa gatgtctcca tgaagtttcg   4620
attattccag aaaccagcca attttgagca gcgtctacaa gaaagtaaga tgattttaga   4680
tgaagtgaag atgcacttgc ctgcattgga aacaaagagt gtggaacagg aagtagtaca   4740
gtcacagcta aatcattgtg tgaacttgta taaaagtctg agtgaagtga agtctgaagt   4800
ggaaattggtg ataaagactg gacgtcagat tgtacagaaa agcagacgg aaaatcccga   4860
agaacttgat gaaagagtaa cagcttgaa attgcattat aatgagctgg gagcaaaggt   4920
aacagaaaga aagcaacagt tggagaaatg cttgaaattg tcccgtaaga tgcgaaagga   4980
aatgaatgtc ttgacagaat ggctggcagc tacagatatg gaattgacaa agagatcagc   5040
agttgaagga atgcctagta atttggattc tgaagttgcc tggggaaagg ctactcaaaa   5100
agagattgag aaacagaagg tgcacctgaa gagtatcaca gaggtaggag aggccttgaa   5160
aacagttttg ggcaagaagg agacgttggt ggaagataaa ctcagtcttc tgaatagtaa   5220
ctggatagct gtcacctccc gagcagaaga gtggttaaat cttttgttgg aataccagaa   5280
acacatggaa acttttgacc agaatgtgga ccacatcaca aagtggatca ttcaggctga   5340
cacttttg gatgaatcag agaaaaagaa accccagcaa aaagaagacg tgcttaagcg   5400
tttaaaggga gaactgaatg acatacgccc aaaggtgaac tctcacgtg accaagcagc   5460
aaacttgatg gcaaaccgcg gtgaccactg caggaaatta gtagagcccc aaatctcaga   5520
gctcaaccat cgatttgcag ccatttcaca cagaattaag actggaaagg cctccattcc   5580
tttgaaggaa ttggagcagt ttaactcaga tatacaaaaa ttgcttgaac cactggaggc   5640
tgaaattcag caggggtga atctgaaaga ggaagcttc aataaagata tgaatgaaga   5700
aggttacaaag actgtaaaag aattgttgca aagagaagca aacttacaac aaagaatcac   5760
agatgagaga aagcgagagg aaataaagat aaaacagcag ctgttacaga caaaacataa   5820
tgctctcaag gatttgaggt ctcaagaag aaaaaaggct ctagaaattt ctcatcagtg   5880
gtatcagtac aagaggcagg ctgatgatct cctgaaatgc ttggatgaca ttgaaaaaaa   5940
attagccagc ctacctgagc ccagagatga aggaaaata aaggaaattg atcgggaatt   6000
gcagaagaag aaagaggagc tgaatgcagt gcgtaggcaa gctgagggct tgtctgagga   6060
```

```
tggggccgca atggcagtgg agccaactca gatccagctc agcaagcgct ggcgggaaat    6120
tgagagcaaa tttgctcagt ttcgaagact caactttgca caaattcaca ctgtccgtga    6180
agaaacgatg atggtgatga ctgaagacat gcctttggaa atttcttatg tgccttctac    6240
ttatttgact gaaatcactc atgtctcaca agccctatta gaagtggaac aacttctcaa    6300
tgctcctgac ctctgtgcta aggactttga agatctcttt aagcaagagg agtctctgaa    6360
gaatataaaa gatagtctac aacaaagctc aggtcggatt gacattattc atagcaagaa    6420
gacagcagca ttgcaaagtg caacgcctgt ggaaagggtg aagctacagg aagctctctc    6480
ccagcttgat ttccaatggg aaaaagttaa caaaatgtac aaggaccgac aagggcgatt    6540
tgacagatct gttgagaaat ggcggcgttt tcattatgat ataaagatat ttaatcagtg    6600
gctaacagaa gctgaacagt ttctcagaaa gacacaaatt cctgagaatt gggaacatgc    6660
taaatacaaa tggtatctta aggaactcca ggatggcatt gggcagcggc aaactgttgt    6720
cagaacattg aatgcaactg gggaagaaat aattcagcaa tcctcaaaaa cagatgccag    6780
tattctacag gaaaaattgg gaagcctgaa tctgcggtgg caggaggtct gcaaacagct    6840
gtcagacaga aaaagaggc tagaagaaca aaagaatatc ttgtcagaat ttcaaagaga    6900
tttaaatgaa tttgttttat ggttggagga agcagataac attgctagta tcccacttga    6960
acctggaaaa gagcagcaac taaagaaaa gcttgagcaa gtcaagttac tggtggaaga    7020
gttgcccctg cgccagggaa ttctcaaaca attaaatgaa actggaggac ccgtgcttgt    7080
aagtgctccc ataagcccag aagagcaaga taaacttgaa aataagctca agcagacaaa    7140
tctccagtgg ataaaggttt ccagagcttt acctgagaaa caaggagaaa ttgaagctca    7200
aataaaagac cttgggcagc ttgaaaaaaa gcttgaagac cttgaagagc agttaaatca    7260
tctgctgctg tggttatctc ctattaggaa tcagttggaa atttataacc aaccaaacca    7320
agaaggacca tttgacgttc aggaaactga aatagcagtt caagctaaac aaccggatgt    7380
ggaagagatt ttgtctaaag ggcagcattt gtacaaggaa aaaccagcca ctcagccagt    7440
gaagaggaag ttagaagatc tgagctctga gtggaaggcg gtaaaccgtt tacttcaaga    7500
gctgagggca aagcagcctg acctagctcc tggactgacc actattggag cctctcctac    7560
tcagactgtt actctggtga cacaacctgt ggttactaag gaaactgcca tctccaaact    7620
agaaatgcca tcttccttga tgttggaggt acctgctctg gcagatttca accgggcttg    7680
gacagaactt accgactggc tttctctgct tgatcaagtt ataaaatcac agagggtgat    7740
ggtgggtgac cttgaggata tcaacgagat gatcatcaag cagaaggcaa caatgcagga    7800
tttggaacag aggcgtcccc agttggaaga actcattacc gctgcccaaa atttgaaaaa    7860
caagaccagc aatcaagagg ctagaacaat cattacggat cgaattgaaa gaattcagaa    7920
tcagtgggat gaagtacaag aacaccttca gaaccggagg caacagttga atgaaatgtt    7980
aaaggattca acacaatggc tggaagctaa ggaagaagct gagcaggtct taggacaggc    8040
cagagccaag cttgagtcat ggaaggaggg tccctataca gtaatgatca tccaaaagaa    8100
aatcacagaa accaagcagt cctccgccag tggcagacaa atgtagatgt    8160
ggcaaatgac ttggccctga aacttctccg ggattattct gcagatgata ccagaaaagt    8220
ccacatgata acagagaata tcaatgcctc ttggagaagc attcataaaa gggtgagtga    8280
gcgagaggct gctttggaag aaactcatag attactgcaa cagttccccc tggacctgga    8340
aaagtttctt gcctggctta cagaagctga aacaactgca atgtcctac aggatgctac    8400
ccgtaaggaa aggctcctag aagactccaa gggagtaaaa gagctgatga acaatggca    8460
agacctccaa ggtgaaattg aagctcacac agatgtttat cacaacctgg atgaaaacag    8520
ccaaaaaatc ctgagatccc tggaaggttc cgatgatgca gtcctgttac aaagacgttt    8580
ggataacatg aacttcaagt ggagtgaact tcggaaaaag tctctcaaca ttaggtccca    8640
tttgaagcc agttctgacc agtgaagcg tctgcacctt tctctgcagg aacttctggt    8700
gtggctacag ctgaaagatg atgaattaag ccggcaggca cctattggag cgacttcc    8760
agcagttcag aagcagaacg atgtacatag ggccttcaag agggaattga aaactaaaga    8820
acctgtaatc atgagtactc ttgagactgt acgaatattt ctgacagagc agcctttgga    8880
aggactagag aaactctacc aggagcccag agagctgcct cctgaggaga gcccagaa     8940
tgtcactcgg cttctacgaa gcaggctga ggaggtcaat actgagtggg aaaaattgaa    9000
cctgcactcc gctgactggc agagaaaat agatgagacc cttgaaagac tccaggaact    9060
tcaagaggcc acggatgagc tggacctcaa gctgcgcaa gctgaggtga tcaagggatc    9120
ctggcagccc gtgggcgatc tcctcattga ctctctccaa gatcacctcg agaaagtcaa    9180
ggcacttcga ggagaaattg cgcctctgaa agagaacgtg agccacgtca atgaccttgc    9240
tcgccagctt accactttgg gcattcagct ctcaccgtat aacctcagca ctctggaaga    9300
cctgaacacc agatggaagc ttctgcaggt ggccgtcgag gaccgagtca ggcagctgca    9360
tgaagcccac agggactttg gtccagcatc tcagcacttt ctttccacgt ctgtccaggg    9420
tccctgggag agagccatct cgccaaacaa agtgccctac tatatcaacc acgagactca    9480
aacaacttgc tgggaccatc ccaaaatgac agagctctac cagtctttag ctgacctgaa    9540
taatgtcaga ttctcagctt ataggactgc catgaaactc cgaagactgc agaaggccct    9600
ttgcttggat ctcttgagcc tgtcagctgc atgtgatgcc ttggaccagc acaacctcaa    9660
gcaaaatgac cagcccatgg atatcctgca gattattaat tgtttgacca ctatttatga    9720
ccgcctggag caagagcaca acaatttggt caacgtccct ctctgcgtgg atatgtgtct    9780
gaactggctg ctgaatgttt atgatacggg acgaacaggg aggatccgtg tcctgtcttt    9840
taaaactggc atcatttccc tgtgtaaagc acatttggaa gcaagtaca gatacctttt    9900
caagcaagtg gcaagttcaa caggattttg tgaccagcgc aggctgggcc tcttctgca    9960
tgattctatc caaattccaa gacagttggg tgaagttgca tccttgggg gcagtaacat   10020
tgagccaagt gtccggagct gcttccaatt tgctaataat aagccagaga tcgaagcggc   10080
cctcttccta gactggtgatga gactggaacc ccagtccatg gtgtggctgc ccgtcctgca   10140
cagagtggct gctgcagaaa ctgccaagca tcaggccaaa tgtaacatct gcaaagagtg   10200
tccaatcatt ggattcaggt acaggagtct aaagcacttt aattatgaca tctgccaaag   10260
ctgcttttt tctggtcgag ttgcaaaagg ccataaaatg cactatccca tggtggaata   10320
ttgcactccg actacatcag agaagatgt tcgagacttt gccaaggtac taaaaaacaa   10380
atttcgaacc aaaaggtatt ttgcgaagca tccccgaatg ggctacctgc cagtgcagac   10440
tgttagg ggggacaaca tggaaactcc cgttactctg atcaacttct ggcagtaga    10500
ttctgcgcct gcctcgtccc ctcagctttc acacgatgat actcattcac gcattgaaca   10560
ttatgctagc aggctagcag aaatggaaaa cagcaatgga tcttatctaa atgatagcat   10620
ctctcctaat gagagcatag atgatgaaca tttgttaatc cagcattact gccaaagttt   10680
gaaccaggac tcccccctga gccagcctcg tagtcctgcc cagatcttga tttccttaga   10740
gagtgaggaa agagggggagc tagagagaat cctagcagat cttgaggaag aaacaggaa   10800
```

```
tctgcaagca gaatatgacc gtctaaagca gcagcacgaa cataaaggcc tgtcccccact    10860
gccgtcccct cctgaaatga tgcccacctc tccccagagt ccccgggatg ctgagctcat    10920
tgctgaggcc aagctactgc gtcaacacaa aggccgcctg gaagccagga tgcaaatcct    10980
ggaagaccaa aataaacagc tggagtcaca gttacacagg ctaaggcagc tgctggagca    11040
accccaggca gaggccaaag tgaatggcac aacggtgtcc tctccttcta cctctctaca    11100
gaggtccgac agcagtcagc ctatgctgct ccgagtggtt ggcagtcaaa cttcggactc    11160
catgggtgag gaagatcttc tcagtcctcc ccaggacaca agcacagggt tagaggaggt    11220
gatggagcaa ctcaacaact ccttccctag ttcaagagga gaaatacccc ctggaaagcc    11280
aatgagagag gacacaatgt aggaagtctt ttccacatgg cagatgattt gggcagagca    11340
atggagtcct tagtatcagt catgacagat gaagaaggag cagaataaat gttttacaac    11400
tcctgattcc cgcatggttt ttataatatt catacaacaa agaggattag acagtaagag    11460
tttacaagaa ataaatctat attttttgtga agggtagtgg tattatactg tagatttcag    11520
tagtttctaa gtctgttatt gttttgttaa caatggcagg ttttacacgt ctatgcaatt    11580
gtacaaaaaa gttataagaa aactacatgt aaaatcttga tagctaaata acttgccatt    11640
tctttatatg gaacgcattt tgggttgttt aaaaatttat aacagttata agaaagatt     11700
gtaaactaaa gtgtgctttta taaaaaaaag ttgtttataa aaaccccctaa aaacaaaaca   11760
aacacacaca cacacacata cacacacaca cacaaaactt tgaggcagcg cattgttttg   11820
catccttttg gcgtgatatc catatgaaat tcatgcttt ttcttttttt gcatattaaa   11880
gataagactt cctctaccac cacaccaaat gactactaca cactgctcat ttgagaactg   11940
tcagctgagt ggggcaggct tgagttttca tttcatatat ctatatgtct ataagtatat   12000
aaatactata gttatataga taaagagata cgaatttcta tagactgact tttttccattt  12060
tttaaatgtt catgtcacat cctaataga agaaattact tctagtcagt catccaggct   12120
tacctgcttg gtctagaatg gattttttccc ggagccggaa gccaggagga aactacacca   12180
cactaaaaca ttgtctacag ctccagatgt ttctcatttt aaacaactt ccactgacaa    12240
cgaaagtaaa gtaaagtatt ggattttttt aaagggaaca tgtgaatgaa tacacaggac   12300
ttattatatc agagtgagta atcggttggt tggttgattg attgattgat tgatacattc   12360
agcttcctgc tgctagcaat gccacgattt agatttaatg atgcttcagt ggaaatcaat   12420
cagaaggtat tctgacctttg tgaacatcag aaggtatttt ttaactccca agcagtagca   12480
ggacgatgat agggctggag ggctatggat tcccagccca tccctgtgaa ggagtaggcc   12540
actctttaag tgaaggattg gatgattgtt cataatacat aaagttctct gtaattacaa   12600
ctaaattatt atgccctctt ctcacagtca aaaggaactg ggtggtttgg ttttttgttgc  12660
ttttttagat ttattgtccc atgtgggatg agttttttaaa tgccacaaga cataatttaa   12720
aataaataaa ctttgggaaa aggtgtaaaa cagtagccccc atcacatttg tgatactgac   12780
aggtatcaac ccagaagccc atgaactgtg tttccatcct ttgcattctt ctgcgagtgg   12840
ttccacacag gttgtaagt aagtaagaaa gaaggcaaat tgattcaaat gttacaaaaa    12900
aacccttctt ggtggattag acaggttaaa tatataaaca aacaaacaaa aattgctcaa   12960
aaagagagg aaaagctcaa gaggaaaagc taaggactgg taggaaaaag ctttactctt   13020
tcatgccatt ttatttcttt ttgatttttta aatcattcat tcaatagata ccaccgtgtg   13080
acctataatt ttgcaaatct gttacctctg acatcaagtg tattagctt ttggagagtg    13140
ggctgacatc aagtgtaatt agcttttgga gagtgggttt tgtccattat taataattaa   13200
ttaattaaca tcaaacacgg cttctcatgc tatttctacc tcactttggt tttggggtgt   13260
tcctgataat tgtgcacacc tgagttcaca gcttcaccac ttgtccattg cgttatttc     13320
ttttttccttt ataattttct cttttttcctt caataatttc aaaagaaaac ccaaagctct   13380
aaggtaacaa attaccaaat tacatgaaga ttttggttttt gtcttgcatt ttttttcttt   13440
atgtgacgct ggaccttttc tttacccaag gattttttaaa actcagattt aaaacaaggg   13500
gttactttac atcctactaa gaagtttaag taagtaagt tcattctaaa atcagaggta    13560
aataagagtg aataaataat ttgttttaat ctttttgttt ttcttttttaga cacattagct   13620
ctggagtgag tctgtcataa tatttgaaca aaaattgaga gctttattgc tgcattttaa   13680
gcataattaa tttggacatt atttcgtgtt gtgttcttta taaccaccaa gtattaaact    13740
gtaaatcata atgtaactga agcataaaca tcacatggca tgtttttgtca ttgttttcag  13800
gtactgagtt cttacttgag tatcataata tattgtgttt taacaccaac actgtaacat   13860
ttacgaatta tttttttaaa cttcagtttt actgcattttt cacaacatat cagacttcac  13920
caaatatatg ccttactatt gtattatagt actgctttac tgtgtatctc aataaagcac   13980
gcagttatgt tac                                                       13993

SEQ ID NO: 24          moltype = DNA   length = 233
FEATURE                Location/Qualifiers
source                 1..233
                       mol_type = genomic DNA
                       organism = Homo sapiens
SEQUENCE: 24
ctcctactca gactgttact ctggtgacac aacctgtggt tactaaggaa actgccatct    60
ccaaactaga aatgccatct tccttgatgt tggaggtacc tgctctggca gatttcaacc   120
gggcttggac agaacttacc gactggcttt ctctgcttga tcaagttata aaatcacaga   180
gggtgatggt gggtgacctt gaggatatca acgagatgat catcaagcag aag          233

SEQ ID NO: 25          moltype = DNA   length = 182
FEATURE                Location/Qualifiers
source                 1..182
                       mol_type = genomic DNA
                       organism = Homo sapiens
SEQUENCE: 25
atgttgatac cacctatcca gataagaagt ccatcttaat gtacatcaca tcactcttcc    60
aagttttgcc tcaacaagtg agcattgaag ccatccagga agtggaaatg ttgccaaggc   120
cacctaaagt gactaaagaa gaacattttc agttacatca tcaaatgcac tattctcaac   180
ag                                                                    182

SEQ ID NO: 26          moltype = DNA   length = 213
FEATURE                Location/Qualifiers
```

```
source                  1..213
                        mol_type = genomic DNA
                        organism = Homo sapiens
SEQUENCE: 26
gctttacaaa gttctctgca agagcaacaa agtggcctat actatctcag caccactgtg   60
aaagagatgt cgaagaaagc gccctctgaa attagccgga aatatcaatc agaatttgaa  120
gaaattgagg gacgctggaa gaagctctcc tcccagctgg ttgagcattg tcaaaagcta  180
gaggagcaaa tgaataaact ccgaaaaatt cag                                213

SEQ ID NO: 27           moltype = DNA  length = 173
FEATURE                 Location/Qualifiers
source                  1..173
                        mol_type = genomic DNA
                        organism = Homo sapiens
SEQUENCE: 27
aatataaaag atagtctaca acaaagctca ggtcggattg acattattca tagcaagaag   60
acagcagcat tgcaaagtgc aacgcctgtg gaaagggtga agctacagga agctctctcc  120
cagcttgatt tccaatggga aaaagttaac aaaatgtaca aggaccgaca agg          173

SEQ ID NO: 28           moltype = DNA  length = 148
FEATURE                 Location/Qualifiers
source                  1..148
                        mol_type = genomic DNA
                        organism = Homo sapiens
SEQUENCE: 28
gcgatttgac agatctgttg agaaatggcg gcgttttcat tatgatataa agatatttaa   60
tcagtggcta acagaagctg aacagtttct cagaaagaca caaattcctg agaattggga  120
acatgctaaa tacaaatggt atcttaag                                      148

SEQ ID NO: 29           moltype = DNA  length = 148
FEATURE                 Location/Qualifiers
source                  1..148
                        mol_type = genomic DNA
                        organism = Homo sapiens
SEQUENCE: 29
gctagaagaa caaagaaata tcttgtcaga atttcaaaga gatttaaatg aatttgtttt   60
atggttggag gaagcagata acattgctag tatcccactt gaacctggaa aagagcagca  120
actaaaagaa aagcttgagc aagtcaag                                      148

SEQ ID NO: 30           moltype = DNA  length = 109
FEATURE                 Location/Qualifiers
source                  1..109
                        mol_type = genomic DNA
                        organism = Homo sapiens
SEQUENCE: 30
aggaagttag aagatctgag ctctgagtgg aaggcggtaa accgtttact tcaagagctg   60
agggcaaagc agcctgacct agctcctgga ctgaccacta ttggagcct               109

SEQ ID NO: 31           moltype = DNA  length = 176
FEATURE                 Location/Qualifiers
source                  1..176
                        mol_type = genomic DNA
                        organism = Homo sapiens
SEQUENCE: 31
gaactccagg atggcattgg gcagcggcaa actgttgtca gaacattgaa tgcaactggg   60
gaagaaataa ttcagcaatc ctcaaaaaca gatgccagta ttctacagga aaaattggga  120
agcctgaatc tgcggtggca ggaggtctgc aaacagctgt cagacagaaa aaagag      176

SEQ ID NO: 32           moltype = DNA  length = 118
FEATURE                 Location/Qualifiers
source                  1..118
                        mol_type = genomic DNA
                        organism = Homo sapiens
SEQUENCE: 32
gcaacaatgc aggatttgga acagaggcgt ccccagttgg aagaactcat taccgctgcc   60
caaaatttga aaacaagac cagcaatcaa gaggctagaa caatcattac ggatcgaa     118

SEQ ID NO: 33           moltype = DNA  length = 212
FEATURE                 Location/Qualifiers
source                  1..212
                        mol_type = genomic DNA
                        organism = Homo sapiens
SEQUENCE: 33
ttgaaagaat tcagaatcag tgggatgaag tacaagaaca ccttcagaac cggaggcaac   60
agttgaatga aatgttaaag gattcaacac aatggctgga agctaaggaa gaagctgagc  120
aggtcttagg acaggccaga gccaagcttg agtcatggaa ggagggtccc tatacagtag  180
atgcaatcca aaagaaaatc acagaaacca ag                                 212

SEQ ID NO: 34           moltype = DNA  length = 190
```

```
FEATURE                 Location/Qualifiers
source                  1..190
                        mol_type = genomic DNA
                        organism = Homo sapiens
SEQUENCE: 34
ggtgagtgag cgagaggctg ctttggaaga aactcataga ttactgcaac agttccccct    60
ggacctggaa aagtttcttg cctggcttac agaagctgaa acaactgcca atgtcctaca   120
ggatgctacc cgtaaggaaa ggctcctaga agactccaag ggagtaaaag agctgatgaa   180
acaatggcaa                                                          190

SEQ ID NO: 35           moltype = AA   length = 760
FEATURE                 Location/Qualifiers
source                  1..760
                        mol_type = protein
                        organism = Homo sapiens
SEQUENCE: 35
MMDQARSAFS NLFGGEPLSY TRFSLARQVD GDNSHVEMKL AVDEEENADN NTKANVTKPK     60
RCSGSICYGT IAVIVFFLIG FMIGYLGYCK GVEPKTECER LAGTESPVRE EPGEDFPAAR    120
RLYWDDLKRK LSEKLDSTDF TGTIKLLNEN SYVPREAGSQ KDENLALYVE NQFREFKLSK    180
VWRDQHFVKI QVKDSAQNSV IIVDKNGRLV YLVENPGGYV AYSKAATVTG KLVHANFGTK    240
KDFEDLYTPV NGSIVIVRAG KITFAEKVAN AESLNAIGVL IYMDQTKFPI VNAELSFFGH    300
AHLGTGDPYT PGFPSFNHTQ FPPSRSSGLP NIPVQTISRA AAEKLFGNME GDCPSDWKTD    360
STCRMVTSES KNVKLTVSNV LKEIKILNIF GVIKGFVEPD HYVVVGAQRD AWGPGAAKSG    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QNVKHPVTGQ FLYQDSNWAS KVEKLTLDNA    540
AFPFLAYSGI PAVSFCFCED TDYPYLGTTM DTYKELIERI PELNKVARAA AEVAGQFVIK    600
LTHDVELNLD YERYNSQLLS FVRDLNQYRA DIKEMGLSLQ WLYSARGDFF RATSRLTTDF    660
GNAEKTDRFV MKKLNDRVMR VEYHFLSPYV SPKESPFRHV FWGSGSHTLP ALLENLKLRK    720
QNNGAFNETL FRNQLALATW TIQGAANALS GDVWDIDNEF                          760

SEQ ID NO: 36           moltype = DNA   length = 176
FEATURE                 Location/Qualifiers
source                  1..176
                        mol_type = genomic DNA
                        organism = Homo sapiens
SEQUENCE: 36
gaactccagg atggcattgg gcagcggcaa actgttgtca gaacattgaa tgcaactggg    60
gaagaaataa ttcagcaatc ctcaaaaaca gatgccagta ttctacagga aaaattggga   120
agcctgaatc tgcggtggca ggaggtctgc aaacagctgt cagacagaaa aaagag       176
```